US012599324B2

(12) United States Patent
Devgon et al.

(10) Patent No.: US 12,599,324 B2
(45) **Date of Patent: \*Apr. 14, 2026**

(54) SYSTEMS AND METHODS FOR PHLEBOTOMY THROUGH A PERIPHERAL IV CATHETER

(71) Applicant: VELANO VASCULAR, INC., San Francisco, CA (US)

(72) Inventors: Pitamber Devgon, Philadelphia, PA (US); Richard Thomas Briganti, Bala Cynwyd, PA (US); Kenneth Todd Cassidy, Mocksville, NC (US); Marc-Alan Levine, Pottstown, PA (US); Mark Martel, Winston-Salem, NC (US)

(73) Assignee: Velano Vascular, Inc., San Francisco, CA (US)

( * ) Notice: Subject to any disclaimer, the term of this patent is extended or adjusted under 35 U.S.C. 154(b) by 1042 days.

This patent is subject to a terminal disclaimer.

(21) Appl. No.: 17/716,533

(22) Filed: Apr. 8, 2022

(65) Prior Publication Data

US 2022/0225915 A1    Jul. 21, 2022

Related U.S. Application Data

(63) Continuation of application No. 16/028,120, filed on Jul. 5, 2018, now Pat. No. 11,331,023, which is a
(Continued)

(51) Int. Cl.
*A61B 5/15* (2006.01)
*A61B 5/154* (2006.01)
(Continued)

(52) U.S. Cl.
CPC .... *A61B 5/150992* (2013.01); *A61B 5/15003* (2013.01); *A61B 5/150221* (2013.01);
(Continued)

(58) Field of Classification Search
CPC .......... A61B 5/150992; A61B 5/15003; A61B 5/150267; A61B 5/155; A61M 25/0606; A61M 2039/1077
See application file for complete search history.

(56) References Cited

U.S. PATENT DOCUMENTS 3,185,151 A * 5/1965 Czorny .............. A61M 25/0111
                                            D24/112
3,262,448 A   7/1966 Ring et al.
(Continued)

FOREIGN PATENT DOCUMENTS

CN 101884823 A 11/2010
CN 103906470 A 7/2014
(Continued)

OTHER PUBLICATIONS

Examination Report for AU Appl. No. 2015306728, mailed Jul. 16, 2019, 5 pages.
(Continued)

*Primary Examiner* — Sean P Dougherty
(74) *Attorney, Agent, or Firm* — The Webb Law Firm

(57) ABSTRACT

An apparatus includes a catheter, an introducer having a first member and a second member, a locking mechanism coupled to a distal end of the first member and configured to couple the introducer to a peripheral intravenous line, and an actuator coupled to the catheter. The actuator is configured to move from a first configuration, in which the catheter is disposed within the introducer, toward a second configuration to move the second member to a distal position relative to the first member. A portion of a guide of the second member being distal to the first member when the second member is in the distal position. The actuator is configured to move relative to the second member to be placed in the second configuration when the second member is in its distal
(Continued)

position such that the catheter is disposed within and extending past an end of the peripheral intravenous line.

7 Claims, 47 Drawing Sheets

Related U.S. Application Data continuation of application No. 14/468,826, filed on Aug. 26, 2014, now Pat. No. 10,076,272, which is a continuation-in-part of application No. 13/758,585, filed on Feb. 4, 2013, now Pat. No. 9,750,446, which is a continuation of application No. 13/456,900, filed on Apr. 26, 2012, now Pat. No. 8,366,685, which is a continuation-in-part of application No. 13/234,857, filed on Sep. 16, 2011, now Pat. No. 9,186,100.

(60) Provisional application No. 61/479,223, filed on Apr. 26, 2011.

(51) Int. Cl.
| | |
|---|---|
| *A61B 5/155* | (2006.01) |
| *A61M 25/06* | (2006.01) |
| *A61M 39/02* | (2006.01) |
| *A61M 39/10* | (2006.01) |

(52) U.S. Cl.
CPC .. *A61B 5/150267* (2013.01); *A61B 5/150396* (2013.01); *A61B 5/150511* (2013.01); *A61B 5/150572* (2013.01); *A61B 5/150946* (2013.01); *A61B 5/154* (2013.01); *A61M 39/02* (2013.01); *A61M 39/1011* (2013.01); *A61B 5/150259* (2013.01); *A61B 5/150526* (2013.01); *A61B 5/150717* (2013.01); *A61B 5/155* (2013.01); *A61M 25/0606* (2013.01); *A61M 2039/0202* (2013.01); *A61M 2039/1077* (2013.01)

(56) References Cited

U.S. PATENT DOCUMENTS

| | | | | |
|---|---|---|---|---|
| 3,766,913 | A | | 10/1973 | Balin |
| 4,068,659 | A | | 1/1978 | Moorehead |
| 4,192,319 | A | | 3/1980 | Hargens et al. |
| 4,205,675 | A | * | 6/1980 | Vaillancourt ...... A61M 25/0111 |
| | | | | 604/533 |
| 4,314,555 | A | | 2/1982 | Sagae |
| 4,417,886 | A | * | 11/1983 | Frankhouser ..... A61M 25/0606 |
| | | | | 604/528 |
| 4,705,511 | A | | 11/1987 | Kocak |
| 4,790,830 | A | | 12/1988 | Hamacher |
| 4,808,158 | A | | 2/1989 | Kreuzer et al. |
| 4,808,165 | A | | 2/1989 | Carr |
| 4,935,010 | A | | 6/1990 | Cox et al. |
| 4,976,697 | A | | 12/1990 | Walder et al. |
| 5,013,304 | A | | 5/1991 | Russell et al. |
| 5,047,018 | A | | 9/1991 | Gay et al. |
| 5,057,092 | A | | 10/1991 | Webster, Jr. |
| 5,069,674 | A | | 12/1991 | Fearnot et al. |
| 5,100,390 | A | | 3/1992 | Lubeck et al. |
| 5,135,492 | A | * | 8/1992 | Melker .............. A61B 5/15003 |
| | | | | 604/86 |
| 5,135,502 | A | | 8/1992 | Koenig, Jr. et al. |
| 5,147,334 | A | | 9/1992 | Moss |
| 5,201,722 | A | | 4/1993 | Moorehead et al. |
| 5,203,771 | A | | 4/1993 | Melker et al. |
| 5,254,107 | A | | 10/1993 | Soltesz |
| 5,270,003 | A | | 12/1993 | Bernes et al. |
| 5,354,267 | A | * | 10/1994 | Niermann ......... A61M 16/0463 |
| | | | | 128/207.14 |
| 5,360,407 | A | | 11/1994 | Leonard |

| | | | | |
|---|---|---|---|---|
| 5,368,029 | A | | 11/1994 | Holcombe et al. |
| 5,405,323 | A | | 4/1995 | Rogers et al. |
| 5,415,636 | A | | 5/1995 | Forman |
| 5,479,857 | A | | 1/1996 | Braun |
| 5,552,118 | A | | 9/1996 | Mayer |
| 5,553,625 | A | | 9/1996 | Rao |
| 5,562,631 | A | | 10/1996 | Bogert |
| 5,611,782 | A | | 3/1997 | Haedt |
| 5,658,263 | A | | 8/1997 | Dang et al. |
| D384,741 | S | | 10/1997 | Musgrave et al. |
| 5,704,914 | A | | 1/1998 | Stocking et al. |
| 5,713,876 | A | | 2/1998 | Bogert et al. |
| 5,749,857 | A | | 5/1998 | Cuppy |
| 5,755,709 | A | | 5/1998 | Cuppy |
| 5,807,350 | A | | 9/1998 | Diaz |
| 5,827,229 | A | | 10/1998 | Auth et al. |
| 5,848,996 | A | | 12/1998 | Eldor |
| 5,853,393 | A | | 12/1998 | Bogert |
| 5,897,537 | A | | 4/1999 | Berg et al. |
| 5,911,715 | A | | 6/1999 | Berg et al. |
| 5,928,166 | A | | 7/1999 | Shemesh et al. |
| 5,944,690 | A | | 8/1999 | Falwell et al. |
| 5,944,695 | A | | 8/1999 | Johnson et al. |
| 5,976,107 | A | | 11/1999 | Mertens et al. |
| 6,036,677 | A | | 3/2000 | Javier, Jr. et al. |
| 6,059,759 | A | | 5/2000 | Mottola et al. |
| 6,080,138 | A | | 6/2000 | Lemke et al. |
| 6,093,177 | A | | 7/2000 | Javier, Jr. et al. |
| 6,126,618 | A | | 10/2000 | Bischof |
| 6,197,001 | B1 | | 3/2001 | Wilson et al. |
| 6,394,979 | B1 | | 5/2002 | Sharp et al. |
| 6,508,790 | B1 | | 1/2003 | Lawrence |
| 6,537,254 | B1 | | 3/2003 | Schock et al. |
| 6,585,703 | B1 | | 7/2003 | Kassel et al. |
| 6,648,835 | B1 | | 11/2003 | Shemesh |
| 6,652,507 | B2 | | 11/2003 | Pepin |
| 6,685,664 | B2 | | 2/2004 | Levin et al. |
| 6,692,473 | B2 | | 2/2004 | St. Cyr et al. |
| 6,712,790 | B1 | | 3/2004 | Prestidge et al. |
| 6,719,726 | B2 | | 4/2004 | Meng et al. |
| 6,719,781 | B1 | | 4/2004 | Kim |
| 6,722,370 | B1 | | 4/2004 | Mann |
| 6,726,675 | B1 | | 4/2004 | Beyar |
| 6,755,812 | B2 | | 6/2004 | Peterson et al. |
| 6,858,024 | B1 | | 2/2005 | Berg et al. |
| 6,872,193 | B2 | | 3/2005 | Shaw et al. |
| 6,908,459 | B2 | | 6/2005 | Harding et al. |
| 6,913,595 | B2 | | 7/2005 | Mastorakis |
| 7,008,404 | B2 | | 3/2006 | Nakajima |
| 7,087,047 | B2 | | 8/2006 | Kraus et al. |
| 7,135,008 | B2 | | 11/2006 | O'Mahony et al. |
| 7,252,654 | B2 | | 8/2007 | VanTassel et al. |
| 7,311,689 | B2 | | 12/2007 | Levin et al. |
| 7,316,678 | B2 | | 1/2008 | Nash et al. |
| 7,462,161 | B2 | | 12/2008 | O'Mahony et al. |
| 7,615,033 | B2 | | 11/2009 | Leong |
| 7,625,367 | B2 | | 12/2009 | Adams et al. |
| 7,662,110 | B2 | | 2/2010 | Flaherty |
| 7,670,320 | B2 | | 3/2010 | Iwase et al. |
| 7,685,367 | B2 | | 3/2010 | Ruia et al. |
| 7,691,088 | B2 | | 4/2010 | Howell |
| 7,713,250 | B2 | | 5/2010 | Harding et al. |
| 7,717,882 | B2 | | 5/2010 | Harding |
| 7,717,899 | B2 | | 5/2010 | Bowe et al. |
| 7,762,977 | B2 | | 7/2010 | Porter et al. |
| 7,766,961 | B2 | | 8/2010 | Patel et al. |
| 7,771,394 | B2 | | 8/2010 | Shue et al. |
| 7,892,208 | B2 | | 2/2011 | Schnell et al. |
| 7,972,294 | B2 | | 7/2011 | Nash et al. |
| 8,048,031 | B2 | | 11/2011 | Shaw et al. |
| 8,062,226 | B2 | | 11/2011 | Moore |
| 8,092,374 | B2 | | 1/2012 | Smith et al. |
| 8,104,475 | B2 | | 1/2012 | Cheung |
| 8,114,057 | B2 | | 2/2012 | Gerdts et al. |
| 8,162,890 | B2 | | 4/2012 | Amisar et al. |
| 8,251,978 | B2 | | 8/2012 | Nash et al. |
| 8,267,911 | B2 | | 9/2012 | Gallogly et al. |
| 8,328,759 | B2 | * | 12/2012 | Donawick ......... A61M 25/0612 |
| | | | | 604/164.01 |

(56) References Cited

U.S. PATENT DOCUMENTS

| | | | |
|---|---|---|---|
| 8,361,013 B2 | 1/2013 | Wood, Jr. | |
| 8,361,014 B2 | 1/2013 | Wood, Jr. | |
| 8,366,685 B2 | 2/2013 | Devgon | |
| 8,372,032 B2 | 2/2013 | Wood, Jr. | |
| 8,425,532 B2 | 4/2013 | Flom et al. | |
| 8,444,605 B2 | 5/2013 | Kuracina et al. | |
| 8,491,568 B2 | 7/2013 | Schertiger et al. | |
| 8,506,533 B2 | 8/2013 | Carlyon et al. | |
| 8,523,801 B2 | 9/2013 | Nash et al. | |
| 8,532,730 B2 | 9/2013 | Brister et al. | |
| 8,690,833 B2 | 4/2014 | Belson | |
| 8,696,639 B2 | 4/2014 | Smith et al. | |
| 8,702,658 B2 | 4/2014 | Spearman | |
| 8,721,546 B2 | 5/2014 | Belson | |
| 8,728,035 B2 | 5/2014 | Warring et al. | |
| 8,728,038 B2 | 5/2014 | Spearman | |
| 8,728,058 B2 | 5/2014 | Schertiger | |
| 8,753,312 B2 | 6/2014 | Bowe et al. | |
| 8,808,246 B2 | 8/2014 | Cabot | |
| 8,876,773 B2 | 11/2014 | Ishida | |
| 8,932,259 B2 | 1/2015 | Stout et al. | |
| 8,936,581 B2 | 1/2015 | Bihlmaier | |
| 8,974,411 B2 | 3/2015 | McKinnon | |
| 9,028,425 B2 | 5/2015 | Burkholz | |
| 9,056,182 B2 | 6/2015 | Moulton et al. | |
| 9,084,851 B2 | 7/2015 | Kosinski et al. | |
| 9,089,474 B2 | 7/2015 | Cederschiöld | |
| 9,101,746 B2 | 8/2015 | Stout et al. | |
| 9,114,241 B2 | 8/2015 | Stout et al. | |
| 9,126,012 B2 | 9/2015 | McKinnon et al. | |
| 9,149,604 B2 | 10/2015 | Nishide et al. | |
| 9,155,876 B2 | 10/2015 | Sonderegger et al. | |
| 9,186,100 B2 | 11/2015 | Devgon | |
| 9,198,610 B2 | 12/2015 | Davis et al. | |
| 9,233,208 B2 | 1/2016 | Tekeste | |
| 9,302,049 B2 | 4/2016 | Tekeste | |
| 9,314,201 B2 | 4/2016 | Burkholz et al. | |
| 9,352,119 B2 | 5/2016 | Burkholz et al. | |
| 9,352,128 B2 | 5/2016 | Ishida | |
| 9,358,335 B2 | 6/2016 | Wada et al. | |
| 9,399,112 B2 | 7/2016 | Shevgoor et al. | |
| 9,402,975 B2 | 8/2016 | Shevgoor | |
| 9,408,569 B2 | 8/2016 | Andreae et al. | |
| 9,415,185 B2 | 8/2016 | Notter | |
| 9,480,794 B2 | 11/2016 | Keith et al. | |
| 9,522,229 B2 | 12/2016 | Sonderegger et al. | |
| 9,522,237 B2 | 12/2016 | Alheidt et al. | |
| 9,549,701 B2 | 1/2017 | Peterson et al. | |
| 9,579,486 B2 | 2/2017 | Burkholz et al. | |
| 9,592,374 B2 | 3/2017 | Muse | |
| 9,616,214 B2 | 4/2017 | Stout et al. | |
| 9,737,686 B2 | 8/2017 | Trainer et al. | |
| 9,744,344 B1 | 8/2017 | Devgon et al. | |
| 9,750,446 B2 | 9/2017 | Devgon | |
| 9,770,580 B2 | 9/2017 | Burkholz et al. | |
| 9,895,092 B2 | 2/2018 | Burkholz | |
| 9,907,913 B2 | 3/2018 | Kosinski et al. | |
| 9,909,162 B2 | 3/2018 | Yeh | |
| 9,919,826 B2 | 3/2018 | Ivosevic et al. | |
| 9,943,676 B2 | 4/2018 | Tekeste | |
| 9,980,878 B2 | 5/2018 | Marici et al. | |
| 9,993,634 B2 | 6/2018 | Christensen et al. | |
| 10,010,685 B2 | 7/2018 | Ferreri et al. | |
| 10,039,884 B2 | 8/2018 | Ferreri et al. | |
| 10,046,155 B2 | 8/2018 | Carter et al. | |
| 10,064,576 B2 | 9/2018 | Devgon | |
| 10,076,272 B2 | 9/2018 | Devgon et al. | |
| 10,105,085 B2 | 10/2018 | Andreae et al. | |
| 10,105,494 B2 | 10/2018 | Alheidt et al. | |
| 10,143,411 B2 | 12/2018 | Cabot | |
| 10,182,753 B2 | 1/2019 | Davis et al. | |
| 10,219,982 B2 | 3/2019 | Weir et al. | |
| 10,232,140 B2 | 3/2019 | McKinnon | |
| 10,300,247 B2 | 5/2019 | Devgon et al. | |
| 10,307,571 B2 | 6/2019 | Burkholz | |
| 10,391,031 B2 | 8/2019 | Yevmenenko et al. | |
| 10,674,950 B2 | 6/2020 | Devgon | |
| 10,729,367 B1 | 8/2020 | Devgon | |
| 10,799,167 B1 | 10/2020 | Devgon | |
| 11,191,465 B2 | 12/2021 | Devgon | |
| 2002/0120215 A1 | 8/2002 | Crawford et al. | |
| 2003/0009150 A1 | 1/2003 | Pepin | |
| 2003/0083620 A1 | 5/2003 | Luther et al. | |
| 2003/0225369 A1 | 12/2003 | McMichael et al. | |
| 2004/0092879 A1 | 5/2004 | Kraus et al. | |
| 2004/0138622 A1 | 7/2004 | Palasis | |
| 2004/0181192 A1 | 9/2004 | Cuppy | |
| 2005/0015048 A1 | 1/2005 | Chiu et al. | |
| 2005/0090801 A1 | 4/2005 | Racz et al. | |
| 2005/0096609 A1 | 5/2005 | Maginot et al. | |
| 2005/0119597 A1 | 6/2005 | O'Mahony et al. | |
| 2005/0137576 A1 | 6/2005 | Packard | |
| 2005/0165355 A1 | 7/2005 | Fitzgerald | |
| 2005/0192558 A1 | 9/2005 | Bernard et al. | |
| 2005/0273076 A1 | 12/2005 | Beasley et al. | |
| 2006/0015068 A1 | 1/2006 | Amisar et al. | |
| 2006/0100582 A1 | 5/2006 | Marianowicz et al. | |
| 2006/0142694 A1 | 6/2006 | Bednarek et al. | |
| 2006/0155209 A1 | 7/2006 | Miller et al. | |
| 2006/0155244 A1 | 7/2006 | Popov | |
| 2007/0088279 A1 | 4/2007 | Shue et al. | |
| 2007/0100295 A1 | 5/2007 | Belley et al. | |
| 2007/0219460 A1 | 9/2007 | Goldenberg | |
| 2007/0282280 A1 | 12/2007 | Tennican | |
| 2008/0033396 A1 | 2/2008 | Danek et al. | |
| 2008/0045862 A1 | 2/2008 | Dalebout et al. | |
| 2008/0058587 A1 | 3/2008 | Boyden et al. | |
| 2008/0086042 A1 | 4/2008 | Brister et al. | |
| 2008/0097407 A1 | 4/2008 | Plishka | |
| 2008/0287918 A1 | 11/2008 | Rosenman et al. | |
| 2008/0300574 A1 | 12/2008 | Belson et al. | |
| 2008/0319387 A1 | 12/2008 | Amisar et al. | |
| 2009/0024057 A1 | 1/2009 | Owen et al. | |
| 2009/0156963 A1 | 6/2009 | Noble et al. | |
| 2009/0192496 A1 | 7/2009 | Suwito et al. | |
| 2009/0209912 A1 | 8/2009 | Keyser et al. | |
| 2009/0312807 A1 | 12/2009 | Boudreault et al. | |
| 2010/0121218 A1 | 5/2010 | Mugan et al. | |
| 2010/0137778 A1* | 6/2010 | Kunjan | A61B 5/150755 |
| | | | 604/6.15 |
| 2010/0160863 A1 | 6/2010 | Heuser | |
| 2010/0210934 A1 | 8/2010 | Belson | |
| 2010/0286657 A1 | 11/2010 | Heck | |
| 2010/0305519 A1 | 12/2010 | McKinnon et al. | |
| 2010/0312179 A1 | 12/2010 | Nikolchev et al. | |
| 2011/0015577 A1 | 1/2011 | Baney et al. | |
| 2012/0016307 A1 | 1/2012 | Burkholz et al. | |
| 2012/0041392 A1 | 2/2012 | Donawick | |
| 2012/0046648 A1 | 2/2012 | Scheckel | |
| 2012/0053523 A1 | 3/2012 | Harding | |
| 2012/0109079 A1 | 5/2012 | Asleson et al. | |
| 2012/0157968 A1 | 6/2012 | Eldredge et al. | |
| 2012/0172754 A1 | 7/2012 | Baid | |
| 2012/0191010 A1 | 7/2012 | Cabot et al. | |
| 2012/0197200 A1 | 8/2012 | Belson | |
| 2012/0239046 A1 | 9/2012 | Kaiser et al. | |
| 2012/0277627 A1 | 11/2012 | Devgon | |
| 2012/0277630 A1 | 11/2012 | Devgon | |
| 2012/0316466 A1* | 12/2012 | Crawford | A61B 5/150404 |
| | | | 600/576 |
| 2013/0006226 A1 | 1/2013 | Hong et al. | |
| 2013/0102888 A1 | 4/2013 | Slim | |
| 2013/0121897 A1 | 5/2013 | Davis et al. | |
| 2013/0131597 A1 | 5/2013 | Blaivas et al. | |
| 2013/0281925 A1 | 10/2013 | Benscoter et al. | |
| 2013/0289537 A1 | 10/2013 | Schertiger et al. | |
| 2014/0012085 A1 | 1/2014 | Smith et al. | |
| 2014/0046214 A1 | 2/2014 | Devgon | |
| 2014/0107427 A1 | 4/2014 | Chow et al. | |
| 2014/0107800 A1 | 4/2014 | Flom et al. | |
| 2014/0128774 A1 | 5/2014 | Andreae et al. | |
| 2014/0128775 A1 | 5/2014 | Andreae et al. | |
| 2014/0171803 A1 | 6/2014 | Van Hoven et al. | |
| 2014/0180127 A1 | 6/2014 | Meyer et al. | |

(56) References Cited

U.S. PATENT DOCUMENTS

| | | |
|---|---|---|
| 2014/0188002 A1 | 7/2014 | Close et al. |
| 2014/0188003 A1 | 7/2014 | Belson |
| 2014/0194833 A1 | 7/2014 | Andrus |
| 2014/0296745 A1 | 10/2014 | Cash |
| 2014/0358120 A1 | 12/2014 | Haarala et al. |
| 2014/0364766 A1 | 12/2014 | Devgon et al. |
| 2014/0378867 A1 | 12/2014 | Belson |
| 2015/0005669 A1 | 1/2015 | Burkholz |
| 2015/0038909 A1 | 2/2015 | Christensen et al. |
| 2015/0065952 A1 | 3/2015 | Pacheco et al. |
| 2015/0112313 A1 | 4/2015 | Schertiger |
| 2015/0119859 A1 | 4/2015 | Cajamarca et al. |
| 2015/0119863 A1 | 4/2015 | Christensen et al. |
| 2015/0123398 A1 | 5/2015 | Sanders et al. |
| 2015/0148747 A1 | 5/2015 | Whitley |
| 2015/0208973 A1 | 7/2015 | Burkholz |
| 2015/0209510 A1 | 7/2015 | Burkholz et al. |
| 2015/0297456 A1 | 10/2015 | Marici et al. |
| 2015/0306345 A1 | 10/2015 | Burkholz et al. |
| 2015/0313526 A1 | 11/2015 | Van Wieren |
| 2015/0320937 A1 | 11/2015 | Kosinski et al. |
| 2015/0360005 A1 | 12/2015 | Arellano Cabrera et al. |
| 2016/0008517 A1 | 1/2016 | Burkholz et al. |
| 2016/0015945 A1 | 1/2016 | Warring et al. |
| 2016/0022963 A1 | 1/2016 | Belson |
| 2016/0038067 A1 | 2/2016 | Davis et al. |
| 2016/0073937 A1 | 3/2016 | Burkholz et al. |
| 2016/0166772 A1 | 6/2016 | Mirzazadeh et al. |
| 2016/0206858 A1 | 7/2016 | Shida |
| 2016/0220786 A1 | 8/2016 | Mitchell et al. |
| 2016/0220790 A1 | 8/2016 | Borowicz |
| 2016/0256667 A1 | 9/2016 | Ribelin et al. |
| 2017/0043066 A1 | 2/2017 | Laub |
| 2017/0056595 A1 | 3/2017 | Alheidt et al. |
| 2017/0120008 A1 | 5/2017 | Burkholz et al. |
| 2017/0120012 A1 | 5/2017 | Sonderegger et al. |
| 2017/0216564 A1 | 8/2017 | Devgon et al. |
| 2017/0354779 A1 | 12/2017 | Atterbury et al. |
| 2017/0360345 A1 | 12/2017 | Devgon |
| 2018/0133438 A1 | 5/2018 | Hulvershorn et al. |
| 2018/0272106 A1 | 9/2018 | Funk et al. |
| 2018/0272107 A1 | 9/2018 | Ehrenreich et al. |
| 2018/0368747 A1 | 12/2018 | Devgon |
| 2019/0021640 A1* | 1/2019 | Burkholz ......... A61B 5/150343 |
| 2019/0022324 A1 | 1/2019 | Tekeste |
| 2019/0209726 A1 | 7/2019 | Ma et al. |
| 2020/0100716 A1 | 4/2020 | Devgon et al. |

FOREIGN PATENT DOCUMENTS

| | | | |
|---|---|---|---|
| EP | 1191970 B1 | 3/2006 | |
| EP | 2504054 B1 | 9/2013 | |
| JP | S55119739 U | 8/1980 | |
| JP | 2002534203 A | 10/2002 | |
| JP | 200729732 A | 2/2007 | |
| JP | 2010505534 A | 2/2010 | |
| RU | 2271835 C2 | 3/2006 | |
| WO | 9621393 A1 | 7/1996 | |
| WO | WO-9726037 A1 * | 7/1997 | .......... A61M 39/045 |
| WO | 9839054 A1 | 9/1998 | |
| WO | 9916496 A1 | 4/1999 | |
| WO | 0041617 A1 | 7/2000 | |
| WO | 0049939 A1 | 8/2000 | |
| WO | 2004056414 A1 | 7/2004 | |
| WO | 2004089437 A2 | 10/2004 | |
| WO | 2006065949 A2 | 6/2006 | |
| WO | 2006090637 A1 | 8/2006 | |
| WO | 2006126002 A1 | 11/2006 | |
| WO | 2008097949 A1 | 8/2008 | |
| WO | 2008130077 A1 | 10/2008 | |
| WO | 2008138351 A1 | 11/2008 | |
| WO | 2009029216 A1 | 3/2009 | |
| WO | 2009152470 A1 | 12/2009 | |
| WO | 2010065901 A1 | 6/2010 | |
| WO | 2010089154 A1 | 8/2010 | |
| WO | 2010107949 A1 | 9/2010 | |
| WO | 2011011436 A2 | 1/2011 | |
| WO | 2011030282 A1 | 3/2011 | |
| WO | 2012064786 A1 | 5/2012 | |
| WO | 2012149109 A2 | 11/2012 | |
| WO | 2013174381 A1 | 11/2013 | |
| WO | 2014093472 A1 | 6/2014 | |
| WO | 2016033143 A1 | 3/2016 | |
| WO | 2016089871 A1 | 6/2016 | |
| WO | 2016178974 A1 | 11/2016 | |
| WO | 2017074674 A1 | 5/2017 | |
| WO | 2018175529 A1 | 9/2018 | |
| WO | 2018175590 A1 | 9/2018 | |

OTHER PUBLICATIONS

Examination Report for Indian Patent Appl. No. 9401/DELNP/2013, mailed Nov. 27, 2019, 7 pages.

Extended European Search Report for European Appl. No. 17748206.4 dated Aug. 8, 2019, 9 pages.

International Search Report and Written Opinion from International Appl. No. PCT/US2010/042635, mailed Feb. 25, 2011.

International Search Report and Written Opinion for International Appl. No. PCT/US2012/035122, mailed Feb. 14, 2014.

International Search Report and Written Opinion for International Appl. No. PCT/US2015/046863, mailed Dec. 21, 2015.

International Search Report and Written Opinion for International Appl. No. PCT/US2017/016359, mailed Jun. 26, 2017, 13 pages.

International Search Report and Written Opinion from International Appl. No. PCT/US2018/023479, mailed Aug. 3, 2018, 10 pages.

International Search Report and Written Opinion from International Appl. No. PCT/US2018/023575, mailed Aug. 18, 2018, 10 pages.

International Search Report and Written Opinion for International Appl. No. PCT/US2018/067631, mailed Mar. 29, 2019, 8 pages.

International Search Report and Written Opinion for International Appl. No. PCT/US2019/053581, mailed Jan. 20, 2020, 18 pages.

Notice of Preliminary Rejection for Korean Patent Appl. No. 10-2013-7030879, mailed Feb. 6, 2018, 11 pages.

Office Action for Chinese Patent Appl. No. 201280029672.2, mailed May 26, 2015, 21 pgs.

Office Action for Japanese Patent Appl. No. 2014-508539, mailed Feb. 26, 2016, 4 pgs.

Office Action for Japanese Patent Appl. No. 2014-508539, mailed Nov. 1, 2016, 6 pgs.

Office Action for Japanese Patent Appl. No. 2017-038135, dated Feb. 14, 2018, 5 pages.

Office Action for Japanese Patent Appl. No. 2019-090357, mailed Mar. 18, 2020, 12 pgs.

Office Action for Russian Patent Appl. No. 2013152251, mailed Feb. 24, 2016, 6 pgs.

Office Action for Russian Patent Appl. No. 201709889/14, mailed Oct. 16, 2018, with English translation, 23 pgs.

Office Action for U.S. Appl. No. 13/234,857, mailed Apr. 16, 2015, 17 pgs.

Office Action for U.S. Appl. No. 13/456,900, mailed Sept 5, 2012.

Office Action for U.S. Appl. No. 13/456,900, mailed Nov. 2, 2012.

Office Action for U.S. Appl. No. 13/758,585, mailed Jan. 27, 2017, 5 pages.

Office Action for U.S. Appl. No. 13/758,585, mailed Jun. 10, 2015, 20 pgs.

Office Action for U.S. Appl. No. 13/758,585, mailed May 16, 2016, 8 pages.

Office Action for U.S. Appl. No. 13/758,585, mailed Oct. 30, 2015, 14 pgs.

Office Action for U.S. Appl. No. 14/468,826, mailed Oct. 26, 2017, 7 pages.

Office Action for U.S. Appl. No. 15/014,834, mailed May 16, 2018, 33 pages.

Office Action for U.S. Appl. No. 15/199,290, mailed Dec. 7, 2016, 30 pgs.

Office Action for U.S. Appl. No. 15/680,952, mailed Dec. 6, 2017, 27 pages.

(56) References Cited

OTHER PUBLICATIONS

Office Action for U.S. Appl. No. 15/927,506, mailed Mar. 17, 2020, 21 pgs.

Office Action for U.S. Appl. No. 16/806,949, mailed Apr. 24, 2020, 7 pgs.

Office Action for U.S. Appl. No. 16/844,730, mailed May 14, 2020, 18 pgs.

Supplementary European Search Report for European Appl. No. EP 12776089.0, mailed May 13, 2015, 7pgs.

"Blood Sampling Hemolysis Study for the MaxPlus Positive Flow Connector," Maximus Medical Products, Inc. 2003, 1 page.

"Connect and Protect with BD Diagnostics—Preanalytical Systems," BD Vacutainer, Luer-Lok, Access Device, 2006, 2 pages.

Cox et al., "Blood Samples Drawn from IV Catheters Have Less Hemolysis When 5-mL (vs 10-mL) Collection Tubes are Used," J Emerg Nurs., 2004, 2 pages.

"Evidence-Based Practice (EBP) Guideline Drawing Labs from peripheral IV Sites," Nursing Research Council of United Hospital—developed Apr. 2004; revised Mar. 2009, 3 pages.

Frey, "Drawing Blood Samples From Vascular Access Devices: Evidence-based Practice," Journal of Infusion Nursing: Sep./Oct. 2003, pp. 285-293, vol. 26:5, Article: CE, Abstract, [retrieved on Mar. 16, 2011], 1 page.

Hadaway, "Reopen the Pipeline," Nursing, 2005, vol. 5:8, 11 pages.

Himberger Jr., "Accuracy of drawing blood through infusing intravenous lines," 2001, retrieved from http://www.ncbi.nlm.nih.gov/pubmed/?term=Accuracy%20of%20drawing%20blood%20through%20infusing%20intravenous%20lines>.

Imura Akira et al., "Anatomical Study of Distribution of Valves of the Cutaneous Veins of Adult's Limbs," Annals of Anatomy, 2003, pp. 91-95, vol. 185.

Jagger et al., "Drawing Venous Blood With Syringes: A Risky Use of Injection Equipment," Advances in Exposure Prevention, 2000, vol. 5:3, 3 pages.

Kiray et al., "Anatomical Evaluation of the Superficial Veins of the Upper Extremity as Graft Donor Source in Microvascular Reconstructions: A Cadaveric Study," Acta Orthopaedica et Traumatologica Turcica, 2013, pp. 405-410, vol. 47:6.

Mikuni et al., "Topographical Anatomy of Superficial Veins, Cutaneous Nerves, and Arteries at Venipuncture Sites in the Cubital Fossa," Anatomical Science International, 2013, pp. 46-57, vol. 88.

"Needleless IV Access Devices," BD Q-Style, Luer Access Split-Septum, 2007, 1 page.

"Vascular Access Procedures," Vascular Access Procedures, [retrieved on Mar. 16, 2011] Retrieved from the Internet <URL: http://www.radiologyinfo.orq/en/info.cfm?pq=vasc_access> 7 pages.

Velano Vascular, "Introducing PIVO" [Retrieved from the Internet] <URL: http://velanovascular.com/solutions/>, 2017.

WHO guidelines on drawing blood: best practices in phlebotomy, World Health Organization, 2010, 125 pages.

* cited by examiner

4200

4202

4231

4230

13400

13400

13400

13400

13400

13400

14400

14400

200

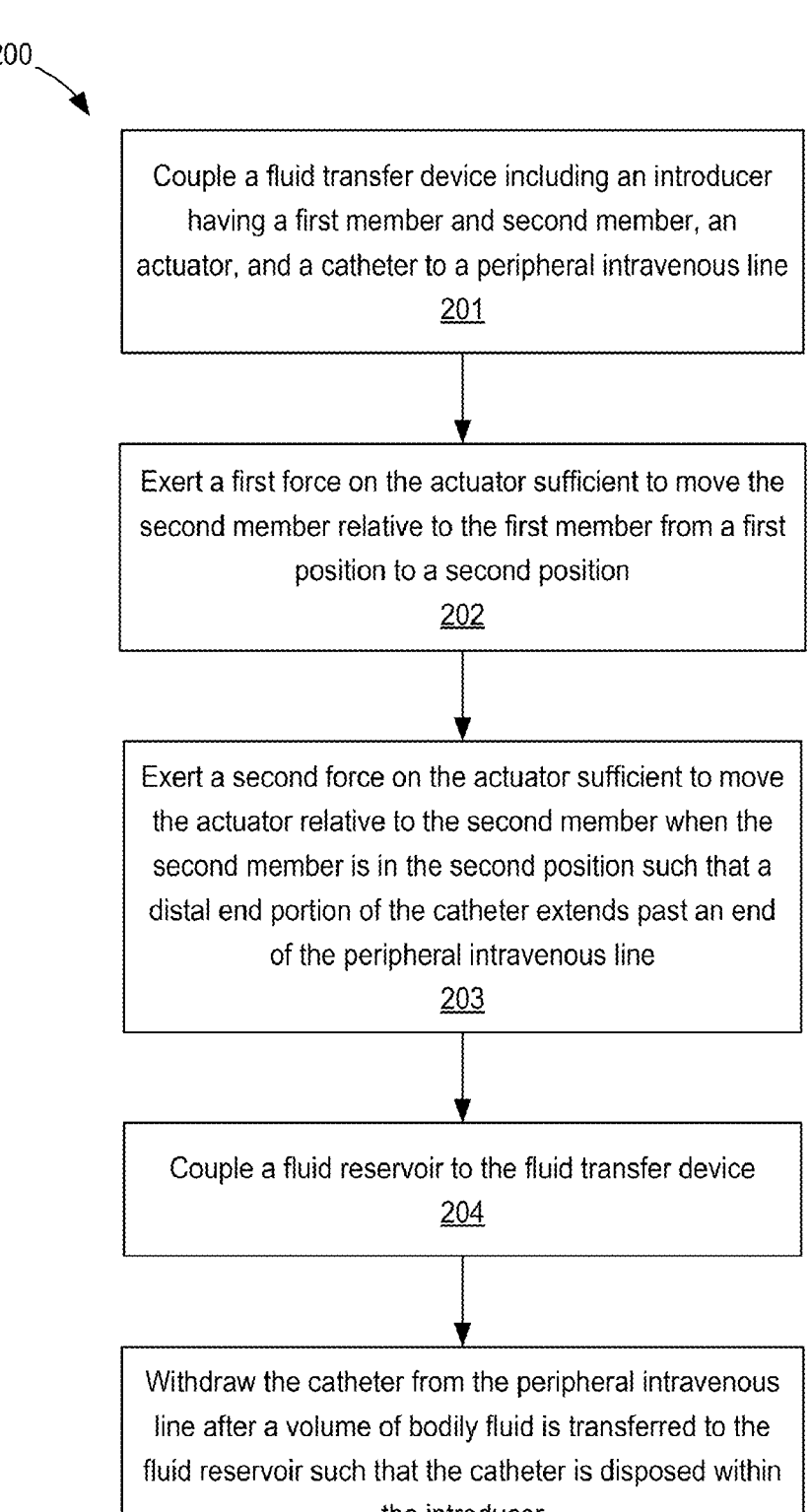

Couple a fluid transfer device including an introducer having a first member and second member, an actuator, and a catheter to a peripheral intravenous line
201

Exert a first force on the actuator sufficient to move the second member relative to the first member from a first position to a second position
202

Exert a second force on the actuator sufficient to move the actuator relative to the second member when the second member is in the second position such that a distal end portion of the catheter extends past an end of the peripheral intravenous line
203

Couple a fluid reservoir to the fluid transfer device
204

Withdraw the catheter from the peripheral intravenous line after a volume of bodily fluid is transferred to the fluid reservoir such that the catheter is disposed within the introducer
205

FIG. 77

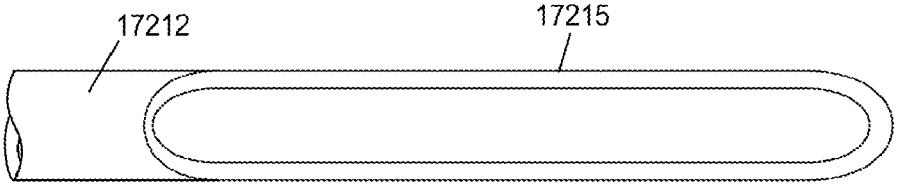
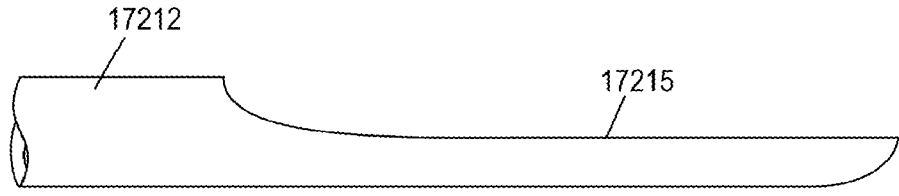
FIG. 78
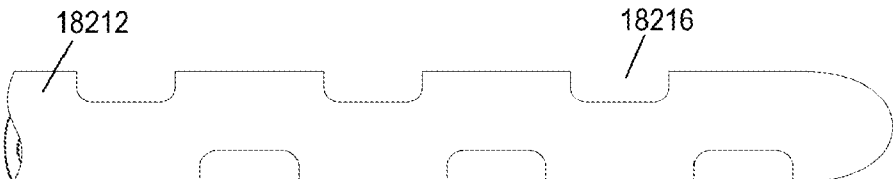
FIG. 79

SYSTEMS AND METHODS FOR PHLEBOTOMY THROUGH A PERIPHERAL IV CATHETER

CROSS-REFERENCE TO RELATED APPLICATIONS

This application is a continuation of U.S. patent application Ser. No. 16/028,120, entitled "Systems and Methods for Phlebotomy Through a Peripheral IV Catheter", filed Jul. 5, 2018, which is a continuation of U.S. patent application Ser. No. 14/468,826, entitled "Systems and Methods for Phlebotomy Through a Peripheral IV Catheter", filed Aug. 26, 2014 (now U.S. Pat. No. 10,076,272), which is a continuation-in-part of U.S. patent application Ser. No. 13/758,585, entitled "Systems and Methods for Phlebotomy Through a Peripheral IV Catheter", filed Feb. 4, 2013 (now U.S. Pat. No. 9,750,446), which is a continuation of U.S. patent application Ser. No. 13/456,900 entitled "Systems and Methods for Phlebotomy Through a Peripheral IV Catheter", filed Apr. 26, 2012 (now U.S. Pat. No. 8,366,685), which is a continuation-in-part of U.S. patent application Ser. No. 13/234,857, entitled "Systems and Methods for Phlebotomy Through a Peripheral IV Catheter", filed on Sep. 16, 2011 (now U.S. Pat. No. 9,186,100), which claims priority to U.S. Provisional Patent Application Ser. No. 61/479,223, entitled "Systems and Methods for Phlebotomy Through a Peripheral IV Catheter", filed on Apr. 26, 2011, the disclosures of which are incorporated herein by reference in their entireties.

BACKGROUND

The embodiments described herein relate generally to medical devices. More particularly, the embodiments described herein relate to systems and methods for phlebotomy through an intravenous catheter.

The typical hospitalized patient encounters a needle every time a doctor orders a lab test. The standard procedure for blood extraction involves using a metal needle ("butterfly needle") to "stick" patients' veins in their arms or hands. Blood drawing is a manual, labor-intensive process, with the average patient requiring hours of direct skilled labor during a typical hospital stay. This needle stick is not only painful and a major source of patient dissatisfaction, but the nurses or specialized blood drawing personnel (phlebotomists) often have difficulty finding the vein in approximately 10-15% of patients, resulting in multiple, painful "stick" attempts. This results in significantly higher material and labor costs (needles and tubing must be disposed of after every attempt) and increased patient pain and bruising.

The current process for drawing blood is inefficient, taking on average 7-10 minutes, and more than 21 minutes for 10% of patients. These 10% of patients are referred to as Difficult Intra-Venous Access or more commonly as "tough stick" patients. If superficial veins are not readily apparent, blood can be forced into the vein by massaging the arm from wrist to elbow, tapping the site with the index and middle finger, applying a warm, damp washcloth to the site for 5 minutes, or by lowering the extremity over the bedside to allow the veins to fill. Each of these methods is time consuming and therefore costly.

Peripheral IV catheters (PIVs) are inserted into most patients while they are hospitalized and used for infusing fluids and medications. However, they are not designed for blood extractions. The failure rates for aspiration reach 20-50% when PIVs have been left inserted for more than a day. Blood extracted from PIVs is often hemolyzed (e.g., defined as the rupture of red blood cells and the release of their contents into surrounding fluid) resulting in a discarded sample and the need to repeat the blood collection.

There are several mechanical barriers that can contribute to the shortcomings of extracting blood from a PIV. First, most catheters are formed from a soft bio-reactive polymer, the use of this material has led to a potential narrowing or collapse of the catheter as the negative pressure is applied for aspiration or the catheter is kinked during insertion or manipulation, preventing backflow. Additionally, with longer indwelling times comes an increase in debris (e.g., fibrin/platelet clots) that build up on the tip of the catheter and within the lumen. This explains the relationship between failure rate and indwelling time. A third significant barrier is attributed to a "suction cup" effect, wherein the negative pressure created by aspiration through the catheter and the possible curved path of a vein result in the tip of the catheter adhering to the wall of the vein. As the negative pressure increases the vein can rupture resulting in "blowing the vein," a major concern for phlebotomists during aspiration through a PIV.

Thus, a need exists for an improved system and method for phlebotomy through a peripheral intravenous catheter.

SUMMARY

Systems and methods for phlebotomy through a peripheral intravenous catheter are described herein. In some embodiments, an apparatus includes a catheter having a proximal end portion and a distal end portion and defining a lumen therethrough, an introducer having a first member and a second member, a locking mechanism coupled to a distal end of the first member, and an actuator coupled to the catheter. At least a portion of the second member is movably disposed in the first member between a proximal position and a distal position relative thereto. The second member includes a guide having a distal end portion that is disposed in a distal position relative to the first member when the second member is in the distal position. The locking mechanism is configured to couple the introducer to a peripheral intravenous line. At least a portion of the actuator is disposed in the second member and is configured to move from a first configuration toward a second configuration to move the second member from its proximal position to its distal position. The actuator is configured to move relative to the second member to be placed in the second configuration when the second member is in its distal position. The catheter is disposed within the introducer when the actuator is in the first configuration and is disposed within and extending past an end of the peripheral intravenous line when in the actuator is in the second configuration.

BRIEF DESCRIPTION OF THE DRAWINGS

FIG. 77 is a flowchart illustrating a method of phlebotomy through a peripheral intravenous line, according to another embodiment.

FIGS. 78 and 79 are schematic illustrations of a distal end portion of a catheter according to different embodiments.

DETAILED DESCRIPTION

Figure 1:
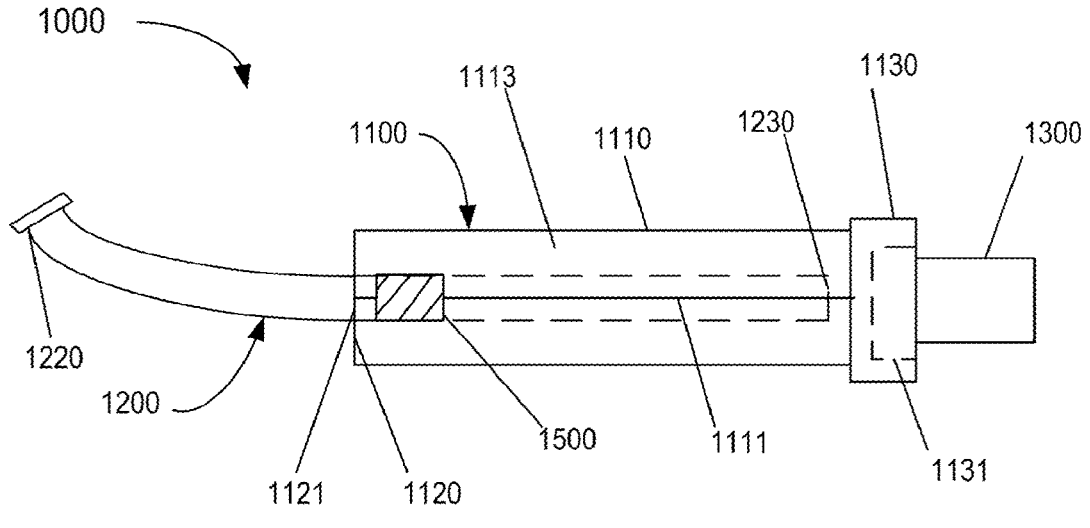
FIGS. 1 and 2 are schematic illustrations of an apparatus in a first configuration and a second configuration, respectively, according to an embodiment.

Systems and methods for phlebotomy through a peripheral intravenous catheter are described herein. In some embodiments, an apparatus includes a catheter having a proximal end portion and a distal end portion and defining a lumen therethrough, an introducer having a first member and a second member, a locking mechanism coupled to a distal end of the first member, and an actuator coupled to the catheter. At least a portion of the second member is movably disposed in the first member between a proximal position and a distal position relative thereto. The second member includes a guide having a distal end portion that is disposed in a distal position relative to the first member when the second member is in the distal position. The locking mechanism is configured to couple the introducer to a peripheral intravenous line. At least a portion of the actuator is disposed in the second member and is configured to move from a first configuration toward a second configuration to move the second member from its proximal position to its distal position. The actuator is configured to move relative to the second member to be placed in the second configuration when the second member is in its distal position. The catheter is disposed within the introducer when the actuator is in the first configuration and is disposed within and extending past an end of the peripheral intravenous line when in the actuator is in the second configuration.

In some embodiments, an apparatus includes a catheter, a first introducer, a second introducer, and an actuator. The catheter has a proximal end portion and a distal end portion and defining a lumen therethrough. The first introducer has a proximal end portion, a distal end portion, and an inner surface defining a channel. The distal end portion of the first introducer is configured to be coupled to a peripheral intravenous line. The second introducer has a proximal end portion and a distal end portion. The distal end portion of the second introducer includes a guide member. At least a portion of the second introducer is movably disposed in the first introducer such that a protrusion extending from an outer surface of the second introducer is disposed in the channel. The second introducer has a range of motion relative to the first introducer defined at least in part by the channel. The actuator is coupled to the catheter and is at least partially disposed in the second introducer. The actuator is configured to move the second introducer through at least a portion of the range of motion to advance a distal end portion of the guide member through the peripheral intravenous line. The actuator is configured to move from a first position relative to the second introducer, in which the catheter is disposed in the guide member, to a second position relative to the second introducer, in which the distal end portion of the catheter extends beyond a distal end of the guide member.

In some embodiments, a method includes coupling a fluid transfer device to a peripheral intravenous line. The fluid transfer device includes an introducer having a first member and second member. The second member includes a guide member and is movably disposed in the first member. The fluid transfer device includes an actuator movably disposed in the second member and a catheter coupled to the actuator. A first force is exerted on the actuator. The first force is sufficient to move the second member relative to the first member from a first position, in which the guide member is disposed in the first member, to a second position, in which a distal end portion of the guide member is inserted through a port of the peripheral intravenous line. A second force is exerted on the actuator. The second force is sufficient to move the actuator relative to the second member when the second member is in the second position to advance the catheter from a first position, in which the catheter is disposed in the introducer, to a second position, in which a distal end portion of the catheter extends past an end of the peripheral intravenous line. A fluid reservoir is coupled to the fluid transfer device such that the fluid reservoir is fluidically coupled to the catheter. The catheter is withdrawn from the peripheral intravenous line after a volume of bodily fluid is transferred to the fluid reservoir such that the catheter is disposed within the introducer.

In some embodiments, an apparatus includes a cannula or catheter, an introducer, a locking mechanism, and an actuator. The catheter includes a proximal end and a distal end and defines a lumen. The introducer includes a proximal end and a distal end and defines a lumen configured to receive at least a portion of the catheter. The locking mechanism is coupled to the distal end of the introducer and is configured to couple the introducer to a peripheral intravenous line. The actuator is operatively coupled to the catheter and is configured to move the catheter between a first configuration, in which the catheter is substantially within the introducer, and a second configuration, in which the catheter is substantially outside the introducer. The catheter extends past an end of the peripheral intravenous line when in the second configuration.

In some embodiments, a method includes coupling an introducer to a peripheral intravenous line (e.g., saline locked device, heparin locked device, or the like), the introducer having a proximal end and a distal end. The method further includes advancing a catheter from a first position inside the introducer and outside the peripheral intravenous line to a second position substantially outside the introducer and inside the peripheral intravenous line. In some embodiments, the catheter has a length greater than a length of the peripheral intravenous line, while in other embodiments, the catheter, in the second position, is shorter than the peripheral intravenous line. The method includes coupling a container to the proximal end of the introducer such that the container is fluidically coupled to the catheter. The method further includes withdrawing the catheter from the second position to the first position.

In some embodiments, a catheter has a proximal end and a distal end and defines a lumen therethrough. An introducer has a proximal end and a distal end and defines a lumen therethrough. The introducer is configured to receive the catheter therein. An adapter is coupled to the introducer. The adapter has a distal end configured to be coupled to a peripheral intravenous line. The adapter defines a first lumen and a second lumen. The first lumen has a first diameter and is configured to receive the catheter therethrough. The second lumen is orthogonal to the first lumen. An actuator is operatively coupled to the catheter and is configured to move the catheter between a first configuration and a second configuration. The catheter extends past the distal end of the adapter in the second configuration.

As used herein, the terms "catheter" and "cannula" are used interchangeably to describe an element configured to define a passageway for moving a bodily fluid from a first location to a second location (e.g., a fluid passageway to move a bodily fluid out of the body). While cannulas can be configured to receive a trocar, a guide wire, or an introducer to deliver the cannula to a volume inside the body of a patient, the cannulas referred to herein need not include or receive a trocar, guide wire, or introducer.

As used in this specification, the terms "Y-adapter" and "T-adapter" are used to refer to a dual port IV extension set. In this manner, the terms "Y-adapter" and "T-adapter" generally describe an overall shape of the dual port IV extension set. For example, as used herein, a Y-adapter is substantially "Y" shaped including a single port at a first end and two ports angularly disposed at a second end. Furthermore, the terms "Y-adapter" and "T-adapter" are included by way of example only and not limitation. For example, in some embodiments, an apparatus can include a single port IV extension set (e.g., a single port adapter) or a multi-port IV extension set (e.g., an adapter with more than two ports).

As used in this specification, the words "proximal" and "distal" refer to the direction closer to and away from, respectively, a user who would place the device into contact with a patient. Thus, for example, the end of a device first touching the body of the patient would be the distal end, while the opposite end of the device (e.g., the end of the device being manipulated by the user) would be the proximal end of the device.

As used herein, the term "stiffness" relates to an object's resistance to deflection, deformation, and/or displacement by an applied force. Stiffness can be characterized in terms of the amount of force applied to the object and the resulting distance through which a first portion of the object deflects, deforms, and/or displaces with respect to a second portion of the object. When characterizing the stiffness of an object, the deflected distance may be measured as the deflection of a portion of the object different from the portion of the object to which the force is directly applied. Said another way, in some objects, the point of deflection is distinct from the point where force is applied.

Stiffness is an extensive property of the object being described, and thus is dependent upon the material from which the object is formed as well as certain physical characteristics of the object (e.g., shape and boundary conditions). For example, the stiffness of an object can be increased or decreased by selectively including in the object a material having a desired modulus of elasticity, flexural modulus, and/or hardness. The modulus of elasticity is an intensive property of (i.e., is intrinsic to) the constituent material and describes an object's tendency to elastically (i.e., non-permanently) deform in response to an applied force. A material having a high modulus of elasticity will not deflect as much as a material having a low modulus of elasticity in the presence of an equally applied stress. Thus, the stiffness of the object can be increased, for example, by introducing into the object and/or constructing the object of a material having a high modulus of elasticity.

Similarly, a material's hardness is an intensive property of the constituent material and describes the measure of how resistant the material is to various kinds of permanent shape change when a force is applied. In discussing the hardness and the subsequent effect on the stiffness of a catheter, the Shore durometer scale is generally used. There are several scales for durometers with two commonly used in describing plastics, polymers, elastomers, and/or rubbers, namely, type A and type D, where type A is generally used for softer materials and type D is generally used for harder materials. The Shore durometer of a material is denoted by a number between 0 and 100, with higher numbers indicating a harder material, followed by the type of scale. For instance, a first material can be measured as having a Shore durometer of 40 Shore A and a second material can be measured as having a Shore durometer of 60 Shore D. Therefore, according to the Shore durometer scale, the second material is harder and thus, more stiff than the first material.

Figure 2:
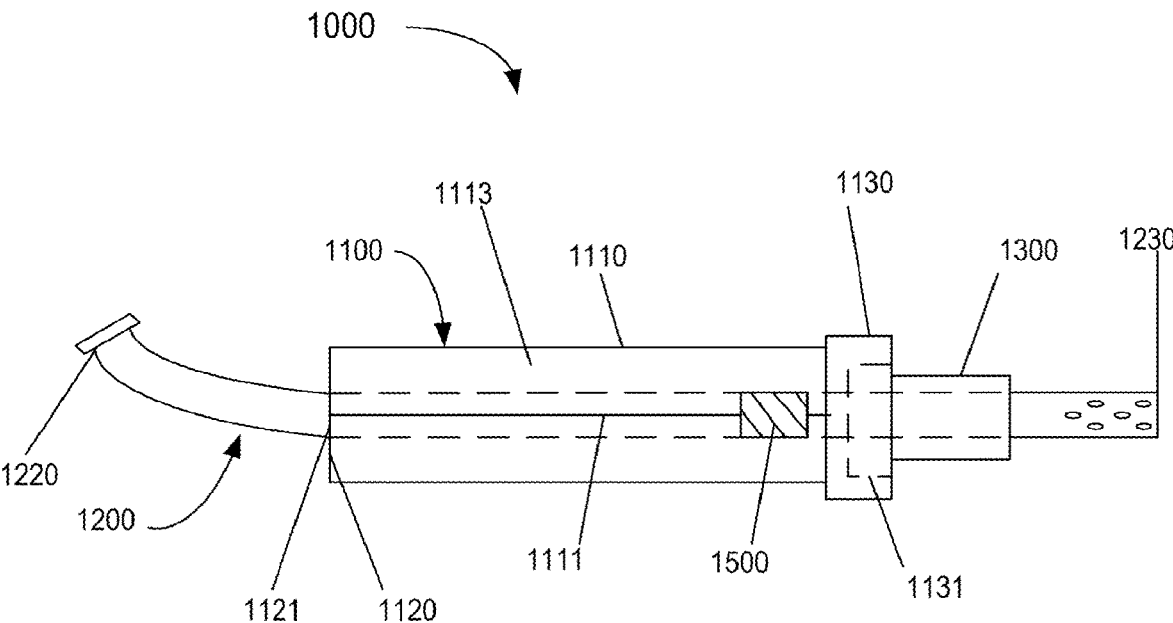

FIGS. 1 and 2 are schematic illustrations of an apparatus 1000 for phlebotomy through a peripheral intravenous line or catheter in a first configuration and second configuration, respectively, according to an embodiment. The apparatus 1000 includes an introducer 1100, a cannula or catheter 1200, a lock mechanism 1131, and an actuator 1500. The introducer 1100 includes a sheath 1110 having a proximal end 1120 and a distal end 1130 and defining a lumen 1113. The catheter/cannula 1200 is movably disposed within sheath 1110 between the proximal end 1120 and the distal end 1130.

The proximal end 1120 includes a port 1121, such that the catheter/cannula 1200 can move from the first, retracted configuration (FIG. 1) to the second, extended configuration (FIG. 2). Similarly stated, the port 1121 at the proximal end 1120 of the introducer 1100 is configured such that the catheter 1200 may move through the port 1121 from the first configuration to the second configuration. The port 1121 can be any suitable port such as, for example, an opening in the proximal end 1120 of the introducer 1100. Furthermore, the port 1121 can include any suitable seal member such as an O-ring or a gasket. In some embodiments, the port 1121 can be a self-sealing port and can be lubricated using any suitable lubrication to aid in the movement and/or sealing of the catheter 1200 therein.

The distal end 1130 of the introducer 1100 includes a locking mechanism 1131 configured to fluidically couple a peripheral intravenous line 1300 to the introducer 1100 and place the catheter 1200 into fluid communication with the peripheral intravenous line 1300. The locking mechanism 1131 can be any suitable locking mechanism that creates a fluid-tight seal. In some embodiments, the locking mechanism can be a Luer Lok™ or similar configuration. In some embodiments, the peripheral intravenous line 1300 is in a sealed configuration until the locking mechanism 1131 is coupled to the intravenous line 1300. Once the locking mechanism 1131 is coupled to the intravenous line 1300, the seal can be opened to allow access for the catheter 1200. In some embodiments, the locking mechanism can include a back flow prevention mechanism such as a one-way valve or the like. In this manner, the lock mechanism 1131 can be configured to allow the catheter 1200 to pass through the lock mechanism 1131 but substantially prevent a fluid flow, outside the catheter 1200, through the lock mechanism 1131.

The catheter 1200 defines a lumen 1201 between a proximal end 1220 and a distal end 1230 and may be any suitable diameter and stiffness. In some embodiments, the catheter 1200 can be between a 16-gauge and 26-gauge and have a Shore durometer of approximately 20 Shore A to 50 Shore D. In some embodiments, the catheter 1200 has a Shore durometer of approximately 20 Shore A to 95 Shore D. In some embodiments, the catheter 1200 has a Shore durometer of approximately 70 Shore D to 85 Shore D. In this manner, the catheter 1200 can be any suitable diameter to be inserted through the peripheral intravenous line 1300 and can be sufficiently stiff to be advanced through the peripheral intravenous line 1300.

The actuator 1500 is operatively coupled to the catheter 1200 through a groove or slot 1111 in the introducer 1100. The actuator 1500 is configured to move the catheter 1200 from the first configuration to the second configuration such that the distal end 1230 of the catheter 1200 is substantially outside the introducer 1100, as shown in FIG. 2. In some embodiments, the length of the distal end 1230 of the catheter 1200 is greater than the length of the peripheral intravenous line 1300. In this manner, the distal end 1230 of the catheter 1200 extends past the distal end of the intravenous line 1300.

In some embodiments, the catheter 1200 can be moved to a third configuration in which the catheter 1200 is retracted back into the introducer 1100. The third configuration can be substantially similar to the first configuration (FIG. 1) in that the catheter 1200 is positioned in the introducer 1100, thus, the user does not come into contact with bodily fluids. While in the first configuration and the third configuration, the apparatus 1000 can be disconnected from or connected to a peripheral intravenous line 1300. Said another way, the apparatus 1000 can be in the first configuration before it is coupled to the peripheral intravenous line 1300, then remain in the first configuration for a period of time after being coupled to the peripheral intravenous line 1300. Similarly, the apparatus 1000 can be moved to the third configuration, be disconnected from the peripheral intravenous line 1300, and then remain in the third configuration.

Figure 3:
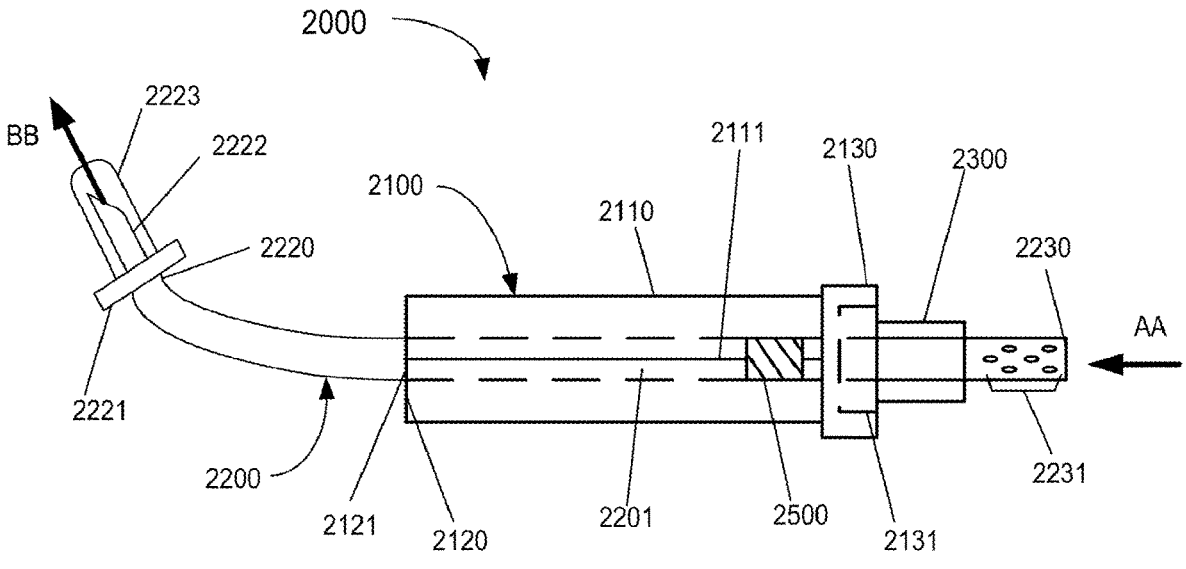
FIG. 3 is a detailed schematic illustration of an apparatus in a second configuration, according to an embodiment.

FIG. 3 is a detailed schematic illustration of an apparatus 2000 according to an embodiment in a second configuration. In some embodiments, the apparatus 2000 is substantially similar to the apparatus 1000 described above in reference to FIGS. 1 and 2. Therefore, aspects of the apparatus 2000 are not described in detail herein. The apparatus 2000 includes an introducer 2100 and a catheter 2200. The catheter 2200 includes a proximal end 2220 and a distal end 2230. The distal end 2230 of the catheter 2200 includes a set of openings 2231 such that when in the second configuration (e.g., when the distal end 2230 of the catheter 2200 is in the vein and outside the intravenous line) the openings 2231 act to transport a bodily fluid (e.g., blood) to a volume outside the catheter 2200. The set of openings 2231 can be of any arrangement on the circumference of the catheter 2200 and can include the end of the catheter 2200. Similarly stated, the catheter 2200 having the distal end 2230 can define an opening at the tip surface. Each opening 2231 can be of any suitable shape or size and are not necessarily similar to any other opening included in the set of openings 2231. In some embodiments, the catheter 2200 defines a single opening. For example, in some embodiments, the catheter 2200 defines a single opening 2231 at the distal surface.

The proximal end 2220 of the catheter 2200 is fluidically coupled to a locking mechanism 2221, as shown in FIG. 3. The locking mechanism 2221 can be any suitable locking mechanism such as a Luer Lok™ or the like. A needle 2222 is fluidically coupled to the locking mechanism 2221 and at least partially disposed within a sheath 2223. The sheath 2223 can be any material with a suitable flexibility and/or compressibility such that the needle 2222 can extend through the sheath 2223 when engaged with a conventional phlebotomy fluid container (e.g., a Vacutainer®). The locking mechanism 2221 is configured to be coupled to any suitable fluid containment system such as a Vacutainer® holder (not shown in FIG. 3) and place the needle 2222 in fluid communication with the fluid containment system. The sheath 2223 is configured to compress when the locking mechanism 2221 is coupled to the fluid containment system. This arrangement facilitates the passage of bodily fluids through the set of openings 2231 of the catheter 2200, as shown in FIG. 3 by arrow AA, through the catheter 2200, and exiting the catheter 2200 through the needle 2222, as shown in FIG. 3 by arrow BB.

Figure 4:
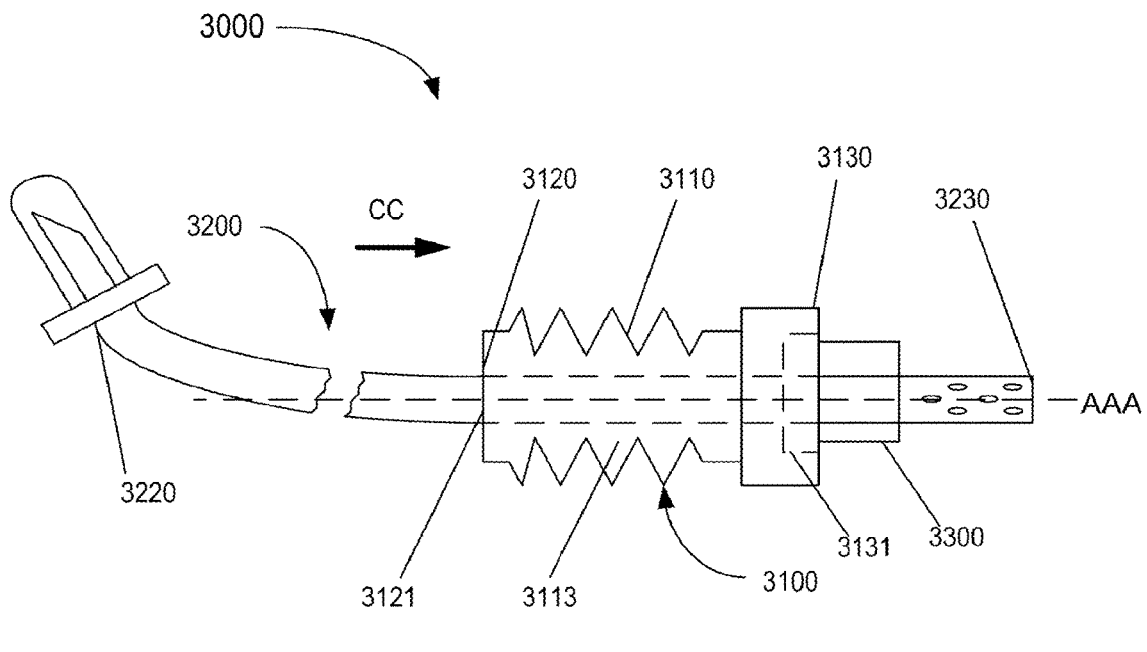
FIG. 4 is a detailed schematic illustration of an apparatus in a second configuration, according to an embodiment.

FIG. 4 is a schematic illustration of an apparatus 3000 for phlebotomy through a peripheral intravenous catheter in a second configuration according to an embodiment. The apparatus 3000 includes an introducer 3100 and a catheter 3200. The introducer 3100 includes a sheath 3110 defining a lumen 3113 between a proximal end 3120 and a distal end 3130 and configured to house, at least partially, the catheter 3200. The distal end 3130 of the introducer 3100 includes a locking mechanism 3131 configured to fluidically couple the introducer 3100 to a peripheral intravenous line 3300 and place the catheter 3200 into fluid communication with the peripheral intravenous line 3300, when the catheter 3200 is in the second configuration. The locking mechanism 3131 can be any suitable locking mechanism that creates a fluid-tight seal. In some embodiments, the locking mechanism 3131 can be a Luer Lok™ or similar configuration. The sheath 3110, having a given stiffness, is configured such that when applying a force to the proximal end 3120 (as indicated by the arrow CC in FIG. 4), the sheath 3110 compresses along an axis AAA.

The compression of the sheath 3110 is such that the catheter 3200 is advanced to the second configuration. Said another way, as the sheath 3110 of the introducer 3100 is compressed, the catheter 3200 moves from a first configuration where in the catheter 3200 is disposed within the introducer 3100 (as described above with respect to FIG. 1) to a second configuration wherein the distal end 3230 is substantially outside the introducer 3100, as shown in FIG. 4. Furthermore, the stiffness of the sheath 3110 is an extensive property and as such can have a set of properties (i.e. material, thickness, shape and/or the like) to allow the sheath 3110 to compress along the axis AAA with the desired amount of force applied at the proximal end 3120 of the introducer 3100. The set of properties allow the sheath 3110 to elastically deform (i.e. non-permanently) such that when the force is no longer applied to the proximal end 3120 of the introducer 3100, the apparatus 3000 returns to the first configuration. In the second configuration, the distal end 3230 of the catheter 3200 extends past the distal end of the peripheral intravenous line 3300. This arrangement allows for the transport of a bodily fluid to a volume outside the catheter 3200 and when complete, the apparatus 3000 can be placed in a third configuration, substantially similar to the first configuration.

Figures 5, 6:
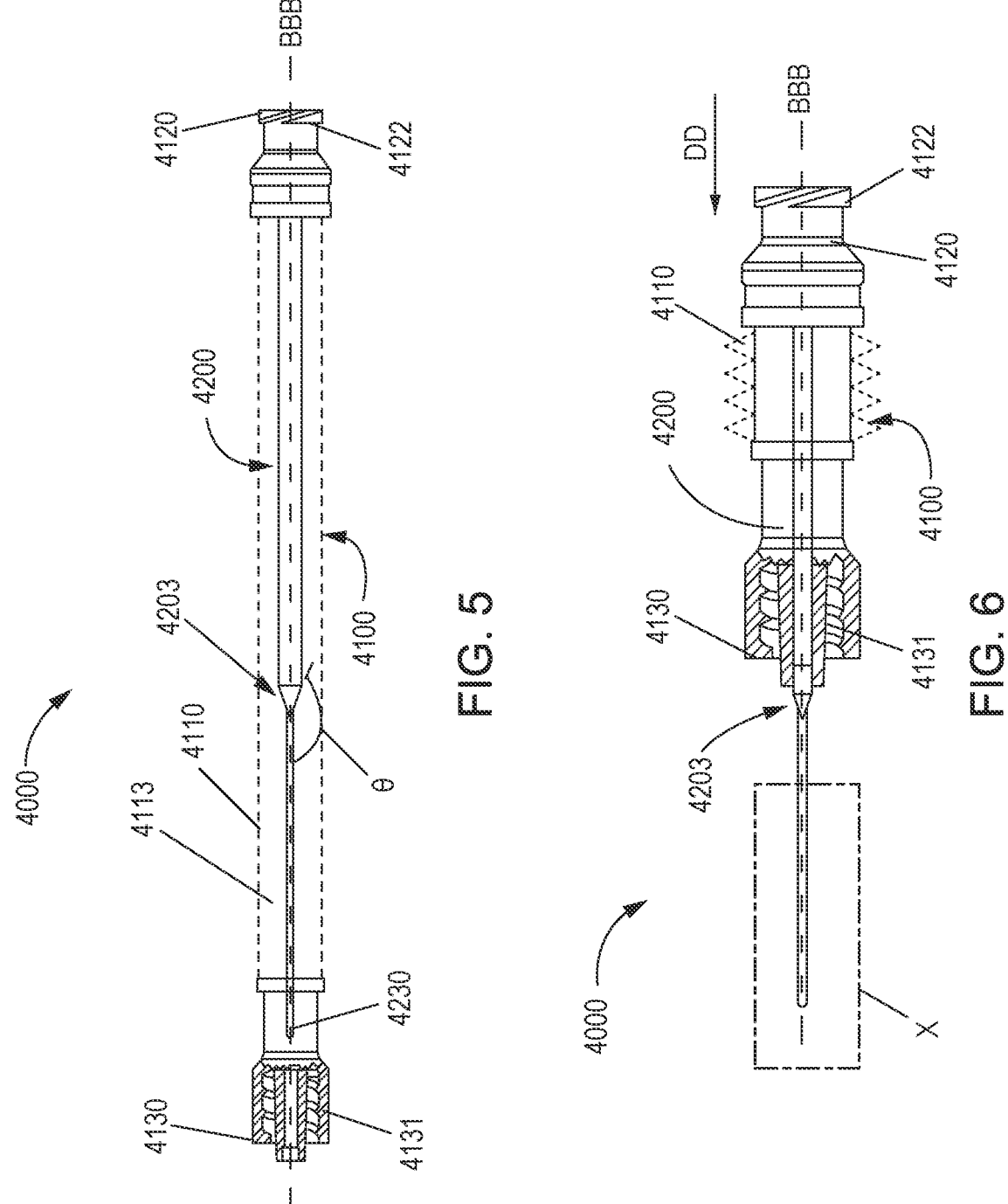
FIGS. 5 and 6 are cross-sectional side views of an apparatus in a first configuration and a second configuration, respectively, according to an embodiment.

FIGS. 5 and 6 are side views of an apparatus 4000 according to an embodiment in a first configuration and a second configuration, respectively. The apparatus 4000 includes an introducer 4100 and a catheter 4200. The introducer 4100 includes a sheath 4110 defining a lumen 4113 between a proximal end 4120 and a distal end 4130 and is configured to house, at least partially, the catheter 4200. Although shown in FIG. 5 as being cylindrical, the introducer 4100 can be any suitable shape. Moreover, the lumen 4113, defined by the interior walls of the sheath 4110 is not necessarily the same shape as the exterior walls of the sheath 4110. Said a different way, the interior and exterior walls of the sheath 4110 can have a different cross sectional shape. The proximal end 4120 of the introducer 4100 is coupled to a locking mechanism 4122. The locking mechanism 4122 can be any suitable locking mechanism such as a Luer Lok™ or the like. In use, the locking mechanism 4122 is configured to couple to a suitable fluid containment system such as a Vacutainer® holder (not shown in FIG. 5) to place the catheter 4200 in fluid communication with the fluid containment system.

The distal end 4130 of the introducer 4100 includes a locking mechanism 4131 configured to fluidically couple the introducer 4100 to a peripheral intravenous line (not shown in FIG. 5). In this manner, the locking mechanism 4131 can be configured to selectively place the catheter 4200 into fluid communication with the peripheral intravenous line. The locking mechanism 4131 can be any suitable locking mechanism that creates a fluid-tight seal. In some embodiments, the locking mechanism 4131 is in a sealed configuration until the locking mechanism 4131 is coupled to the intravenous line. Once the locking mechanism 4131 is coupled to the intravenous line, the seal can be opened to allow access for the catheter 4200. In addition, while in the unlocked configuration, the locking mechanism 4131 of the distal end 4130 and the locking mechanism 4122 of the proximal end 4120 create a fluidically isolated housing for the catheter 4200 therein. Stated similarly, prior to the proximal end locking mechanism 4122 and distal end locking mechanism 4131 being unlocked and before the catheter 4200 is in the second configuration, the catheter 4200 is sterile. Furthermore, the catheter 4200, when in the second configuration and having contacted the desired bodily fluid, can be moved to a third configuration (e.g., substantially similar to the first configuration) thereby isolating the used distal end 4230.

The sheath 4110 has a given stiffness such that when a force (as indicated by the arrow DD in FIG. 6) is applied to the proximal end 4120, the sheath 4110 compresses along an axis BBB. The compression of the sheath 4110 is such that the catheter 4200 is advanced to the second configuration. Said another way, as the sheath 4110 of the introducer 4100 is compressed, the catheter 4200 moves from the first configuration wherein the catheter 4200 is disposed within the introducer 4100 to the second configuration wherein the distal end 4230 is substantially outside the introducer 4100 (e.g., the sheath 4110 retracts). The properties of the sheath 4110 can be any set of properties discussed herein such that applying a desired amount of force to proximal end 4120 allows the sheath to compress along axis BBB. In the second configuration, the distal end 4230 of the catheter 4200 extends past the distal end of the peripheral intravenous line and allows for the transport of a bodily fluid to a volume outside of the catheter 4200.

Figure 6A:
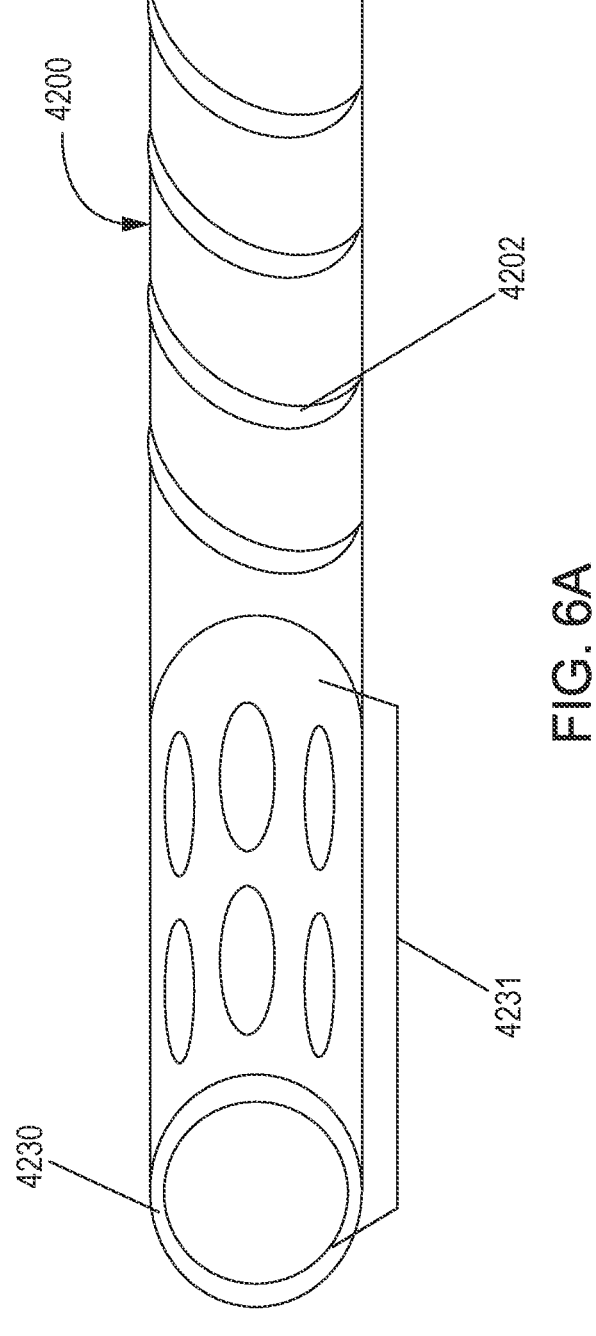
FIG. 6A is an enlarged view of a portion of the apparatus of FIG. 6, indicated by the region X.

The catheter 4200 includes a distal end 4230 and tapered portion 4203. The tapered portion is such that the diameter of the catheter 4200 is reduced at a given location, as shown in FIG. 5. The taper angle θ can be any suitable angle such that the catheter 4200 is allowed to advance fully to the second configuration (FIG. 6). Moreover, the taper angle θ is such that a laminar flow (i.e., smooth layered flow) is achieved. In some embodiments, the catheter 4200 can include a stiffening wire 4202, as shown in FIG. 6A, and can be configured to coil around the walls of the catheter 4200 providing the catheter 4200 with a desired stiffness. More-over, the stiffening wire 4202, being coiled around the catheter 4200, can provide the flexibility to advance through a set of walls defining a lumen (i.e., veins, arteries, periph-eral intravenous line, and/or the like) without kinking or binding. In addition, the stiffening wire 4202 can provide the catheter 4200 with enough stiffness to facilitate its advance-ment through the lumen.

The distal end 4230 of the catheter 4200 includes a set of openings 4231 such that when in the second configuration (e.g., when the distal end 4230 of the catheter 4200 is in the vein and outside the intravenous line) the openings 4231 act to transport a bodily fluid (i.e., blood) to a volume outside the catheter 4200. The set of openings 4231 can be of any arrangement on the circumference of the catheter 4200 and can include the end of the catheter 4200. Similarly stated, the catheter 4200 having the distal end 4230 can be substantially open at the tip surface. Although FIGS. 6 and 6A show the distal end 4230 of the catheter 4200 as substantially flat, the distal end 4230 may be any suitable shape, (e.g. conical or spherical) and can have any suitable degree of rounded edges. Each opening 4231 can be of any suitable shape or size and are not necessarily similar to any other opening 4231 included in the set of openings 4231. The arrangement of the set of openings 4231 is configured to introduce a laminar flow through catheter 4200 to a volume substantially outside the catheter 4200 and thus avoid hemolysis.

In some embodiments, a blood collection system consists of two elements: (1) the introducer/catheter blood collection assembly described above; and (2) a y-adapter that is configured to attach to a standard 16g or 22g peripheral IV catheter. The y-adapter includes a dedicated port for the blood collection device and another standard port for con-ventional medicine and fluid infusion.

Figure 7:
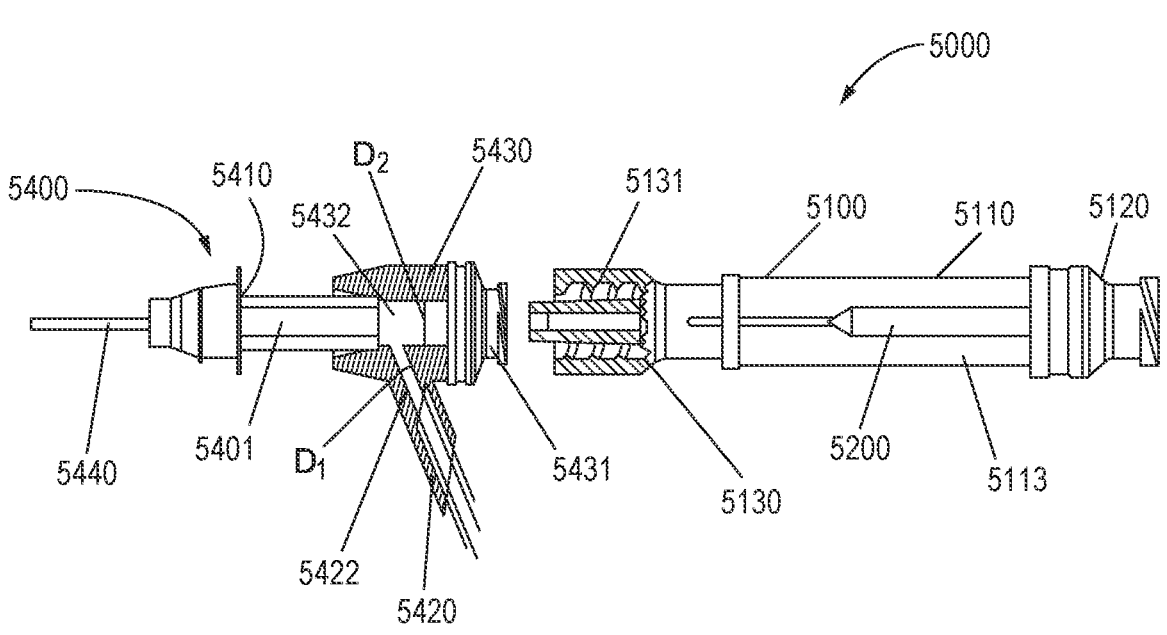
FIGS. 7 and 8 are cross-sectional side views of an apparatus and an adapter in a first configuration and a second configuration, respectively, according to an embodiment.

For example, FIG. 7 includes a cross-sectional view of a y-adapter 5400 and an apparatus 5000 in a first configura-tion, according to an embodiment. The apparatus 5000 includes an introducer 5100 and a catheter 5200. The introducer 5100 includes a sheath 5110 defining a lumen

5113 between a proximal end 5120 and a distal end 5130 and configured to house, at least partially, the catheter 5200. The catheter 5200 includes a proximal end 5220 and a distal end 5230. The apparatus 5000 can be substantially similar to the apparatus 4000 described above with reference to FIGS. 5 and 6. Therefore, aspects of the apparatus 5000 are not described in further detail herein.

In some embodiments, the y-adapter 5400 is configured to be coupled between the introducer 5100 and intravenous line 5440. The y-adapter includes a distal end 5410 and defines a first port 5420 and a second port 5430. The first port 5420 of the y-adapter 5400 defines a first lumen 5422 with a first diameter $D_1$. The first port 5420 is configured such that the first port 5420 is substantially similar in size, shape, con-figuration, and functionality of a conventional y-adapter. Moreover, the first port 5420 is configured such that the backflow of a bodily fluid cannot exit the first port 5420. More specifically, the first lumen 5422 defined by the walls of the first port 5420 can be such that the lumen 5422 restricts the backflow of a bodily fluid (i.e. blood). In some embodiments, the backflow can be prevented using a valve, screw cap, flip cap, port, and/or the like.

The second port 5430 of the y-adapter 5400 defines a second lumen 5432 with a second diameter $D_2$. As shown in FIG. 7, the second diameter $D_2$ can be configured to be larger than first diameter $D_1$. In other embodiments, the second diameter $D_2$ can be similar or smaller than the first diameter $D_1$. More particularly, the diameter $D_2$ of the second port 5430 is large enough to accept up to, for example, an 18-gauge catheter. The y-adapter 5400 can be of any suitable material and/or be of similar material to that of a conventional y-adapter.

The first lumen 5422 defined by the first port 5420 and the second lumen 5432 defined by the second port 5430 con-verge to a common lumen 5401 before the distal end 5410 of the y-adapter 5400, as shown in FIG. 7. The second port 5430 is configured such that the second lumen 5432 is substantially coaxial with the common lumen 5401. Fur-thermore, the common lumen 5401 can have a diameter substantially similar to the diameter $D_2$ of the second port 5430.

The second port 5430 is fluidically coupled to a locking mechanism 5431 configured to couple the y-adapter to the introducer 5100. The locking mechanism 5431 can be a Luer Lok™ or the like. In some embodiments, the y-adapter 5400 is in a sealed configuration until coupled to the locking mechanism 5131 at the distal end 5130 of the introducer 5100. Once the locking mechanism 5431 is coupled to the introducer 5100, the seal can be opened to allow access for the catheter 5200 to advance to a second configuration, shown in FIG. 8 (note the introducer 5100 is not shown coupled to the y-adapter in FIG. 8).

In some embodiments, the distal end 5410 of the y-adapter 5400 is coupled to a peripheral intravenous line 5440 such as, for example, a conventional peripheral intra-venous line. In some embodiments, the y-adapter 5400 is monolithically formed with the peripheral intravenous line 5440. In some embodiments, the distal end 5410 of the y-adapter 5400 can be coupled to a peripheral intravenous line using any suitable locking mechanism. Similarly, the second port 5420 of the locking mechanism 5431 configured to couple the y-adapter 5400 to the introducer 5100 can monolithically formed with the introducer 5100. Said another way, in some embodiments, a separate introducer is not required, but rather a portion of the y-adapter can serve as the introducer.

Figure 8:
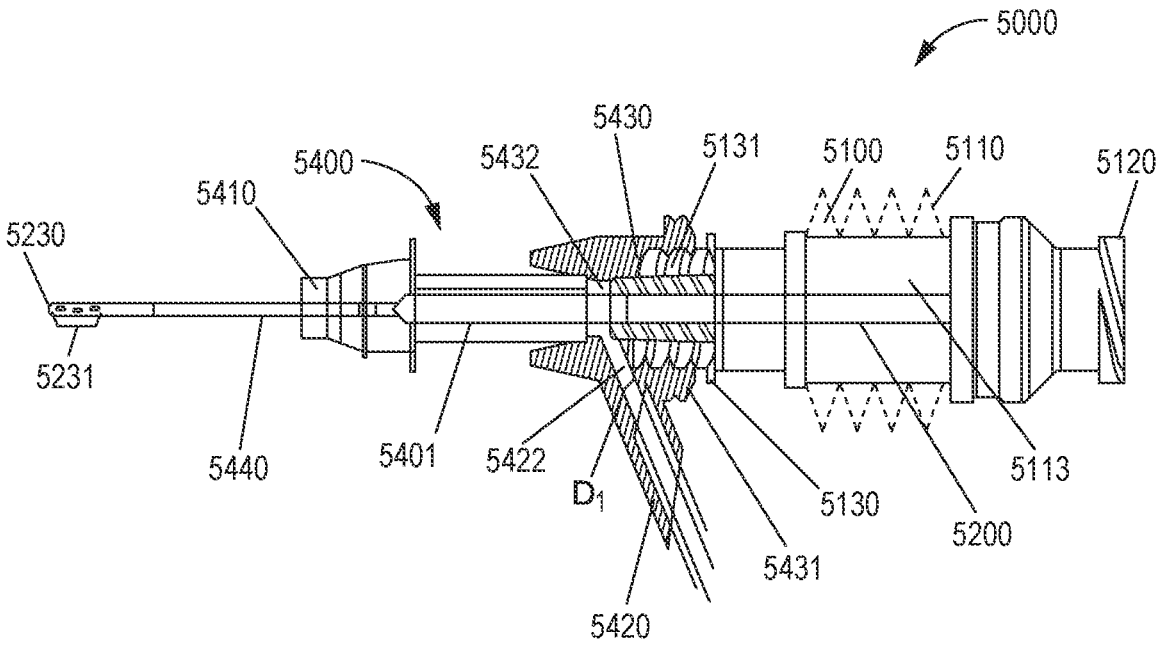
Figure 9:
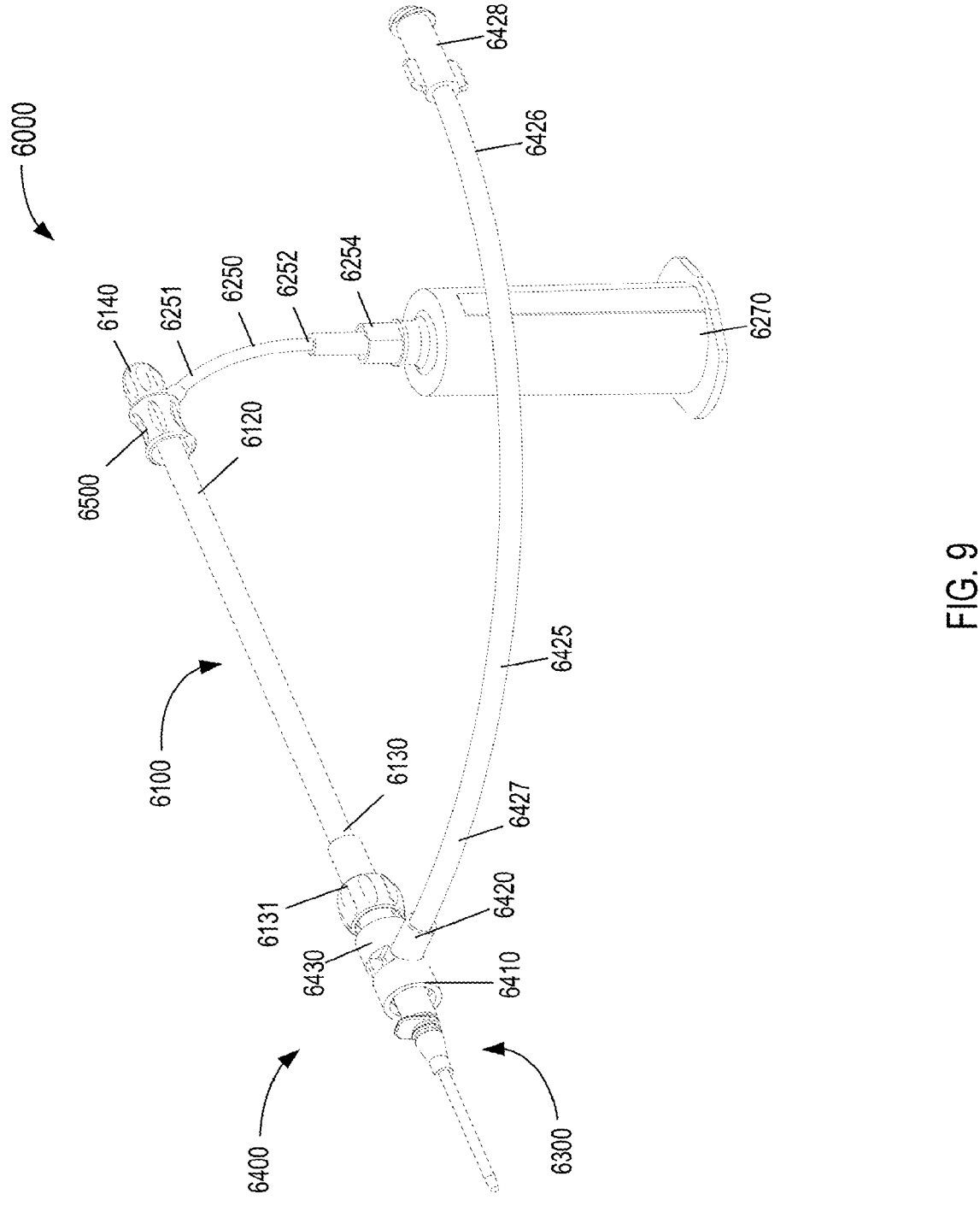
FIG. 9 is a perspective view of an apparatus in a first configuration, according to an embodiment.

When in the second configuration as shown in FIG. 8, the distal end 5230 of the catheter 5200 is advanced substantially past the peripheral intravenous line 5440. The distal end 5230 of the catheter 5200 includes a set of openings 5231 such that when in the second configuration (i.e., when the distal end 5230 of the catheter 5200 is in the vein and outside the intravenous line) the openings 5231 act to transport a bodily fluid (i.e., blood) to a volume outside the catheter 5200. The set of openings 5231 can be of any arrangement on the circumference of the catheter 5200 and can include the end of the catheter 5200. Similarly stated, the catheter 5200 having the distal end 5230 can be substantially open at the tip surface. Each opening 5231 can be of any suitable shape or size and are not necessarily similar to any other opening included in the set of openings. The catheter 5200, in the second configuration and having transported the desired bodily fluid, can be placed in a third configuration (e.g., substantially similar to the first configuration shown in FIG. 7), thereby isolating the used distal end 5230.

While the introducer 5100 (FIGS. 7 and 8) is described as being configured to be substantially compressed to advance the catheter 5200, in other embodiments, an apparatus can include an actuator configured to move the catheter relative to the introducer. For example, FIGS. 9-14 illustrate an apparatus 6000 used for phlebotomy through a peripheral intravenous line. The apparatus 6000 includes an introducer 6100, a cannula 6200, and an adapter 6400. The apparatus 6000 can be any suitable shape, size, or configuration and is configured to be coupled to, for example, a peripheral intravenous line (PIV) 6300.

The introducer 6100 includes a proximal end 6120 and a distal end 6130. As shown in FIGS. 9-14, the introducer 6100 is a substantially cylindrical tube configured to receive the cannula 6200. Similarly stated, the introducer 6100 includes a wall or set of walls that define a lumen 6113 (FIG. 11) configured to selectively receive the cannula 6200. The introducer 6100 and cannula 6200 can be formed from any suitable material having any given durometer. In some embodiments, the cannula 6200 can have a durometer between 20 Shore A and 50 Shore D. In other embodiments, the cannula 6200 can have a Shore durometer of approximately 20 Shore A to 95 Shore D. In still other embodiments, the cannula 6200 can have a Shore durometer of approximately 70 Shore D to 85 Shore D.

The proximal end 6120 of the introducer 6100 is configured to be coupled to an end cap 6140. In this manner, the end cap 6140 can be configured to substantially close off and/or seal the proximal end 6120 of the introducer 6100. In some embodiments, the end cap 6140 is configured to form a substantially fluid-tight seal with the introducer 6100. Similarly stated, in some embodiments, the end cap 6140 and the proximal end 6120 of the introducer 6100 define a substantially hermetic seal. In some embodiments, the end cap 6140 can be grasped by a user as the cannula 6200 is advanced.

The distal end 6130 of the introducer 6100 is coupled to a lock mechanism 6131. The lock mechanism 6131 is configured to physically and fluidically couple a portion of the apparatus 6000 to the existing PIV 6300. In some embodiments, the lock mechanism 6131 can be configured to be directly coupled to the existing PIV 6300. In other embodiments, the lock mechanism 6131 can be coupled to the adapter 6400 and/or any other suitable intervening structure, such as, for example, a known valve or cap.

The distal end 6130 of the introducer 6100 can be coupled to the lock mechanism 6131 in any suitable manner. For example, in some embodiments, the distal end 6130 can be disposed within a portion of the lock mechanism 6131 such that an outer surface of the introducer 6100 defines a friction fit with the inner surface of the portion of the lock mechanism 6131. In other embodiments, the distal end 6130 of the introducer 6100 can be coupled to the lock mechanism 6131 via an adhesive. In still other embodiments, the lock mechanism 6131 can be monolithically formed with the distal end 6130 of the introducer 6100. For example, in some embodiments, the lock mechanism 6131 can be formed from a similar material as the introducer 6100. In other embodiments, the introducer 6100 can be formed from a first material and the lock mechanism 6131 can be formed from a second material configured to be over-molded the distal end 6130 during a manufacturing process.

Figure 11:
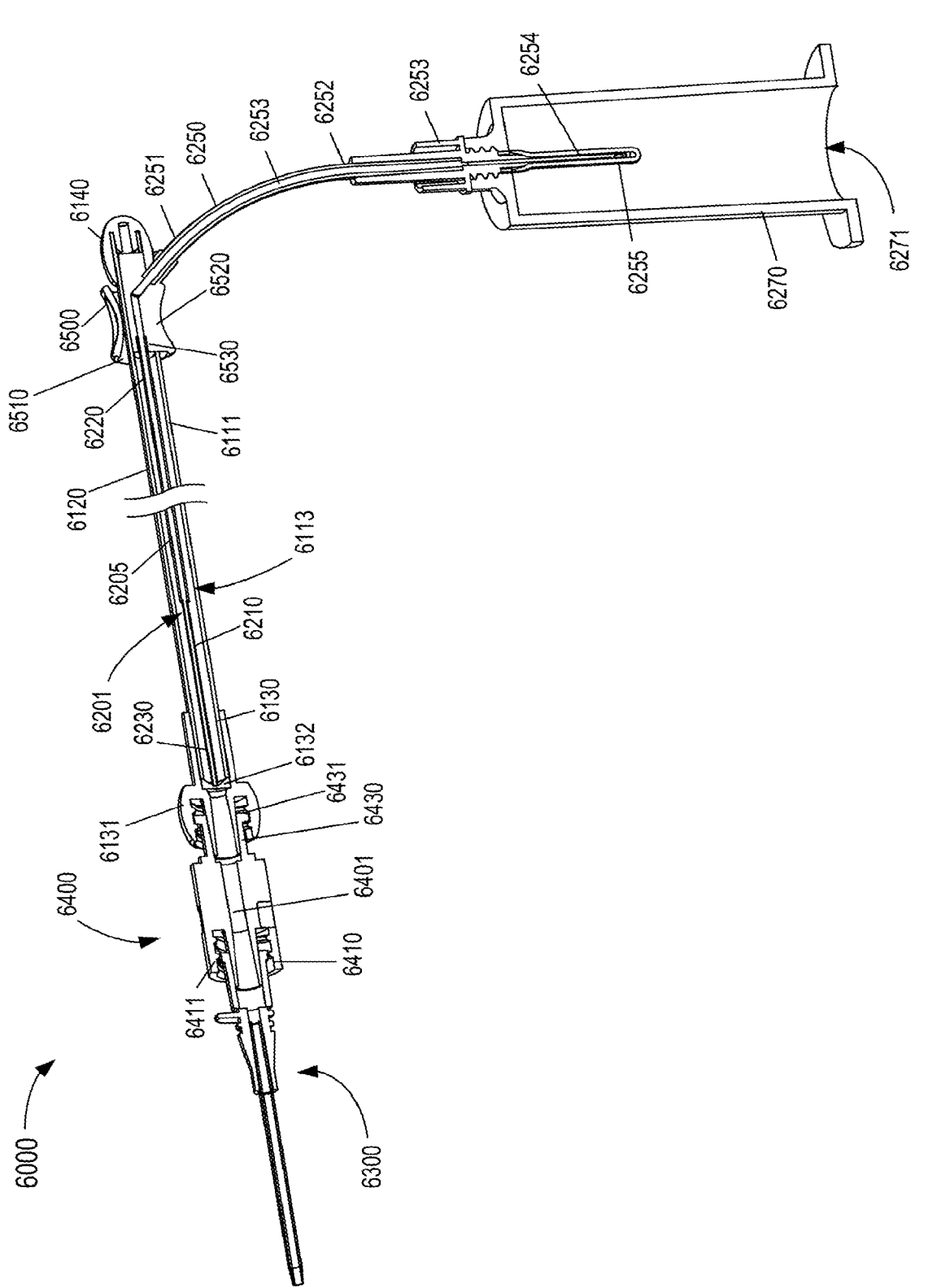
FIG. 11 is a cross-sectional perspective view of the apparatus illustrated in FIG. 9.

As seen in FIG. 11, the lock mechanism 6131, includes a seal member 6132 configured to define a substantially fluid tight seal when the cannula 6200 is in the first configuration. Furthermore, in use, the seal member 6132 can be configured to receive a portion of the cannula 6200 to allow the cannula 6200 to advance, in the distal direction, beyond the seal member 6132. In this manner, the seal member 6132 can form a substantially fluid tight seal around the cannula 6200 such that the seal member 6132 substantially prevents a backflow into the introducer 6100. The seal member 6132 can be any suitable configuration such as, for example, an O-ring, a one-way valve, a diaphragm, a check valve, or any other suitable seal member. While shown and described as being included in the locking mechanism 6131, in some embodiments, a seal member can be included in the locking mechanism 6131 and/or the adapter 6400. For example, in some embodiments, the locking mechanism 6131 can be coupled to the adapter 6400 such that the seal member included in the adapter 6400 and/or the locking mechanism 6131 prevents a flow of bodily fluid in the proximal direction prior to advancing the cannula 6200, as further described herein.

Figure 10:
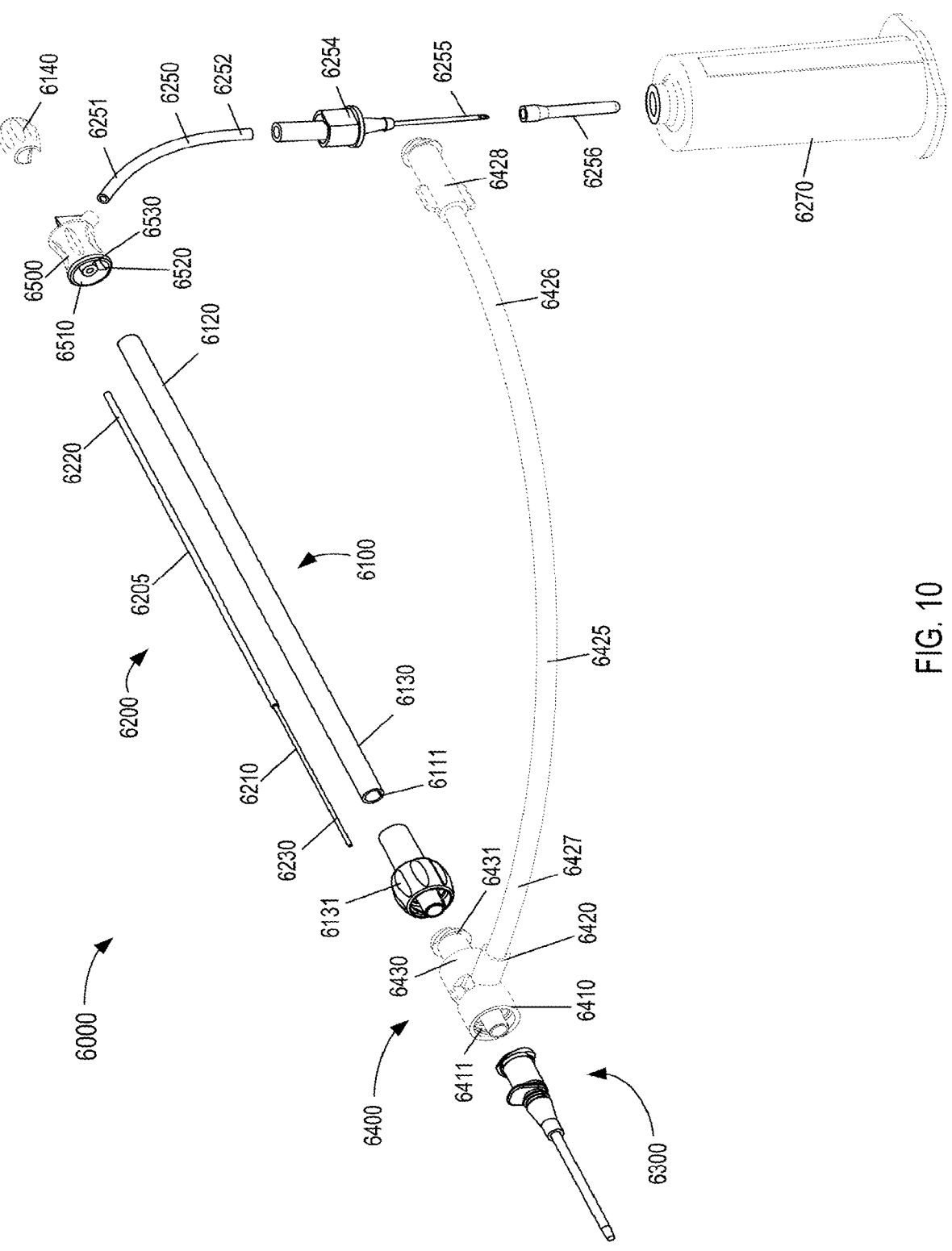
FIG. 10 is an exploded view of the apparatus illustrated in FIG. 9.

As seen in FIGS. 10 and 11, the introducer 6100 further defines an actuator track 6111. The actuator track 6111 can be a slit or opening defined by the wall of the introducer 6100 and is configured to receive a portion of the actuator 6500. The actuator track 6111 can be configured to extend substantially along the length of the introducer 6100. In some embodiments, the actuator track 6111 is configured to continuously extend through the distal end 6130 and the proximal end 6120 of the introducer 6100. The actuator track 6111 can be any suitable configuration and can engage the portion of the actuator 6500 in any suitable manner. For example, in some embodiments, the walls of the introducer 6100 defining the actuator track 6111 can form a friction fit with the portion of the actuator 6500, as described in further detail herein.

The cannula 6200 defines a lumen 6201 (FIG. 11) and is configured to be movably disposed within the introducer 6100. As described above with reference to FIG. 5, the cannula 6200 can be configured to include a first portion 6205 having a first diameter and a second portion 6210 having a second diameter, smaller than the first. More specifically, the first portion 6205 is disposed at a proximal end 6220 of the cannula 6200 and the second portion 6210 is disposed at a distal end 6230 of the cannula 6200. In this manner, for example, the diameter of the cannula 6200 is reduced at the distal end 6230 of the catheter 6200 to facilitate the insertion of the catheter 6200 into the peripheral intravenous line, as described in further detail herein.

As described above with reference to FIG. 6A, the distal end 6230 of the cannula 6200 can be configured to include any suitable number of openings (not shown in FIGS. 9-14.

For example, in some embodiments, the distal end 6230 of the cannula 6200 can include a substantially open end-surface configured to place the lumen 6201 in fluid communication with, for example, a vein. In some embodiments, the end surface can be substantially flat (e.g., perpendicular to a longitudinal axis of the cannula 6200. In other embodiments, the end surface can be any suitable configuration such as, for example, substantially bullet-shaped, conical, bulbous, or the like. In still other embodiments, the end surface can be substantially angled with respect to the longitudinal axis of the cannula 6200 (e.g., similar to the tip of a needle). Furthermore, in some embodiments, the distal end 6230 can be configured to include the open end-surface and an opening disposed on the side of the cannula 6200. In this manner, the side opening (not shown in FIGS. 9-14) can be configured to transfer a portion of a bodily fluid even if the opening disposed at the end surface is obstructed (e.g., by a clot or the like).

The actuator 6500 is coupled to the proximal end 6220 of the cannula 6200 and is configured to move the cannula 6200, relative to the introducer 6100, between a first configuration and a second configuration. More specifically, the actuator 6500 defines a substantially annular shape defining a cavity 6510 configured to receive the proximal end 6120 of the introducer 6100 and the proximal end 6220 of the cannula 6200. Similarly stated, the actuator 6500 is disposed about the introducer 6100 and the cannula 6200. Furthermore, the actuator 6500 is configured such that a guide member 6520 and a coupler 6530 extend from an inner surface of the actuator 6500.

The guide member 6520 can be any suitable shape, size, or configuration. For example, as shown in FIG. 10, the guide member 6520 is a relatively thin extension. In this manner, the guide member 6520 is disposed within the actuator track 6111 when the actuator 6500 is disposed about the introducer 6100. In some embodiments, the walls of the introducer 6100 defining the actuator track 6111 define a friction fit with a portion of the guide member 6520. The arrangement of the guide member 6520 within the actuator track 6111 can be such that the actuator 6500 is substantially maintained in a given location, relative to the introducer 6100, until a force is applied to the actuator 6500 to move the actuator 6500 towards the second configuration. Similarly stated, the actuator 6500 engages the introducer 6100 such that the actuator 6500 substantially does not move without a user's intervention (e.g., applying a force to the actuator 6500). In other embodiments, the actuator 6500 need not include a guide member 6520. In such embodiments, the actuator 6500 can be configured to define a friction fit with the introducer 6100 when the actuator 6500 is disposed about the introducer 6100 (e.g., an inner surface of the wall or walls defining the annular shape of the actuator 6500 engage an outer surface of the introducer 6100 to define the friction fit).

Figures 13, 13A:
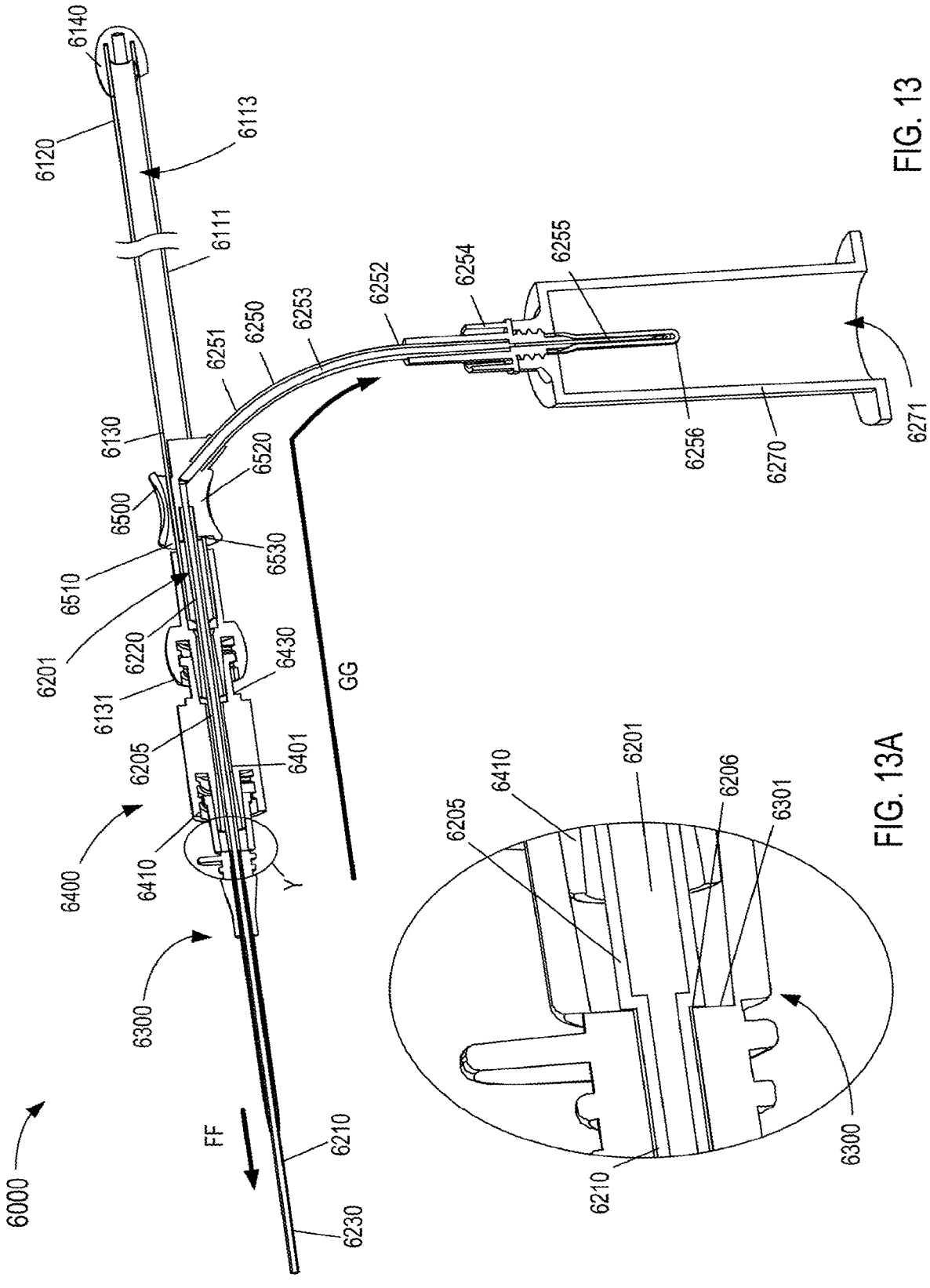
FIG. 13 is a cross-sectional perspective view of the apparatus illustrated in FIG. 9, in the second configuration.
FIG. 13A is an enlarged view of a portion of the apparatus of FIG. 13, indicated by the region Y.

The coupler 6530 is disposed on a top surface of the guide member 6520 (e.g., the guide member 6520 is disposed between the coupler 6530 and the inner surface of the actuator 6500). As shown in FIGS. 11 and 13, the coupler 6530 is coupled to the proximal end 6220 of the cannula 6200. In some embodiments, an outer surface of the proximal end 6220 of the cannula 6200 defines a friction fit with the inner surface of the coupler 6530. In other embodiments, the distal end 6220 of the cannula 6200 can be coupled to the coupler 6530 via an adhesive. In this manner, the proximal end 6220 of the cannula 6200 and the coupler 6530 form a substantially fluid tight seal.

A proximal end 6540 of the actuator 6500 is coupled to a secondary cannula 6250 further configured to be coupled to a container shroud 6270. The container shroud 6270 defines a cavity 6271 configured to receive fluid reservoir (e.g., a conventional phlebotomy fluid container such as a Vacutainer®). More specifically, secondary cannula 6250 defines a lumen 6253 and includes a proximal end 6252 configured to be coupled to a lock mechanism 6524. The lock mechanism 6524 can be configured to be coupled to the container shroud 6270. In addition, the lock mechanism 6524 includes a needle 6525 disposed within a sheath 6526 configured to pierce a portion of the fluid reservoir (e.g., as described above with reference to FIG. 3) when the fluid reservoir (not shown) is disposed within the container shroud 6270. Therefore, with the proximal end 6220 of the cannula 6200 coupled to the coupler 6530 and the secondary cannula 6250 coupled to the proximal end 6540 of the adapter 6500, the adapter 6500 is configured to place the cannula 6200 (e.g., the lumen 6201 defined by the cannula 6200) in fluid communication with the secondary cannula 6250 (e.g., the lumen 6253 of the secondary cannula 6250) and the fluid reservoir (not shown).

While described as including the secondary cannula 6250, in some embodiments, the apparatus 6000 need not include the secondary cannula 6250. In such embodiments, the cannula 6200 can define a continuous fluid path (e.g., lumen 6201) from the distal end 6230, through the connector 6530, and to the container shroud 6270. In other embodiments, the container shroud 6270 can be configured to be physically and fluidically coupled to the actuator 6500.

The adapter 6400 can be any suitable adapter 6400. For example, in some embodiments, an adapter can be a known Y-adapter or T-adapter (e.g., a dual port IV extension set). In other embodiments, an adapter can be similar in form and function to the adapter 5400, described above with reference to FIGS. 7 and 8. As shown in FIG. 10, the adapter 6400 is a T-style adapter and includes a distal end 6410, a first port 6420, and a second port 6430. The distal end 6410 defines a port and includes a lock mechanism 6411 configured to be coupled to the peripheral intravenous line 6300. In this manner, the lock mechanism 6411 can be any suitable known lock mechanism such that the distal end 6410 of the adapter 6400 can engage a known PIV 6300.

The first port 6420 can be coupled to a distal end 6427 of an inlet catheter 6425. In some embodiments, the distal end 6427 of the inlet catheter 6425 forms a friction fit with an inner surface of the first port 6420. In some embodiments, the distal end 6427 of the inlet catheter 6425 can include a fitting configured to engage the first port 6420 (e.g., a threaded fitting). In other embodiments, the inlet catheter 6425 can be monolithically formed with the first port 6420 of the adapter 6400. The inlet catheter 6425 further includes a proximal end 6426 configured to couple to a lock mechanism 6428. In this manner, the inlet catheter 6425 can be engaged by a user (e.g., a physician, nurse, or the like) to administer a fluid (e.g., a medicine or the like) to the peripheral intravenous line and thus, the vein of a patient. In some embodiments, the inlet catheter 6425 is substantially similar in form and function as known inlet catheters. Therefore, with the adapter 6400 coupled to the PIV 6300 and the PIV 6300 disposed within a patient, a user can administer a given fluid to the patient via the inlet catheter 6425 without requiring further training in the functioning of the adapter 6400.

Figure 12:
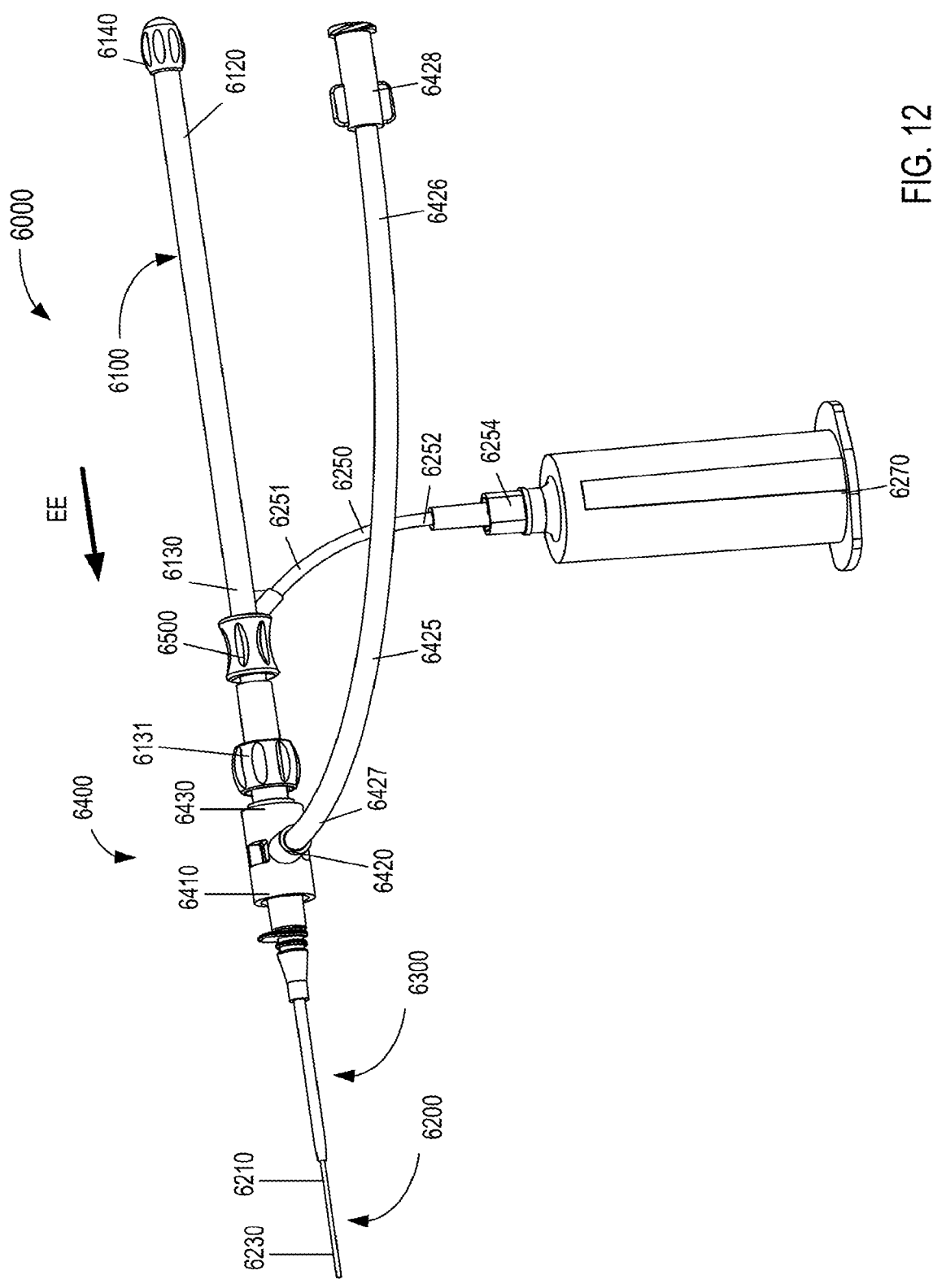
FIG. 12 is a perspective view of the apparatus illustrated in FIG. 9, in a second configuration.

In use, a user (e.g., a phlebotomist) can engage the actuator 6500 of the blood draw apparatus 6000 to move the actuator 6500 in the distal direction, as indicated by the arrow EE in FIG. 12. In this manner, the actuator 6500 moves in the distal direction relative to the introducer 6100 to place the apparatus in the second configuration. As described above, the user can apply a sufficient amount of force to the actuator 6500 such that the friction between the walls of the introducer 6100 and the guide member 6520 of the actuator 6500 is overcome. With the cannula 6200 coupled to the coupler 6530 of the actuator 6500, the cannula 6200 is moved in the distal direction concurrently with the actuator 6500 toward the second configuration.

As indicated by the arrow FF in FIG. 13, the cannula 6200 is advanced through the seal member 6132 included in the lock mechanism 6131, through a lumen 6401 defined by the adapter 6400 and through the PIV 6300 such that the distal end 6230 of the cannula 6200 extends beyond the PIV 6300. In this manner, the distal end 6230 of the cannula 6200 is substantially disposed within the vein of the patient such that the lumen 6201, defined by the cannula 6200, is in fluid communication with the vein. As shown in FIG. 13A, the cannula 6200 can be advanced through the PIV 6300 such that a distal surface 6206 of the first portion 6205 of the cannula 6200 is placed in contact with a proximal surface 6301 of a portion of the PIV 6300. Thus, the distal surface 6206 of the cannula 6200 engages the proximal surface 6301 of the PIV 6300 to prevent the cannula 6200 from being advanced beyond the second configuration. Similarly stated, the distal surface 6206 is configured to contact the proximal surface 6301 of the portion of the PIV 6300 to limit the travel of the cannula 6200. While the first portion 6205 and the second portion 6210 of the cannula 6200 shown in FIG. 13A include a substantially similar inner diameter, in other embodiments, the first portion 6205 can have a substantially larger inner diameter than the second portion 6210. In some embodiments, an inner wall or a set of inner walls that define the lumen 6201 can include a tapered transition between the first portion 6205 and the second portion 6210. In other embodiments, the inner wall or walls need not include a tapered portion.

While not shown in FIG. 13, a fluid container (e.g., a Vacutainer®) can be disposed within the cavity 6271 defined by the container shroud 6270 such that the sheath 6256 is withdrawn from the needle 6255 and the needle 6255 pierces the fluid container, thereby placing the fluid container in fluid communication with the vein of the patient. In other embodiments, the fluid container can be monolithically formed with the container shroud 6270 and/or with the introducer such that the movement of the actuator 6500 can urge the needle 6255 to pierce the fluid container. In some embodiments, the fluid container is configured to define a negative pressure (e.g., a Vacutainer®). In such embodiments, when the needle 6255 pierces the fluid container, the negative pressure within the fluid container introduces a suction force within the lumen 6253 of the secondary cannula 6250 and the lumen 6201 of the cannula 6200. The suction force is such that a bodily fluid (e.g., blood) is drawn through the lumen 6201 of the cannula 6200 and the lumen 6253 of the secondary cannula 6250 and into the fluid container, as indicated by the arrow GG in FIG. 13. In this manner, a phlebotomist can collect (e.g., draw) a given amount of blood through an existing peripheral intravenous line without the need for additional needle sticks.

Figure 14:
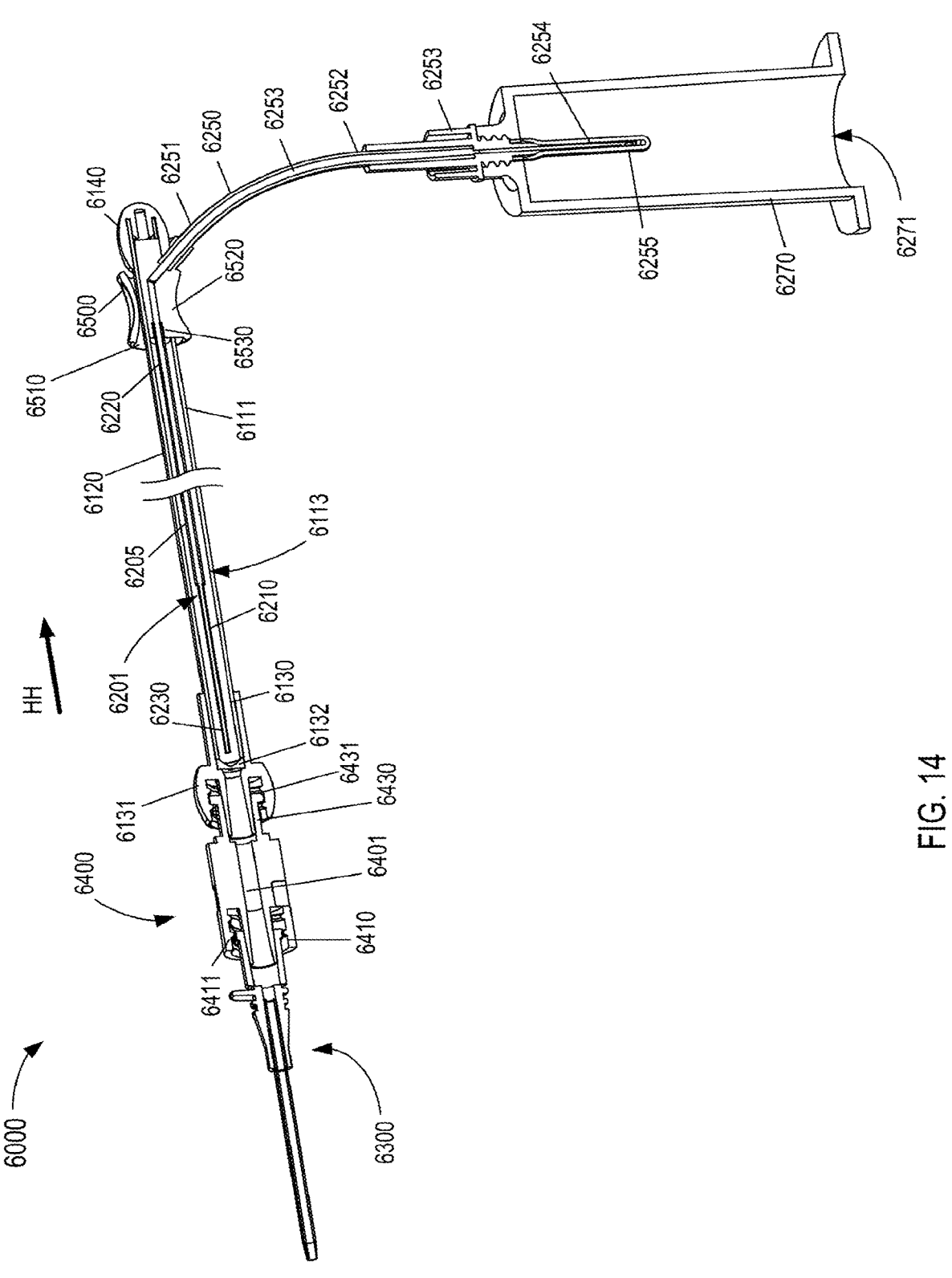
FIG. 14 is a cross-sectional perspective view of the apparatus illustrated in FIG. 9, in a third configuration.

With the desired amount of bodily fluid collected, the user (e.g., phlebotomist) can move the actuator 6500 in the proximal direction, thereby placing the apparatus 6000 in a third (used) configuration, as indicated by the arrow HH in FIG. 14. In the third configuration, the cannula 6200 is substantially fluidically isolated from a volume outside the introduce 6100. Therefore, the introducer 6100 (e.g., the lock mechanism 6131) can be decoupled from the second port 6430 of the adapter 6400 and safely discarded.

Figures 15, 16:
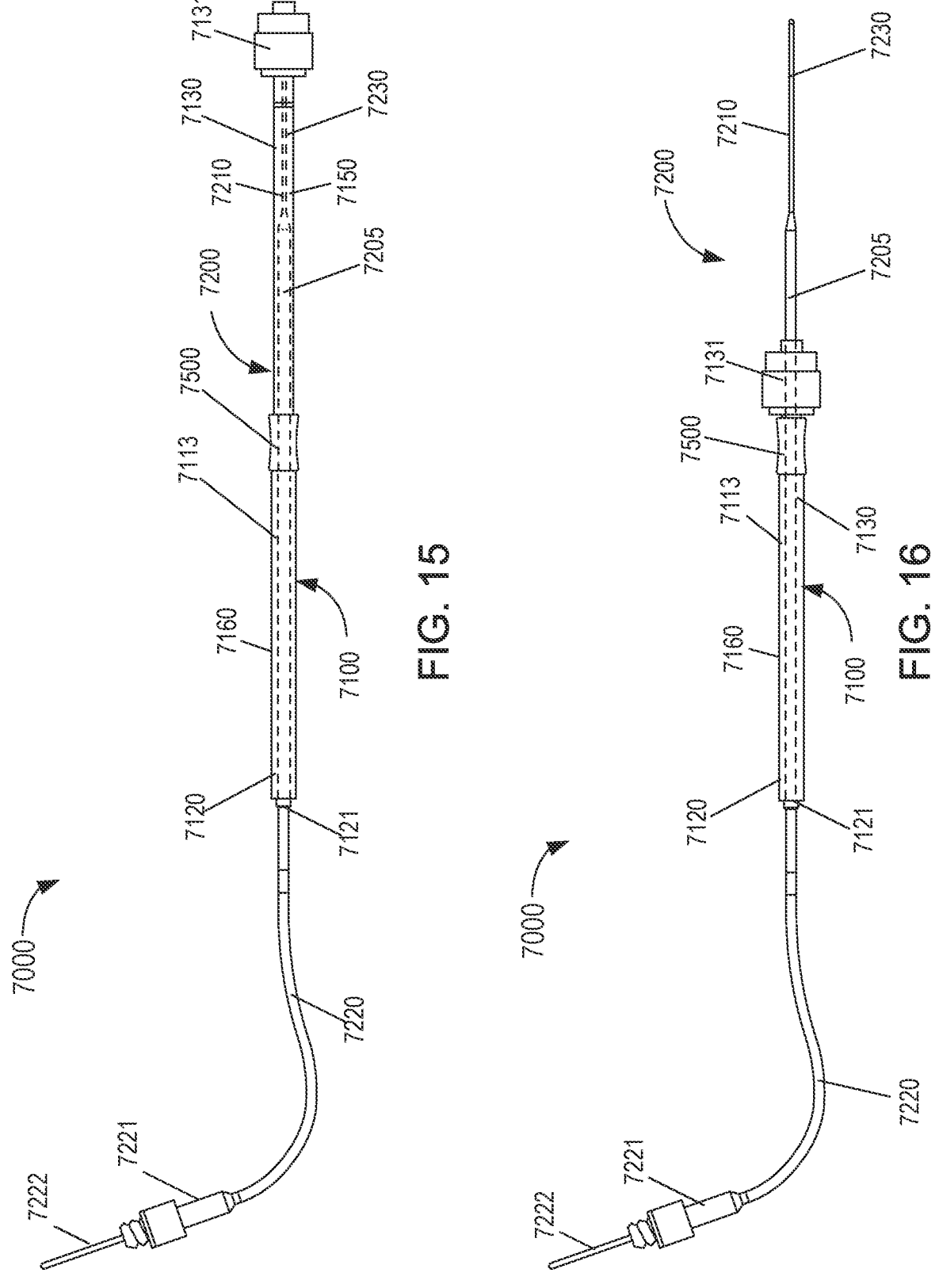
FIGS. 15 and 16 are a side view of an apparatus in a first configuration and a second configuration, respectively, according to an embodiment.
Figure 17:
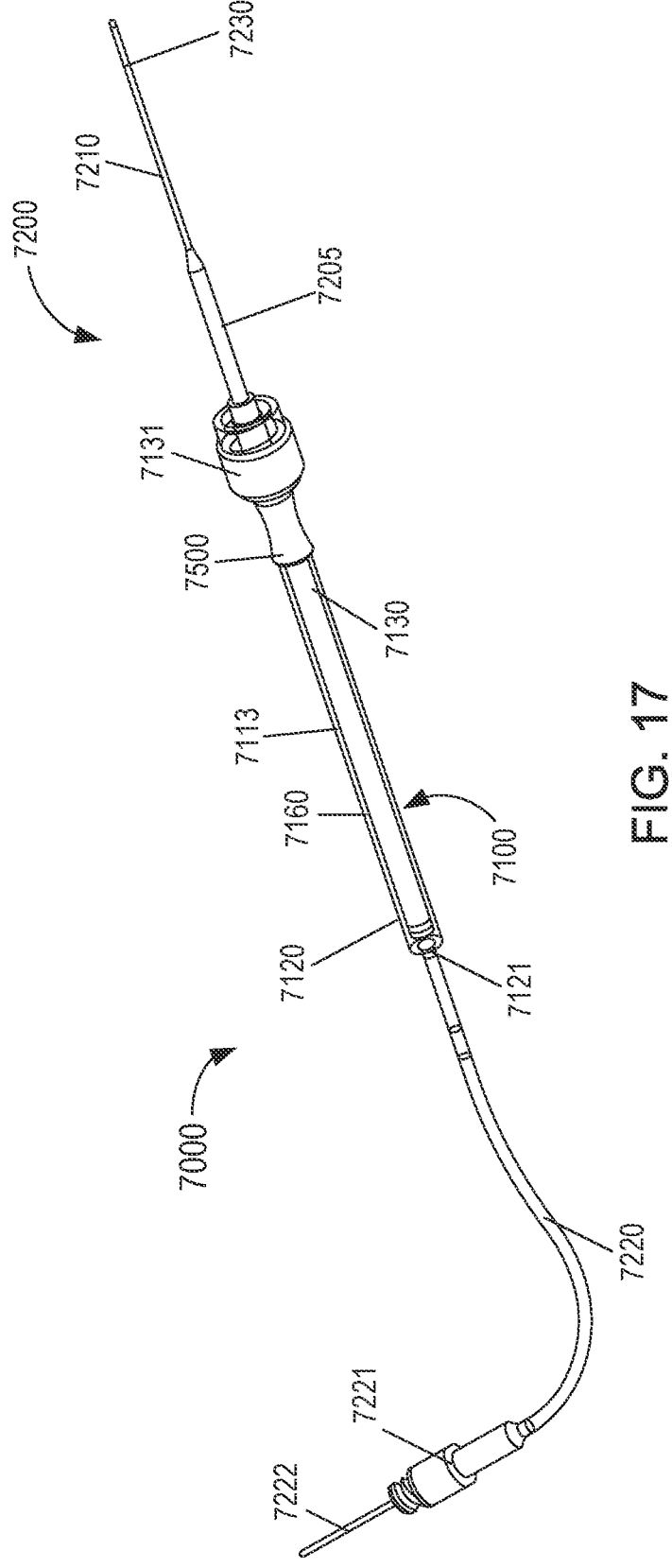
FIG. 17 is a perspective view of the apparatus illustrated in FIG. 15, in the second configuration.

While the apparatus 6000 (shown and described with respect to FIGS. 9-14) includes a single piece introducer 6100, in some embodiments, an apparatus can include a multi-piece introducer configured for telescopic motion. For example, FIGS. 15-22 illustrate an apparatus 7000 according to an embodiment. As shown in FIGS. 15-17, the apparatus 7000 includes an introducer 7100 and a cannula 7200 and is configured to be moved between a first configuration (FIG. 15) and a second configuration (FIGS. 16 and 17), as described in further detail herein.

The introducer 7100 includes a first member 7150 defining a first lumen 7155 and a second member 7160 defining a second lumen 7165. In some embodiments, the first member 7150 is a substantially cylindrical tube having a first diameter and the second member 7160 is a substantially cylindrical tube having a second diameter, larger than the first diameter. In this manner, the lumen 7165 defined by the second member 7160 is configured to receive at least a portion of the first member 7155. More specifically, the first member 7150 is movably disposed within the second member 7165 such that the introducer 7100 can be moved in a telescopic motion. Similarly stated, the second member 7160 is configured to move between a first position and a second position, relative to the first member 7150. Furthermore, the second member 7160 includes an actuator portion 7500 configured to be engaged by a user (e.g., a phlebotomist) to move the second member 7160 relative to the first member 7150.

The introducer 7100 includes a proximal end 7120 and a distal end 7130. The proximal end 7120 includes a port 7121. The port 7121 can be any suitable port. For example, in some embodiments, the port 7121 is substantially similar to the port 1121, described above with reference to FIGS. 1 and 2. In this manner, the port 7121 is configured to receive a portion of the catheter 7200, as described in further detail herein. The distal end 7130 can be coupled to a lock mechanism 7131. The lock mechanism 7131 can be any suitable mechanism such as, for example, a Luer Lok™. In some embodiments, the lock mechanism 7131 can be substantially similar to the lock mechanism 6131 described above with reference to FIGS. 9-14. Therefore, the lock mechanism 7131 is not described in further detail herein.

The introducer 7100 is configured to receive at least a portion of the cannula 7200. More specifically, the cannula 7200 includes a proximal end 7220 and a distal end 7230 and is at least partially disposed within the introducer 7100 such that the proximal end 7220 of the cannula 7200 extends through the port 7121 of the introducer 7100. In this manner, the cannula 7200 is configured to move relative to at least a portion of the introducer 7100 between a first configuration and a second configuration, as further described herein.

The proximal end 7220 of the cannula 7200 is coupled to a lock mechanism 7221. The lock mechanism 7221 can be any suitable lock mechanism, such as, for example, a Luer Lok™. Furthermore, the lock mechanism 7221 is coupled to a needle 7222 such that when the proximal end 7220 of the cannula 7200 is coupled to the lock mechanism 7221, a lumen (not shown in FIGS. 15-22) defined by the cannula 7200 is placed in fluid communication with a lumen (not shown in FIGS. 15-22) defined by the needle 7222. The distal end 7230 of the cannula 7200 includes a first portion 7205, having a first diameter, and a second portion 7210, having a second diameter, smaller than the first diameter. As shown in FIG. 17, the cannula 7200 is configured to include a taper between the first portion 7205 and the second portion 7210. The taper can be any suitable configuration and can be substantially similar to the taper portion 4203 described above with reference to FIG. 5.

Figure 18:
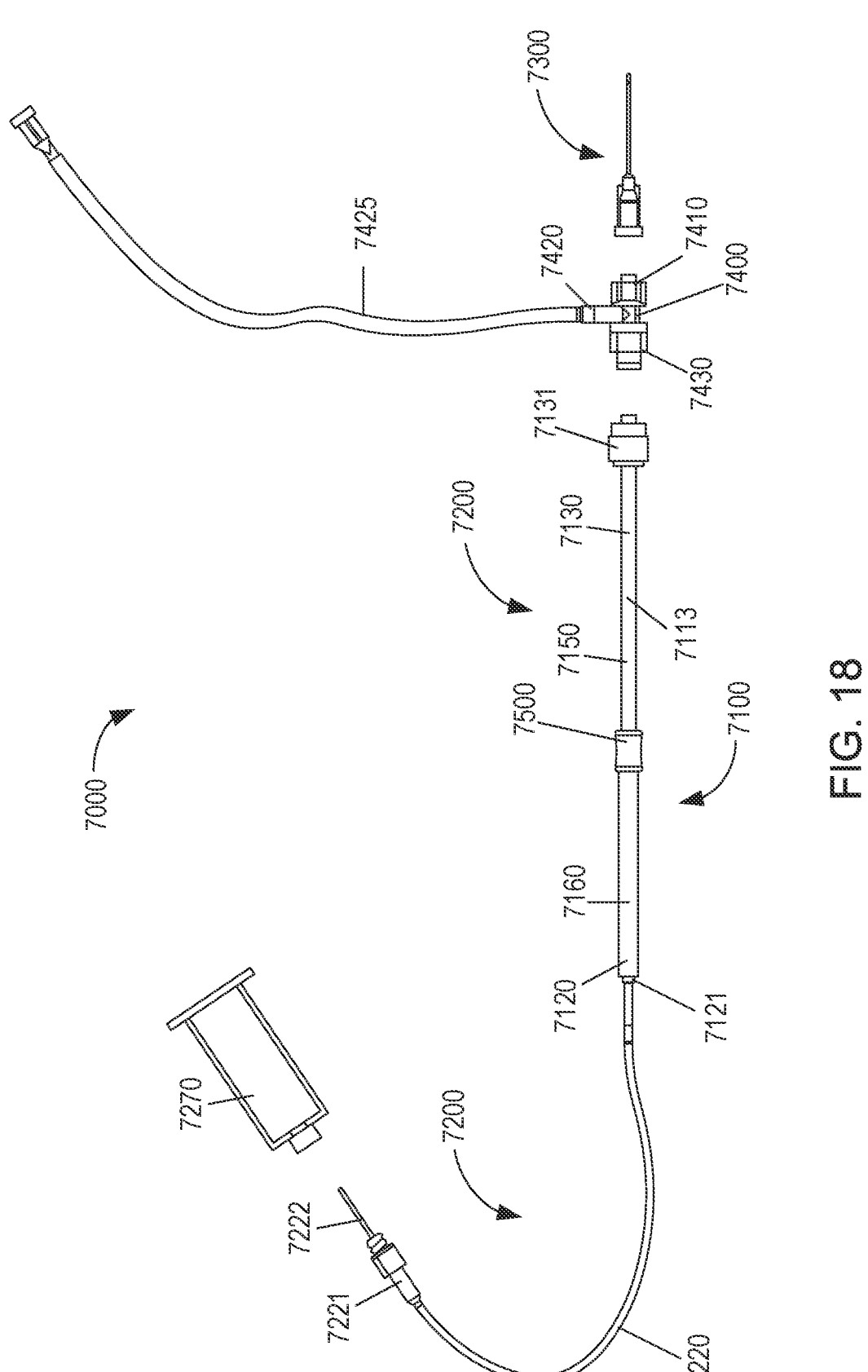
FIG. 18 is an exploded side view of the apparatus of FIG. 15 and an adapter, according to an embodiment.

As shown in the exploded view of FIG. 18, the lock mechanism 7131 is configured to be coupled to an adapter 7400. The adapter includes a distal end 7410, a first port 7420, and a second port 7430. The adapter 7400 can be any suitable adapter described herein. For example, in some embodiments, the adapter can be substantially similar to the adapter 6400 described above with reference to FIGS. 9-14. In other embodiments, the adapter 7400 can be any known adapter, such as, for example, a Y-adapter or a T-adapter. In this manner, the first port 7420 of the adapter 7400 is configured to be coupled to an inlet catheter 7425. The inlet catheter 7425 can be any suitable configuration. In some embodiments, the inlet catheter 7425 is substantially similar in form and function to the inlet catheter 6425 described above with reference to FIGS. 9-14. Therefore, the inlet catheter 7425 is not described in detail herein.

The second port 7430 is configured to be coupled to the lock mechanism 7131. In this manner, the second port 7430 and the lock mechanism 7131 can be configured to form a substantially fluid tight seal. For example, in some embodiments, the second port 7430 can include a threaded coupling configured to engage a threaded coupling of the lock mechanism 7131, thereby defining the substantially fluid tight seal. Furthermore, the lock mechanism 7131 can include a seal member (not shown in FIGS. 15-22) configured to selectively fluidically isolate a lumen 7113 defined by the introducer 7100 from a lumen (not shown) defined by the adapter. For example, in some embodiments, the seal member can be substantially similar in form and function to the seal member 6132 described above with reference to FIG. 11. The distal end 7410 of the adapter 7400 is configured to be coupled to a peripheral intravenous line (PIV) 7300. In some embodiments, the PIV 7300 is a known PIV. In this manner, the distal end 7410 of the adapter 7400 can include any suitable feature configured to physically and fluidically couple the adapter 7400 to the PIV 7300.

Figure 19:
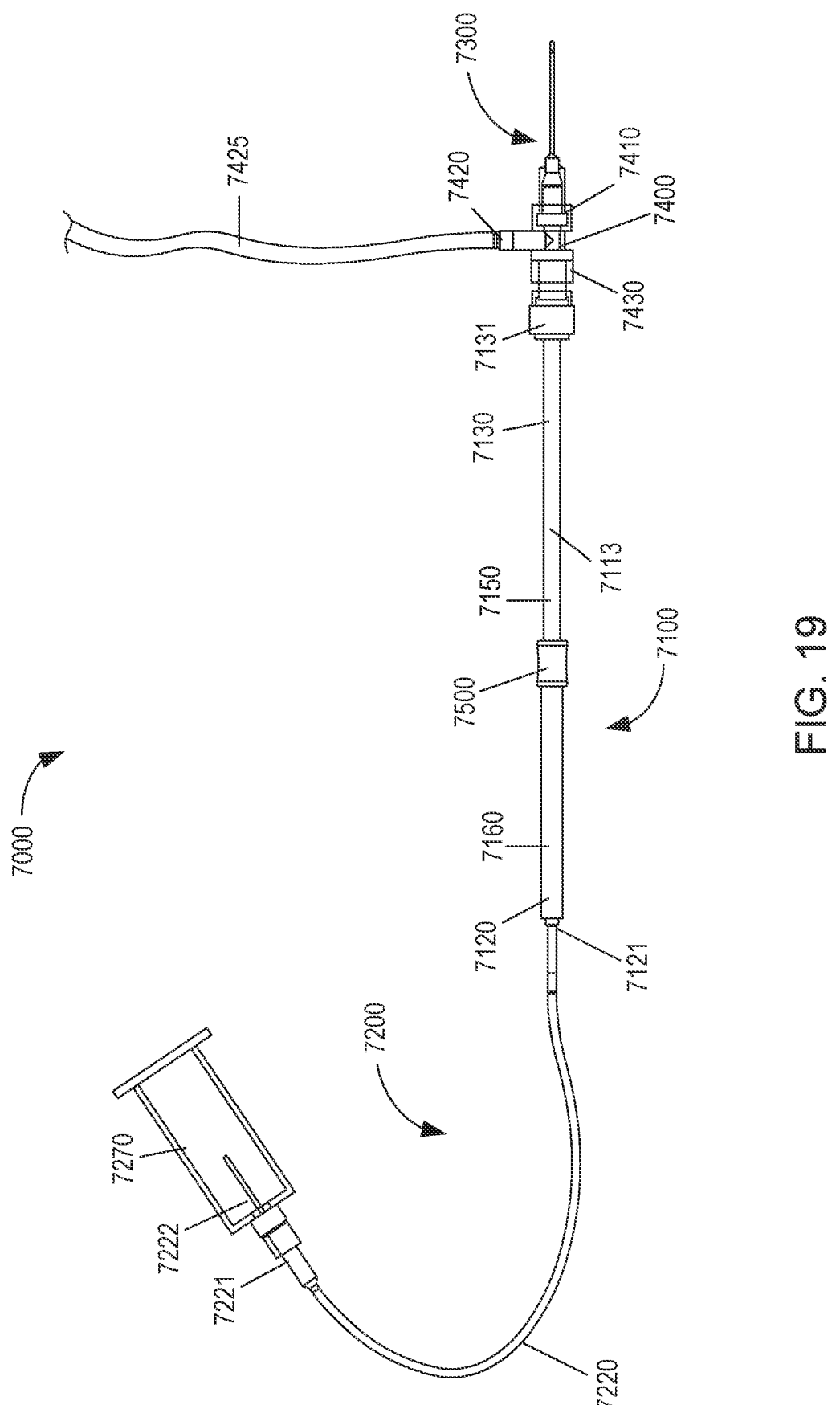
FIG. 19 is a side view of the apparatus and adapter illustrated in FIG. 18, in a first configuration.
Figure 20:
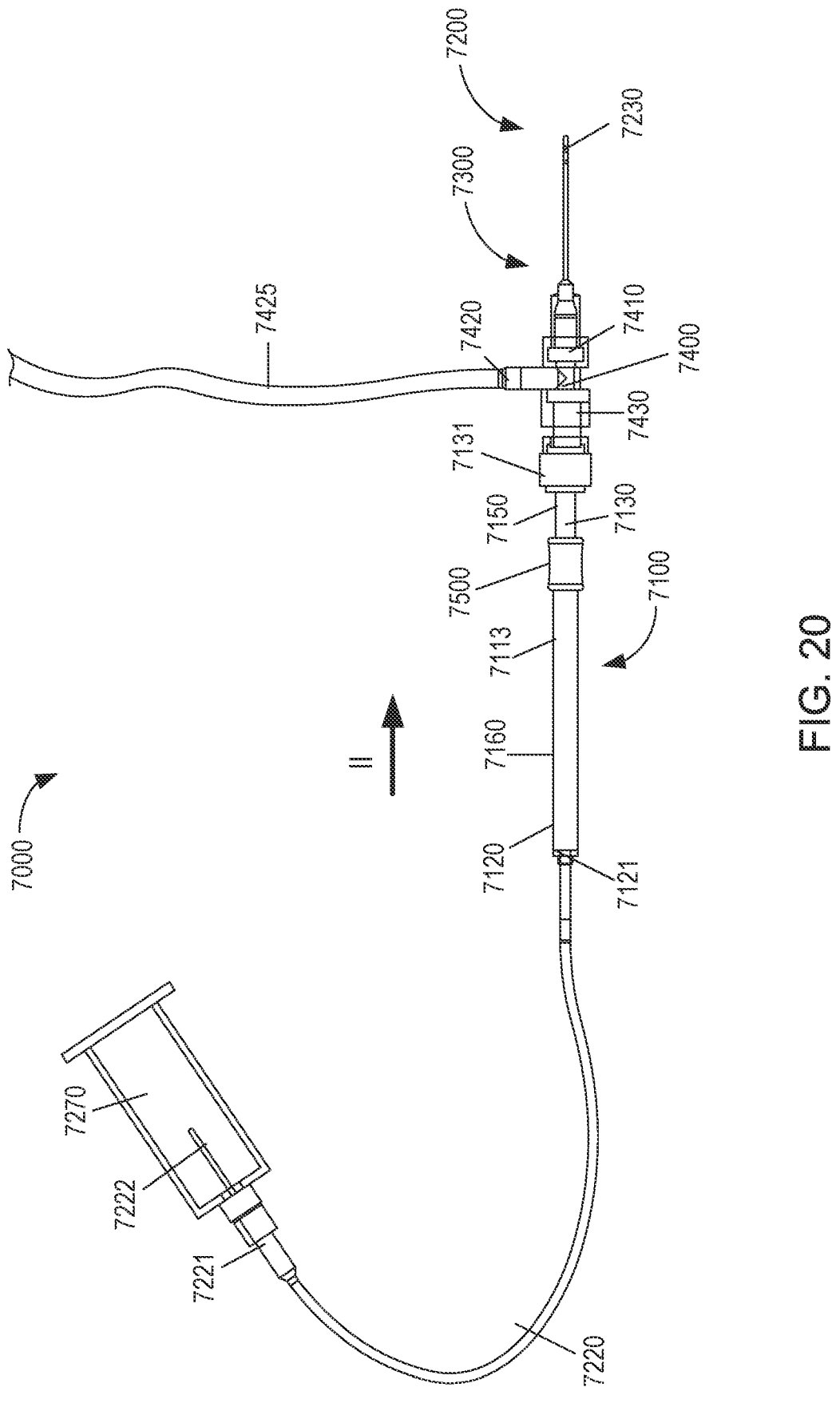
FIG. 20 is a side view of the apparatus and the adapter illustrated in FIG. 18, in a second configuration.
Figure 21:
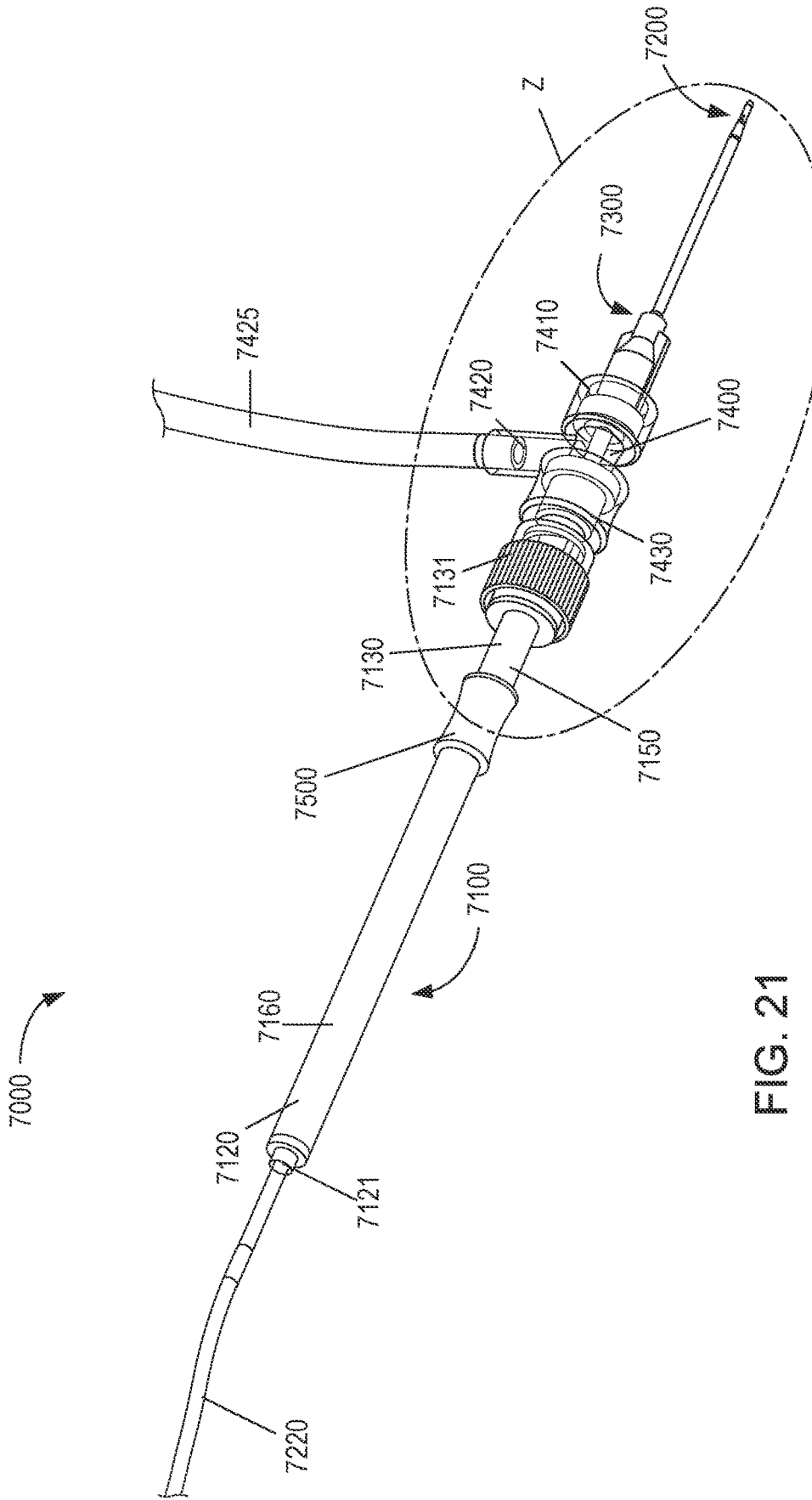
FIG. 21 is a perspective view of the apparatus illustrated in FIG. 18, in the second configuration.
Figure 22:
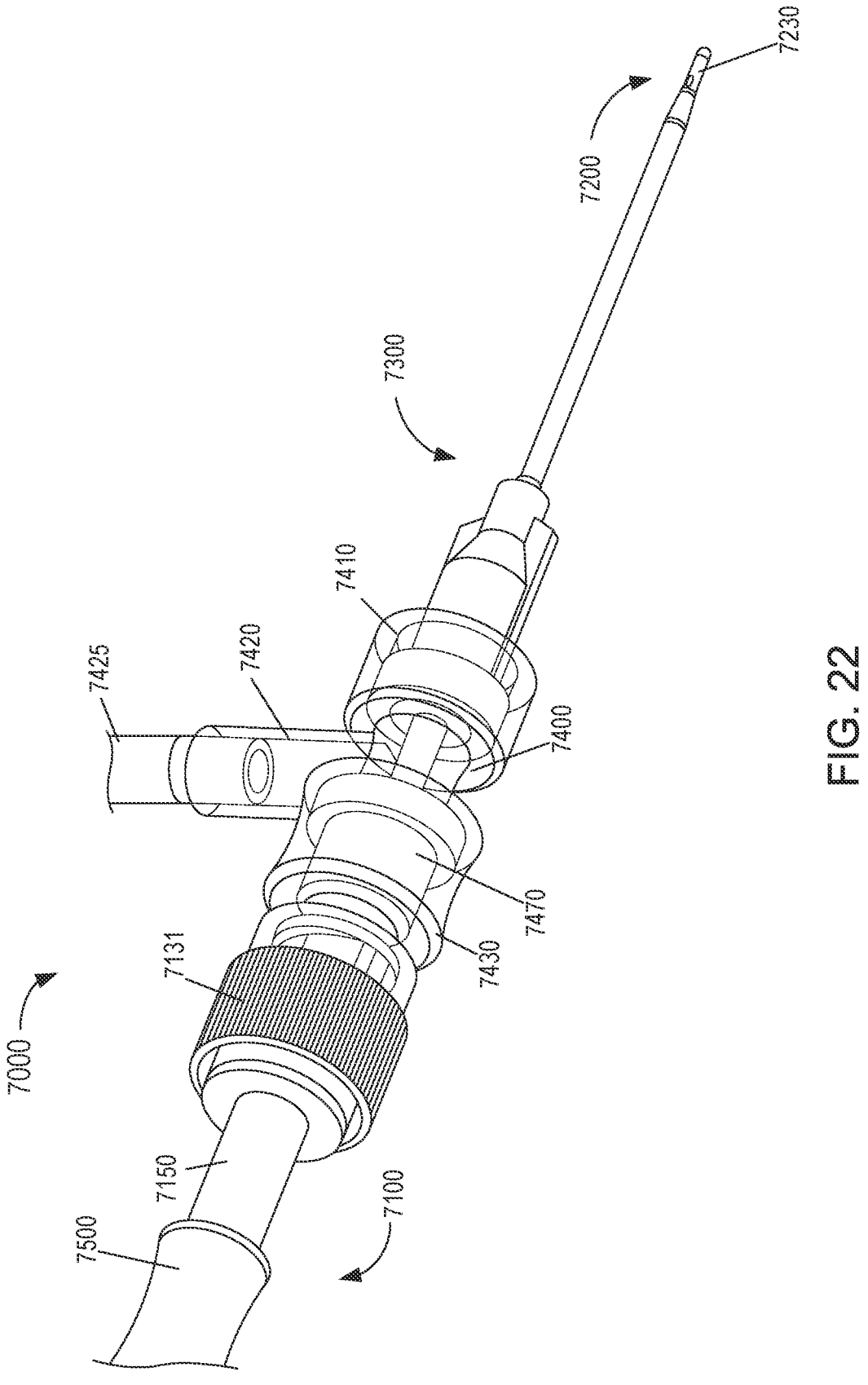
FIG. 22 is an enlarged view of a portion of the apparatus of FIG. 18, indicated by the region Z in FIG. 21.

As shown in FIG. 19, the apparatus 7000 can be in the first configuration such that he second member 7260 of the introducer 7100 is disposed in a proximal position relative to the first member 7150 of the introducer 7100. In use, a user (e.g., a phlebotomist) can engage the actuator 7500 included in the second member 7160 of the introducer 7100 and move the second member 7160 in the distal direction, as indicated by the arrow II in FIG. 20. In this manner, the introducer 7100 moves in a telescopic motion such that the second member 7160 moves relative to the first member 7150. Similarly stated, an overall length of the introducer 7100 is reduced when the second member 7160 moves relative the first member 7150. Furthermore, the distal movement of the second member 7160 is such that the cannula 7200 is moved in the distal direction. In this manner, the distal end 7230 of the cannula 7200 passes through the seal member included in the lock mechanism 7131 (as similarly described above in reference to FIGS. 11 and 13) and through the PIV 7300. As shown in the enlarged view of FIG. 22, the distal end 7230 of the cannula 7200 extends beyond the PIV 7300 to place a lumen (not shown) defined by the cannula 7200 in fluid communication with a portion of a body of a patient (e.g., a vein). Furthermore, in some embodiments, the adapter 7400 can be configured to include a seal member 7470 configured to receive the cannula 6200. In this manner, the seal member 7470 can prevent a backflow of a bodily fluid into, for example, the introducer 7100.

With the apparatus 7000 in the second configuration (e.g., FIGS. 20-22), the user can dispose a fluid container (e.g., a Vacutainer®, or any other suitable fluid container) within a container shroud 7270 such that the container engages the needle 7222. In this manner, the needle 7222 can pierce a portion of the fluid container (not shown) to place the fluid container in fluid communication with the lumen defined by the cannula 7200. In addition, with the distal end 7230 of the cannula 7200 disposed within, for example, the vein of the patient, the fluid container can be placed in fluid communication with the vein. In some embodiments, such as those where the fluid container is a Vacutainer® or the like, the fluid container can define a negative pressure (e.g., the fluid container is an evacuated container). In such embodiments, the negative pressure defined by the fluid container can introduce a suction force to the lumen defined by the cannula 7200 such that a bodily fluid (e.g., blood) is drawn through the cannula 7200 and into the fluid container. In this manner, a phlebotomist can collect (e.g., draw) a given amount of blood through an existing peripheral intravenous line without the need for additional needle sticks.

Figures 23, 24:
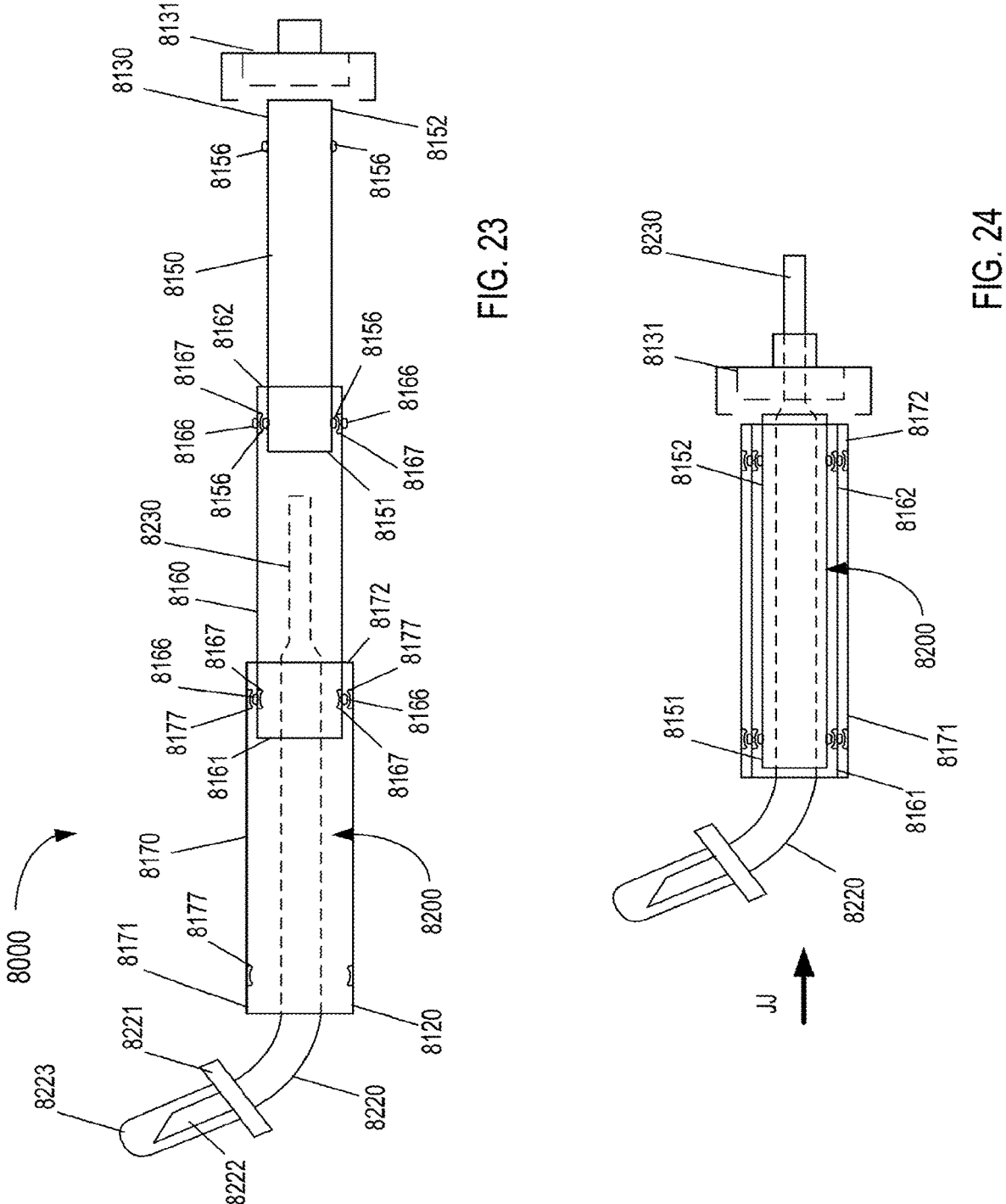
FIGS. 23 and 24 are schematic illustrations of an apparatus in a first configuration and a second configuration, according to an embodiment.

While the apparatus 7000 described above with reference to FIGS. 15-22 includes an introducer 7100 with a first member 7150 and a second member 7160, in some embodiments, an apparatus can include an introducer with any suitable number of portions or members. For example, FIGS. 23 and 24 illustrate an apparatus 8000 according to an embodiment. The apparatus 8000 includes at least an introducer 8100 and a cannula or catheter 8200 and is configured to be moved between a first configuration (FIG. 23) and a second configuration (FIG. 24).

The introducer 8100 includes a first member 8150, a second member 8160, and a third member 8170. In some embodiments, the first member 8150 can have a first diameter, the second member 8160 can have a second diameter, larger than the first diameter, and the third member 8170 can have a third diameter, larger than the second diameter. In this manner, at least a portion of the first member 8150 can be movably disposed within the second member 8160. Similarly, at least a portion of the second member 8160 can be movably disposed within the third member 8170. In this manner, the introducer 8100 can be configured to be moved in a telescopic motion, as similarly described above with respect to the introducer 7100.

As shown in FIGS. 23 and 24, the first member 8150 includes a set of protrusions 8156 disposed at a proximal end 8151 and a distal end 8152 of the first member 8150. The second member 8160 similarly includes a set of protrusions 8166 and a set of grooves 8167 disposed at a proximal end 8161 and a distal end 8162 of the second member 8160. In a similar manner, the third member 8170 includes a set of grooves 8177 disposed at a proximal end 8171 and a distal end 8172 of the third member 8170. The set of protrusions 8156 and 8166 are configured to selectively engage the set of grooves 8167 and 8177, respectively, as described in further detail herein.

The introducer 8100 includes a proximal end 8120 and a distal end 8130. The proximal end 8120 is configured to receive a portion of the catheter 8200. More specifically, the catheter 8200 is movably disposed within the introducer 8100 such that a proximal end 8220 extends through the proximal end 8120 of the introducer 8100. The distal end 8130 of the introducer 8100 is coupled to a lock mechanism 8131. The lock mechanism 8131 can be any suitable lock mechanism described herein. Therefore, the lock mechanism 8131 is not described in further detail.

The catheter 8200 includes the proximal end 8220 and a distal end 8230. As described above, the proximal end 8220 is configured to extend through the proximal end 8120 of the introducer 8100 when the catheter 8200 is disposed within the introducer 8100. The proximal end 8220 is coupled to a lock mechanism 8221. The lock mechanism 8221 is further coupled to a needle 8222 and a sheath 8223. The lock mechanism 8221, the needle 822, and the sheath 8223 can be substantially similar in form and function to the lock mechanism 2221, the needle 2222, and the sheath 2223, respectively, described above with reference to FIG. 3. Therefore, the lock mechanism 8221, the needle 8222 and the sheath 8223 are not further described herein.

As shown in FIG. 23, the apparatus 8000 can be in the first configuration such that the introducer 8100 is in a non-collapsed configuration. Similarly stated, the third member 8170 of the introducer 8100 is in a proximal position, relative to the second member 8160, and the second member 8160 is in a proximal position, relative to the first member 8150. Expanding further, in the first configuration, the grooves 8167 disposed at the distal end 8162 of the second member 8160 are in contact with the protrusions 8156 disposed at the proximal end 8151 of the first member 8150. Similarly, the grooves 8177 disposed at the distal end 8172 of the third member 8170 are in contact with the protrusions 8166 disposed at the proximal end 8161 of the second member 8160. The arrangement of the protrusions 8156 and 8166 within the grooves 8167 and 8177, respectively, is such that the introducer 8100 is maintained in the non-collapsed (e.g., extended or telescoped configuration). Furthermore, the protrusions 8156 and 8166 can form a friction fit with a surface defining the grooves 8167 and 8177. In this manner, the introducer 8100 can be maintained within the first configuration until an external force is applied to the introducer 8100 to move the introducer towards the second configuration.

For example in use, a user (e.g., a phlebotomist) can engage the introducer 8100 and apply a given force, as indicated by the arrow JJ in FIG. 24. In this manner, the applied force can be such that the third member 8170 moves in the distal direction relative to the second member 8160. Similarly, the second member 8160 is moved in the distal direction relative to the first member 8150 (e.g., the applied force is sufficiently large to overcome the friction force between the protrusions 8156 and 8166 and the surface defining the grooves 8167 and 8177, respectively). Therefore, the introducer 8100 is moved to the second configuration in which the introducer 8100 is substantially collapsed or compressed. Furthermore, the relative distal movement of the third member 8170 and the second member 8160 is such that the set of grooves 8167 at the proximal end 8161 and the distal end 8162 of the second member 8160 engage the set of protrusions 8156 at the proximal end 8151 and the distal end 8152, respectively, of the first member 8150. Similarly, the set of grooves 8177 at the proximal end 8171 and the distal end 8172 of the third member 8170 engage the set of protrusions 8166 at the proximal end 8161 and the distal end 8162 of the second member 8160.

In this manner, the introducer 8100 is in the second configuration and the set of protrusions 8156 and 8166 engage the surfaces defining the set of grooves 8167 and 8177 to define a friction fit. Thus, the introducer 8100 is maintained in the second configuration. Furthermore, the telescopic motion of the introducer 8100 is such that the catheter 8200 disposed within the introducer 8200 is advanced through the lock mechanism 8131, as shown in FIG. 24. As described herein, the lock mechanism 8131 can be coupled to any suitable adapter and/or peripheral intravenous line. Therefore, when in the second configuration, the catheter 8200 extends beyond the PIV to draw a portion of a bodily fluid, as described herein (e.g., similar to the apparatus 7000 described herein with reference to FIGS. 15-22).

Figure 25:
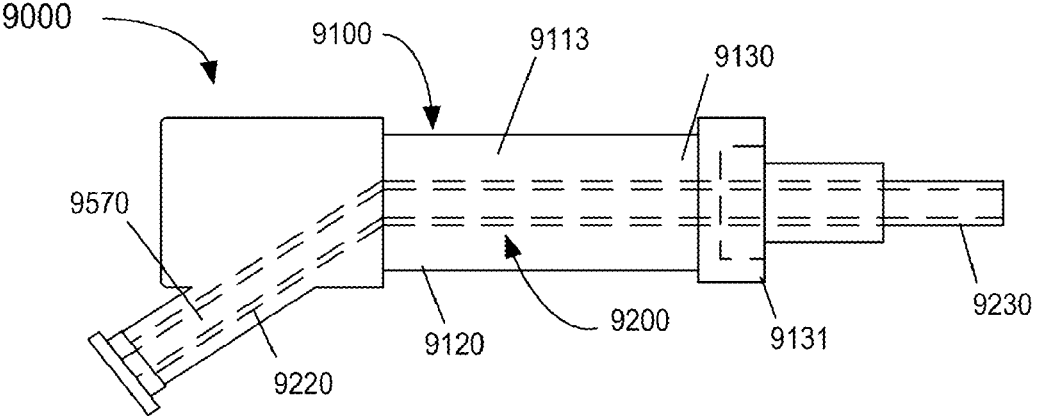
FIGS. 25 and 26 are schematic illustrations of an apparatus in a first configuration and a second configuration, according to an embodiment.
Figure 26:
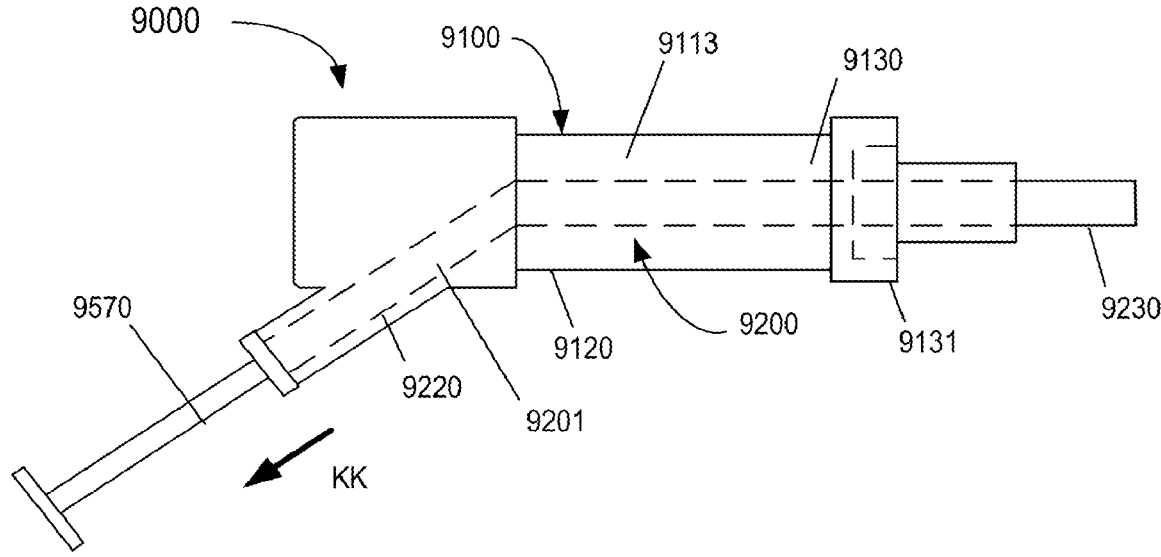

While the apparatus 6000 described above with reference to FIGS. 9-14 includes an annular shaped actuator 6500, in some embodiments, an apparatus can include any suitable actuator. For example, FIGS. 25 and 26 illustrate an apparatus 9000 according to an embodiment, in a first configuration and a second configuration, respectively. The apparatus 9000 includes an introducer 9100, a cannula 9200, and an actuator 9570. The introducer 9100 includes a proximal end 9120 and a distal end 9230 and defines a lumen 9113. The distal end 9230 is configured to be coupled to a lock mechanism 9131. The cannula 9200 includes a proximal end 9220 and a distal end 9230 and defines a lumen 9201. The introducer 9100 and the cannula 9200 can be substantially similar in form and function to any introducer and cannula/catheter described herein. Therefore, the introducer 9100 and the cannula 9200 are not described in further detail herein.

As shown in FIG. 25, the actuator 9570 can be configured to be a stylet or wire. In this manner, the actuator 9570 can be movably disposed within the cannula 9200. Furthermore, the actuator 9570 can be sufficiently stiff such as to advance the cannula 9200 through the introducer 9100, the lock mechanism 9131, and an existing PIV (not shown in FIGS. 25 and 26) substantially without kinking or creasing. The actuator 9570 can be configured to be moved in the proximal direction relative to the cannula 9200, as indicated by the arrow KK in FIG. 26. In this manner, the actuator 9570 can be removed from the cannula 9200 and the cannula 9200 can be placed in fluid communication with a fluid container. Thus, the cannula 9200 can facilitate a transfer of a bodily fluid from a patient to the fluid container, as described above.

Figure 27:
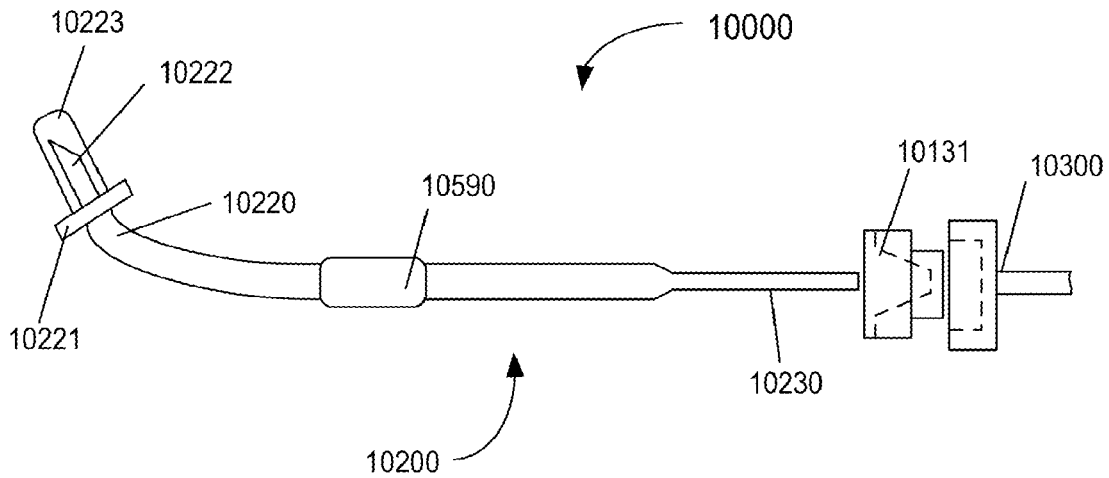
FIGS. 27 and 28 are schematic illustrations of an apparatus in a first configuration and a second configuration, according to an embodiment.
Figure 28:
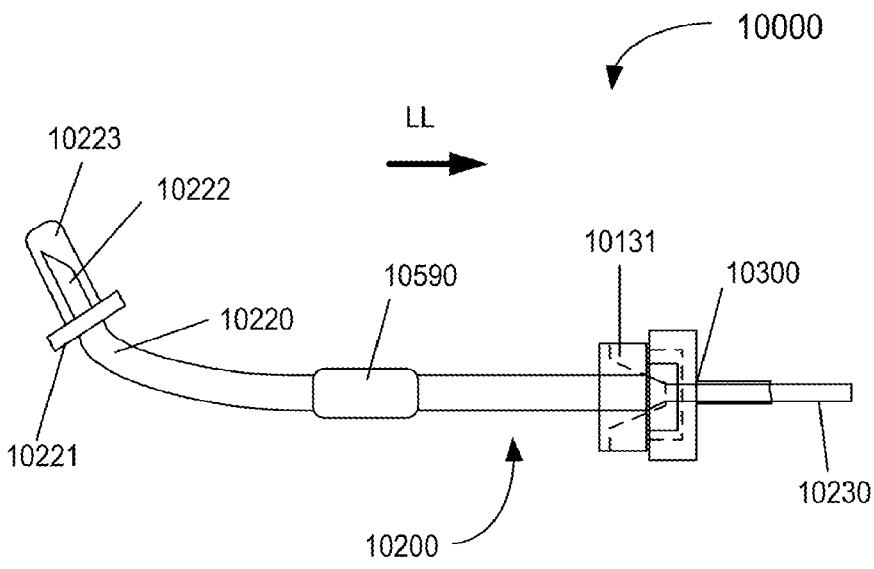

While the embodiments described herein have included an introducer, in some embodiments, an apparatus need not include an introducer. For example, FIGS. 27 and 28 illustrate an apparatus 10000 according to an embodiment, in a first configuration and a second configuration, respectively. The apparatus 10000 can include a cannula or catheter 10200 with a proximal end 10220 and a distal end 10230. The cannula 10200 can be substantially similar in form and function to any cannula/catheter described herein. For example, in some embodiments, the proximal end 10220 includes a lock mechanism 10221, a needle 10222, and a sheath 10223, substantially similar to the lock mechanism 2221, the needle 2222, and the sheath 2223 described above with respect to FIG. 3.

The catheter 10200 is coupled to a handle 10590 configured to be engaged by a user (e.g., a phlebotomist). The apparatus 10000 can further include a lock mechanism 10131. The lock mechanism 10131 can be substantially similar in form and function to the lock mechanism 6131 described above with reference to FIG. 11. Therefore, in use, a user can couple the lock mechanism 10131 to a peripheral intravenous line (PIV) 10300 and define a fluid tight seal. With the lock mechanism 10131 coupled to the PIV 10300, the user can engage the handle 10590 coupled the catheter 10200 to advance the catheter 10200 through the lock mechanism 10131 and the PIV 10300, as indicated by the arrow LL in FIG. 28. Thus, the catheter 10200 can be placed in fluid communication with a fluid container and with the catheter 10200 extended beyond the PIV 10300, the catheter 10200 can facilitate a transfer of a bodily fluid from a patient to the fluid container, as described above.

Figure 29:
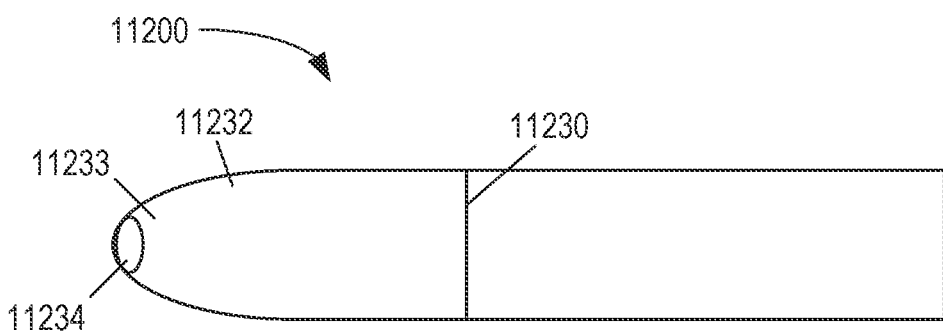
FIGS. 29-37 are side views of various catheter configurations included in an apparatus, according to an embodiment.

While specific cannulas or catheters are described herein as including a distal end of a particular configuration (i.e., with circumferential openings, etc.), in some embodiments the distal end of the catheter or cannula can include a different structure configured to facilitate the drawing of blood through the catheter. For example, FIG. 29 illustrates a catheter 11200 that includes a distal end 11230 with a bullet-shaped tip 11232. The bullet-shaped tip 11232 includes an end portion 11233 that defines a single opening 11234 at a distal end surface of the bullet-shaped tip.

Figure 30:
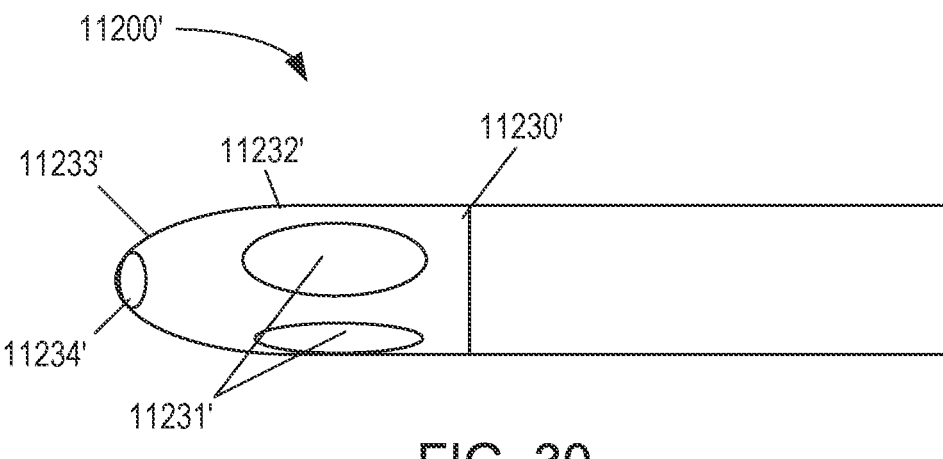

In some embodiments, such as, for example, a catheter 11200' shown in FIG. 30, a bullet-shaped tip 11232' includes an end portion 11233' that defines an end opening 11234'. In such embodiments, the bullet-shaped tip 11232' includes a set of side-wall openings 11231'. The end opening 11234' and the side openings 11231' can be configured to produce a laminar flow and act to transport a bodily fluid (i.e., blood) to a volume outside the catheter 11200'. While the openings 11231, 11231', 11234, and 11234' are illustrated as having a particular configuration, the shape and orientation/relative position of the openings can be varied to facilitate the fluid flow through the catheter.

Figure 31:
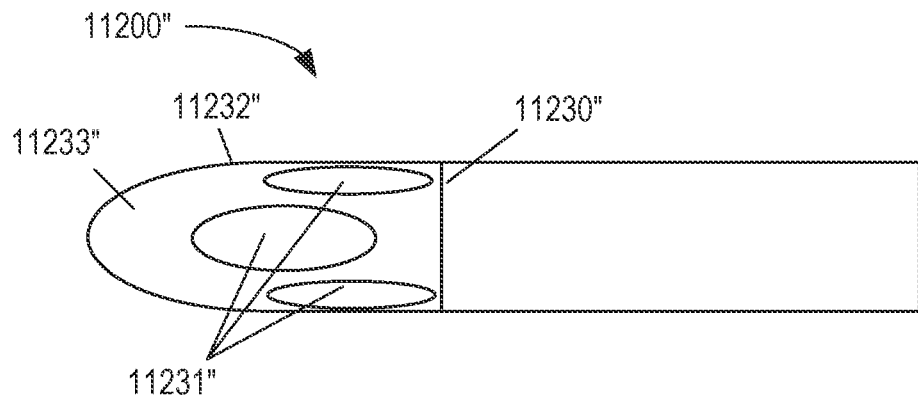

As shown in FIG. 31 the bullet-shaped tip 11232" can be configured to include a substantially closed rounded end portion 11233". In this manner, the bullet-shaped tip 11232" can be used to move through clots existing within a peripheral intravenous line. The bullet-shaped tip 11232" includes a set of sidewall openings 11231" that are operative to transport a bodily fluid (i.e., blood) to a volume outside the catheter 11200".

Figure 32:
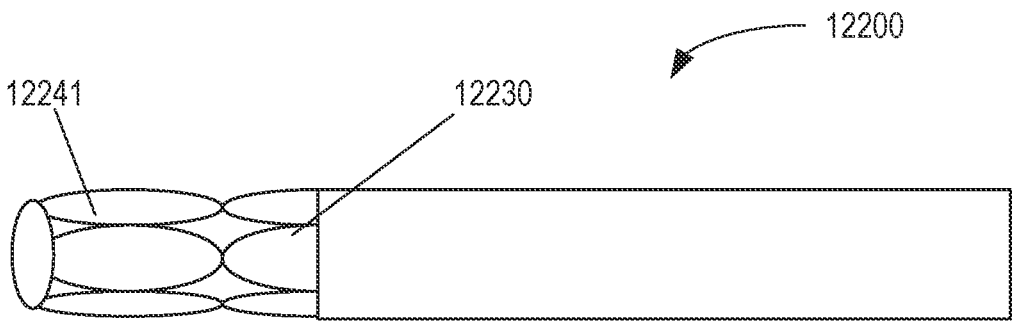
Figure 33:
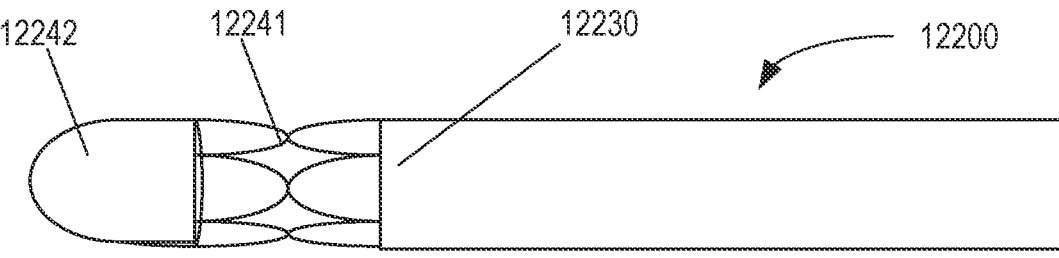
Figure 34:
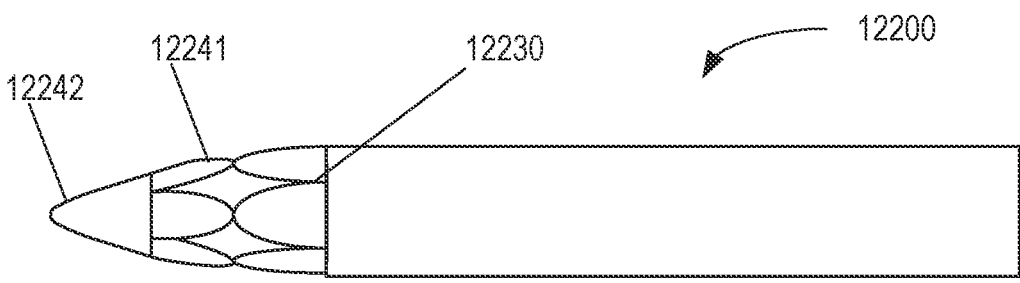

In some embodiments, for example as shown in FIGS. 32-34, a catheter 12200 includes a distal end 12230 with a wireframe tip 12241 having a stent-like configuration. The wireframe tip 12241 can be a flexible mesh configured to extend away from the distal end 12230 of the catheter 12200. The wireframe tip 12241 can act to transport a bodily flow (i.e., blood) to a volume outside the catheter 12200. In some embodiments, the wireframe tip 12241 can include a capped end 12242. The capped end 12242 can be any suitable size, shape, or configuration and, in some embodiments, can include any suitable number of openings.

Figure 35:
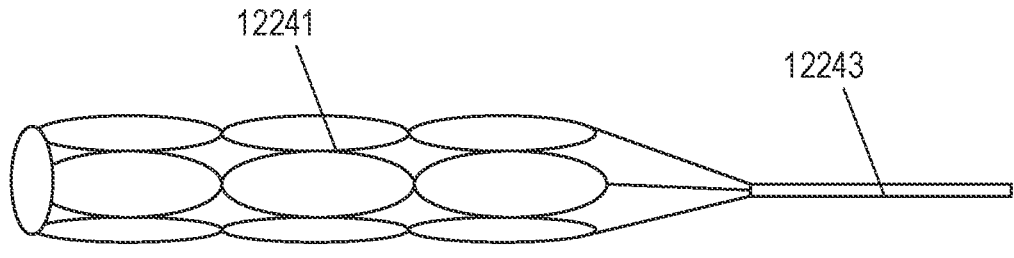
Figure 36:
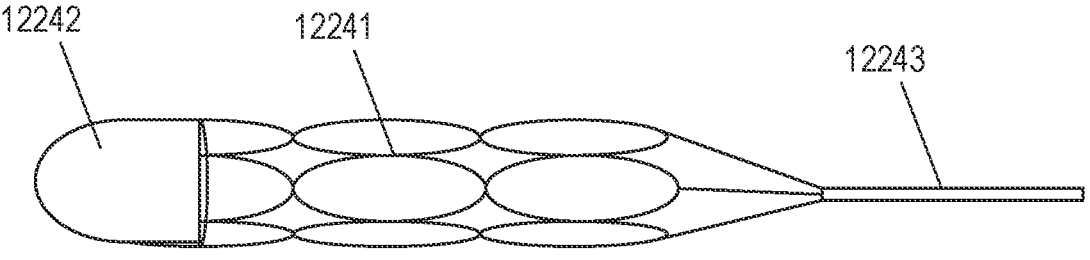
Figure 37:
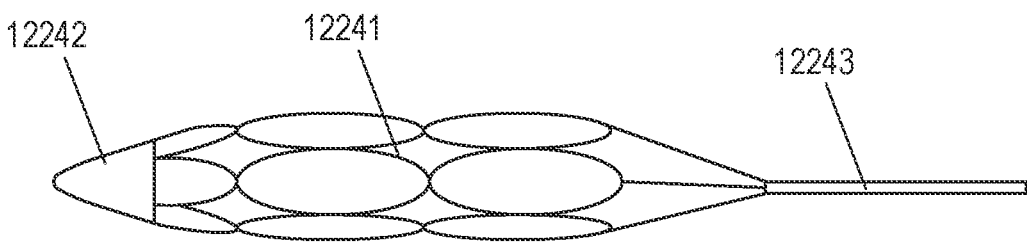
Figure 38:
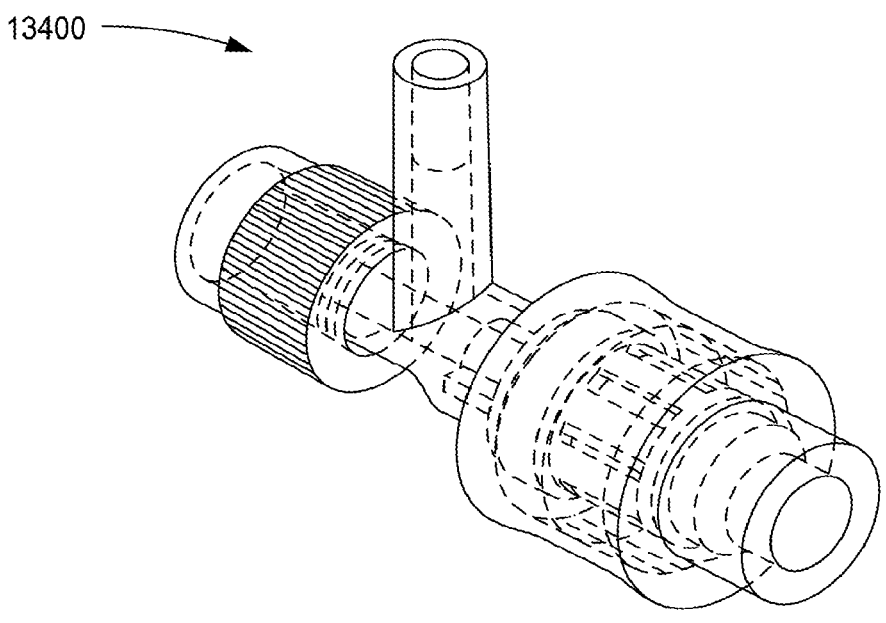
FIGS. 38-43 are various views of two-port adapters, according to various embodiments.
Figure 39:
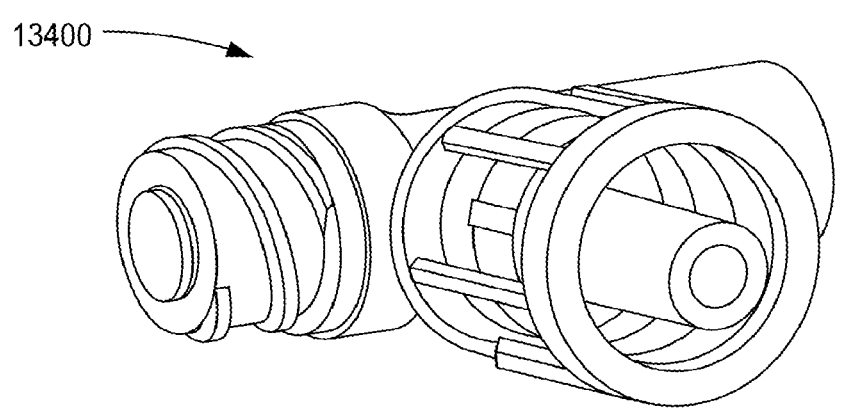
Figure 40:
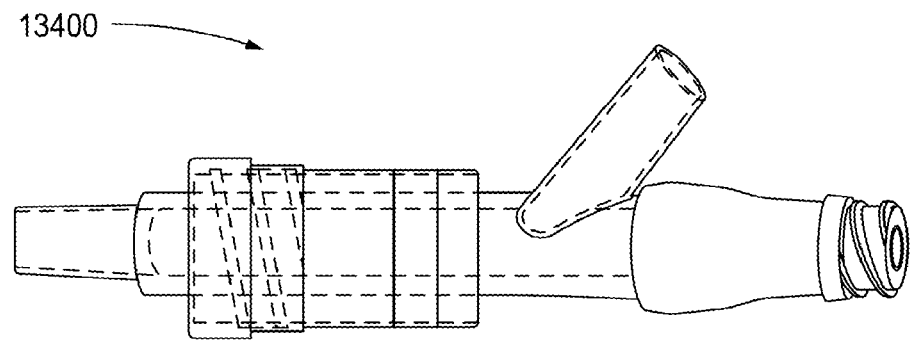
Figure 41:
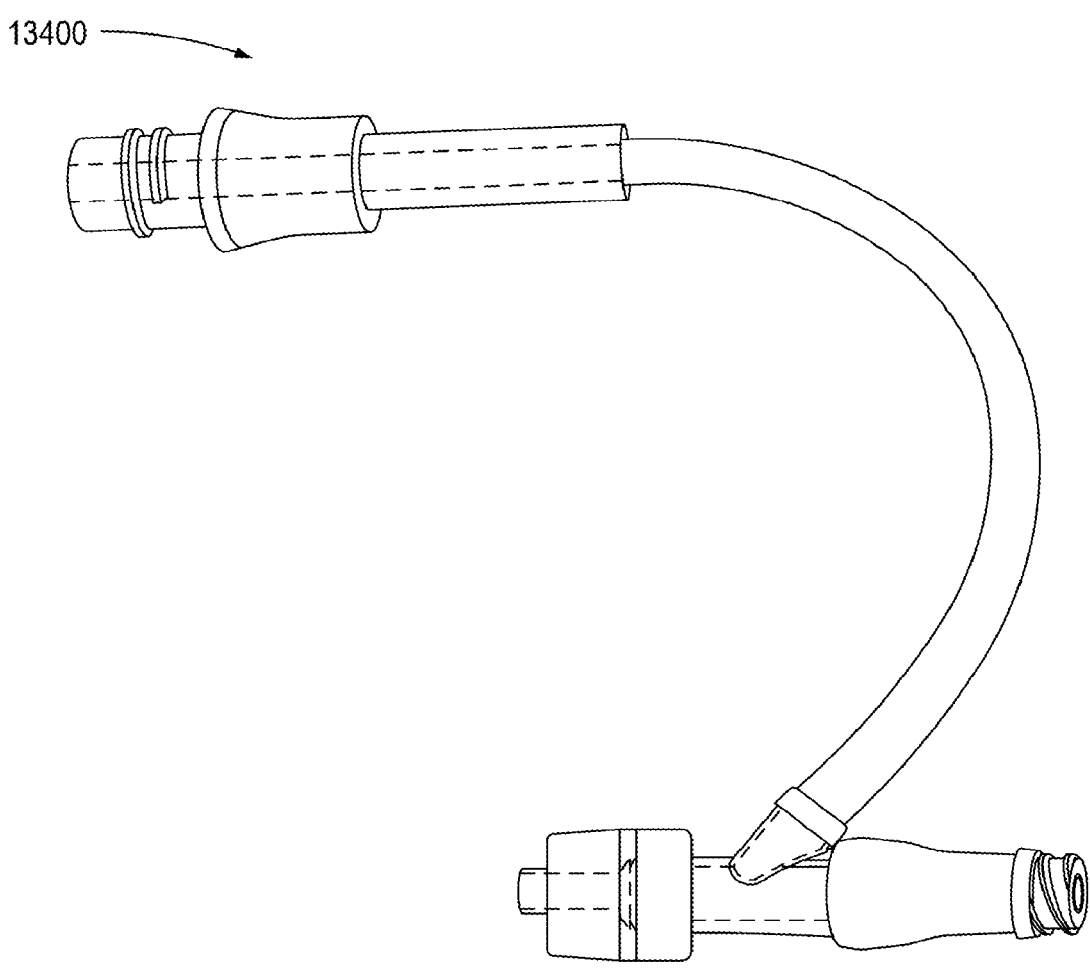
Figure 42:
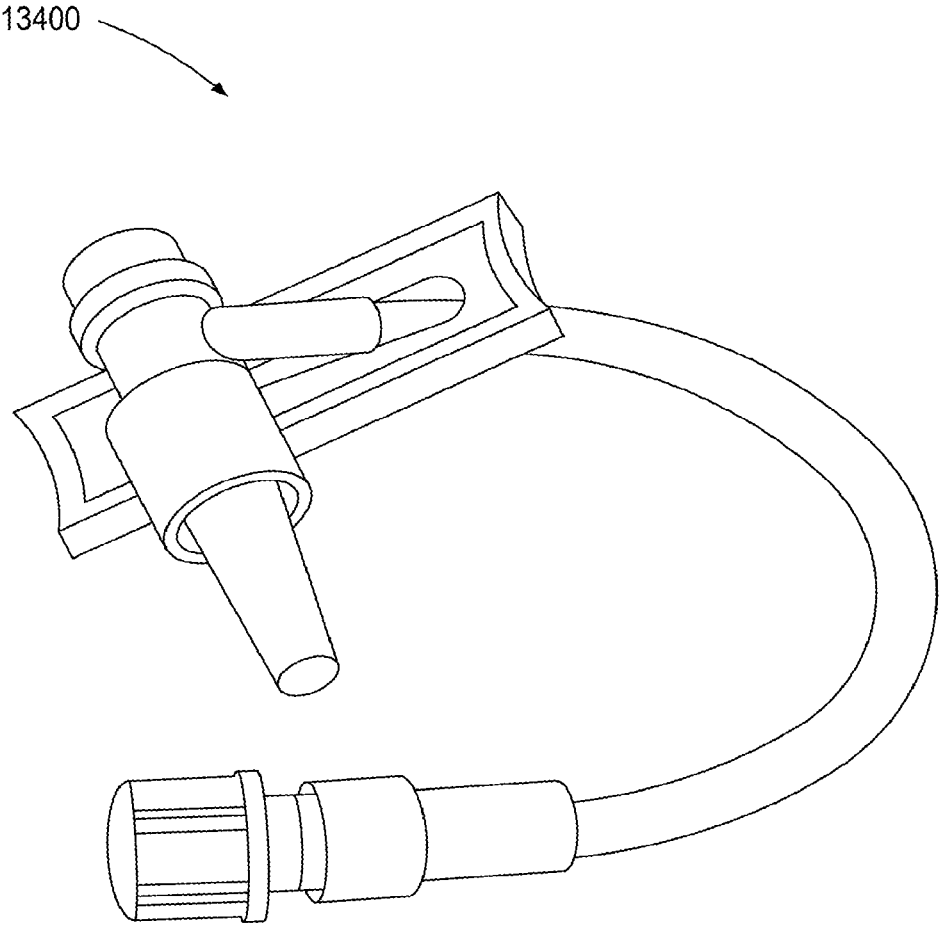
Figure 43:
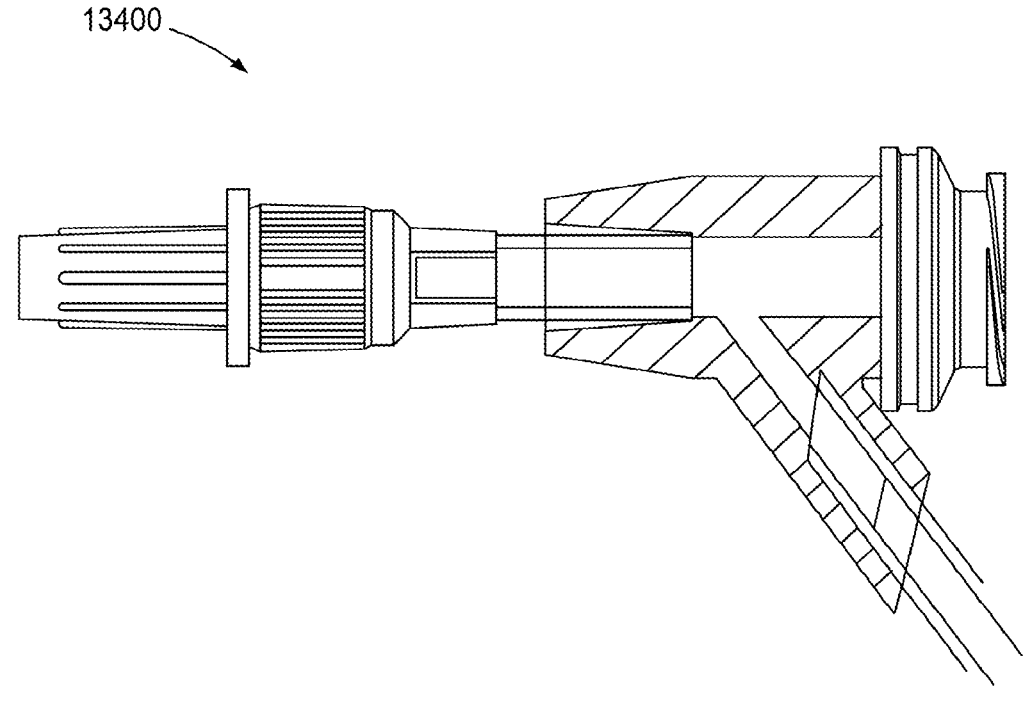

In some embodiments, the wireframe tip 12241 can be connected to a guide wire 12243 and used without an additional catheter, as shown in FIGS. 35-37. Similarly stated, the wireframe tip 12241 can be inserted into an existing peripheral intravenous line via a guide wire and without the catheter of FIG. 10. In this manner, the wireframe tip 12241 can act as a stent and support the walls of the vein such that blood can be drawn through the existing peripheral intravenous line. In such a configuration, the wireframe tip 12241 can be positioned within the existing peripheral intravenous line at any suitable location. For example, the wireframe tip can be positioned adjacent the distal end of the intravenous line.

As described above with reference to FIGS. 9-14, the blood draw apparatus 6000 can be coupled to the adapter 6400 which is further coupled to the PIV 6300. As stated, the adapter 6400 can be any suitable adapter. For example, in some embodiments, an adapter 13400 can be any of the adapters 13400 shown in FIGS. 38-43. In such embodiments, the adapters 13400 can be dual port adapters such as Y-adapters or T-adapters. In such embodiments, the adapters 13400 can include any suitable locking mechanisms, valves, coupling members, seal members, and/or the like, described herein.

Figure 44:
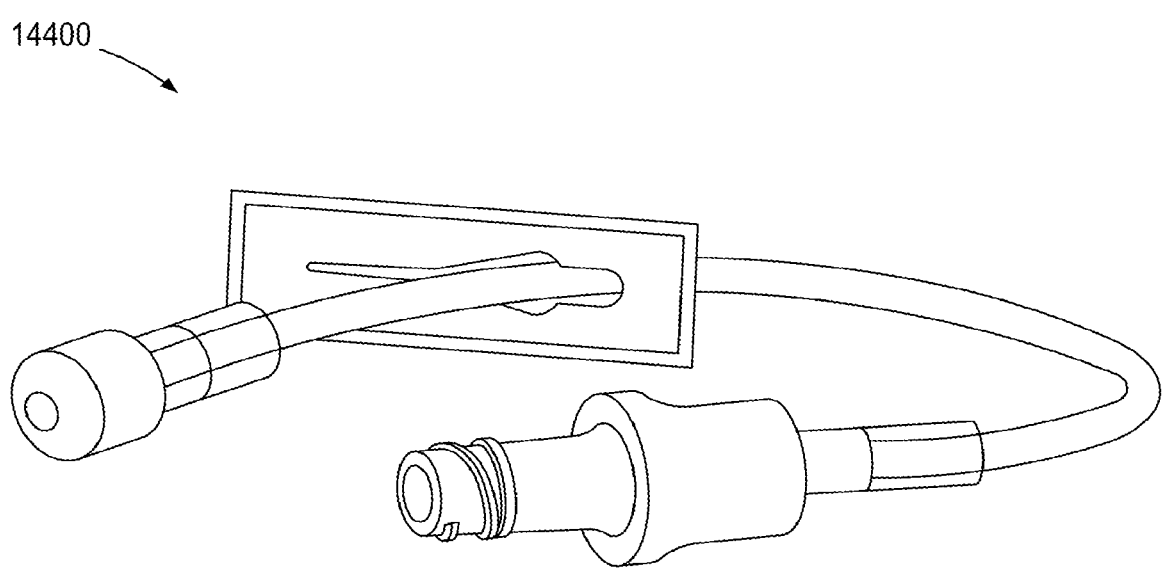
FIGS. 44 and 45 are views of single-port adapters, according to embodiments.
Figure 45:
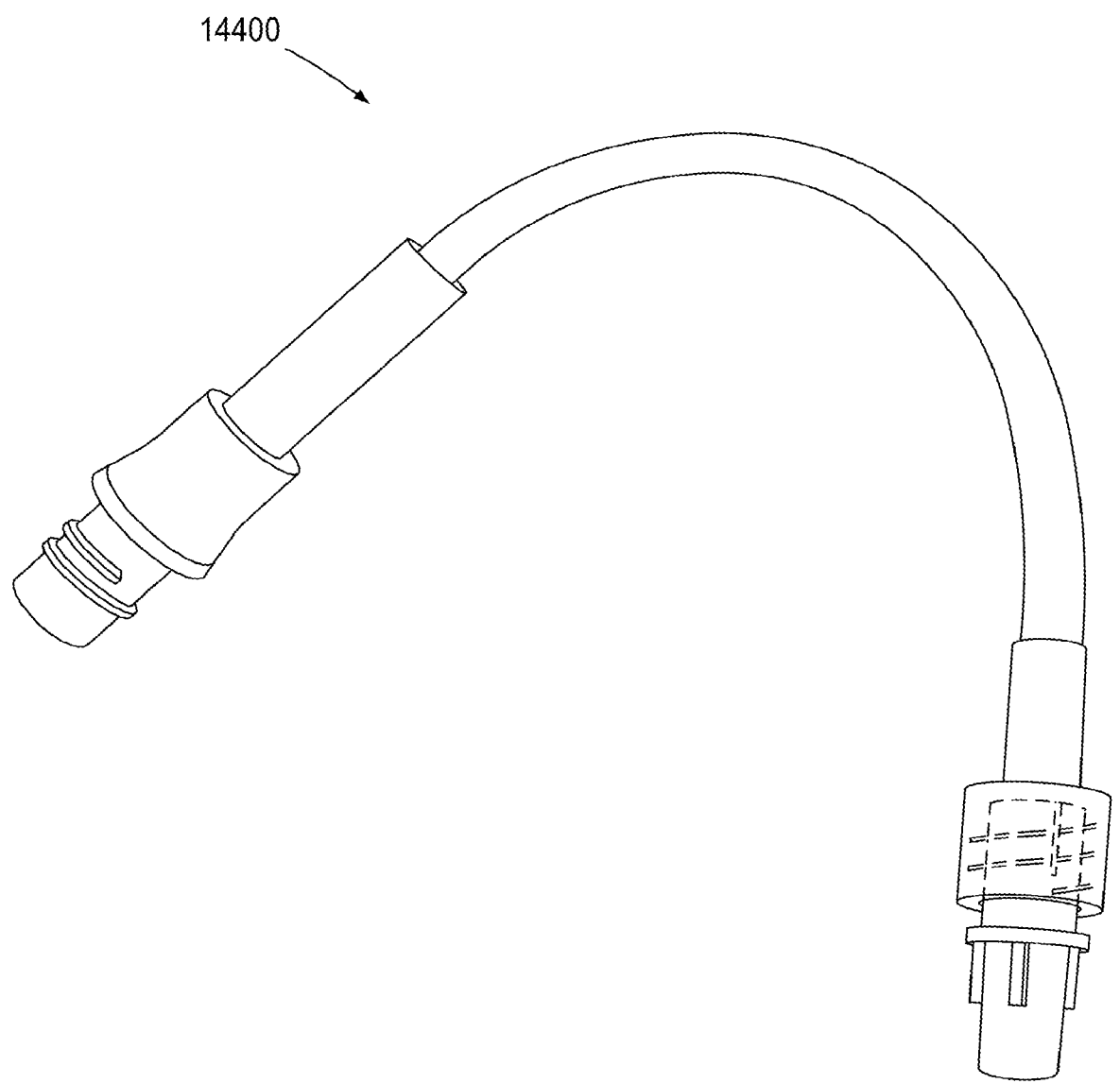

While FIGS. 38-43 illustrate dual port adapters 13400, in some embodiments, an adapter can include a single port. For example, in some embodiments, an adapter 14400 can be either adapter 14400 shown in FIGS. 44 and 45. In such embodiments, the adapter 14400 includes a single port configured to administer a fluid and/or withdraw a fluid to or from the body.

Figure 46:
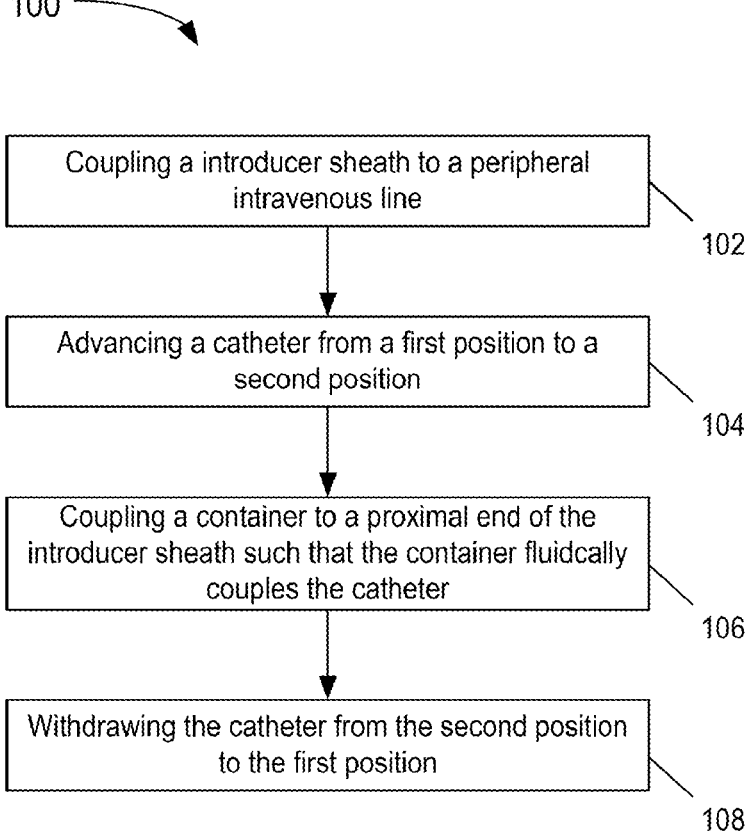
FIG. 46 is a flowchart illustrating a method of phlebotomy through a peripheral intravenous line, according to an embodiment.

FIG. 46 is a flowchart illustrating a method for drawing blood through a peripheral intravenous line. In some embodiments, a method 100 includes coupling an introducer sheath to a peripheral intravenous line (PIV), at 102. For example, in some embodiments, the introducer sheath can include a locking mechanism disposed at a distal end portion configured to engage a known PIV. In this manner, the locking mechanism can physically and fluidically couple at least a portion of the introducer with the PIV. In some embodiments, an adapter is disposed between the PIV and the locking mechanism.

The introducer sheath is configured to house, at least partially, a catheter. The method 100 further includes advancing the catheter from a first position, in which the catheter is substantially within the introducer, to a second position in which the catheter is substantially outside the introducer, at 104. For example, in some embodiments, the catheter is at least operatively coupled to an actuator such that a user can engage the actuator to move the catheter in a distal direction, relative to the introducer. Thus, the catheter moves in the distal direction and can be advanced through the locking mechanism, the adapter (if present), and the PIV. Furthermore, the catheter can be advanced such that a distal end of the catheter extends beyond the PIV and into a portion of a patient (e.g., a vein).

The method 100 includes coupling a container to a proximal end of the introducer sheath such that the container is fluidically coupled to the catheter, at 106. In some embodiments, a proximal end of the catheter includes a needle configured to pierce a portion of a fluid container, such as, for example, a Vacutainer®. In this manner, the catheter is placed in fluid communication with the fluid container. More specifically, with the catheter disposed within, for example, a vein of the patient, the fluid container is placed in fluid communication with the vein. In this manner, a desired amount of a bodily fluid (e.g., blood) can be drawn from the patient and stored in the fluid container.

With the desired amount of bodily fluid collected, the method 100 can include withdrawing the catheter from the second position towards the first position, at 108. In this manner, the catheter can be moved in the proximal direction such that the distal end of the catheter is again disposed within the introducer. With the distal end of the catheter disposed within the introducer, the introducer and/or the locking mechanism can be configured to fluidically isolate the catheter from a volume outside the introducer. Thus, the introducer and catheter can be safely disposed of without concern of spreading fluid borne pathogens.

FIGS. 47-68 illustrate an apparatus 15000 (also referred to herein as a fluid transfer device) according to another embodiment. The fluid transfer device 15000 can be any suitable shape, size, or configuration and can be coupled to a PIV (not shown in FIGS. 47-68), for example, via an adapter and/or locking mechanism. As described in further detail herein, the fluid transfer device 15000 can be manipulated to advance a catheter through an existing and/or placed PIV (i.e., when the fluid transfer device 15000 is coupled thereto) such that at least an end portion of the catheter is disposed in a distal position relative to the PIV. Moreover, with peripheral intravenous lines each having a shape, size, and/or configuration that can vary based on, for example, a manufacturer of the PIV and/or its intended usage, the fluid transfer device 15000 can be arranged to allow the fluid transfer device 15000 to be coupled to a PIV having any suitable configuration and subsequently, to advance at least a portion of a catheter through the PIV substantially without kinking, snagging, breaking, and/or otherwise reconfiguring the catheter in an undesirable manner.

Figure 47:
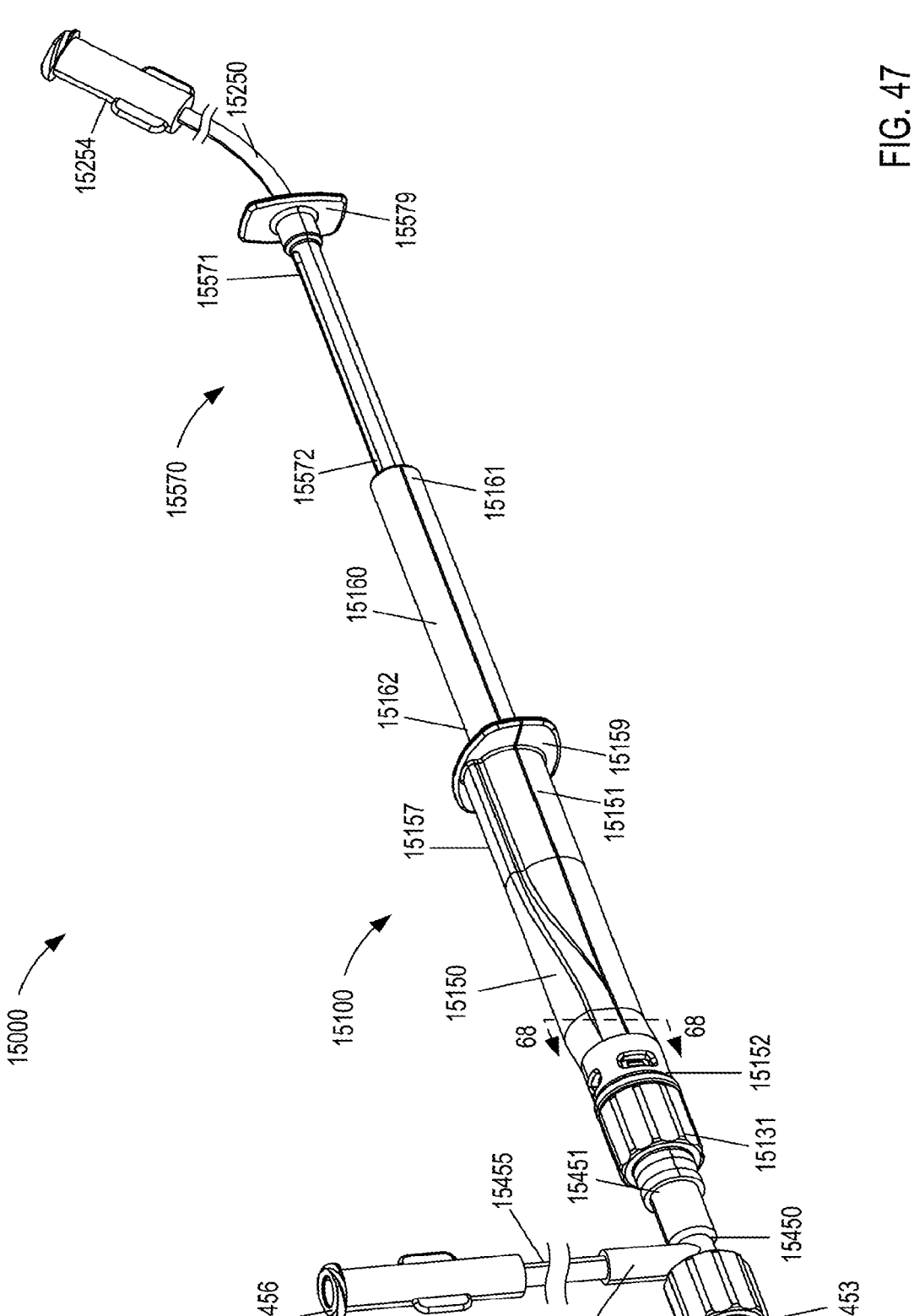
FIG. 47 is a perspective view of a fluid transfer device according to another embodiment.

As shown in FIG. 47, the fluid transfer device 15000 includes an introducer 15100, a catheter 15200, an actuator 15570, and an adapter 15450. The adapter 15450 can be any suitable adapter such as, for example, a Y-adapter or a T-adapter. For example, in this embodiment, the adapter 15450 is a T-adapter including a first port 15451 coupled to the introducer 15100, a second port 15452 coupled to a cannula 15455, which in turn, is coupled to a coupler 15456, and a third port 15453 that can be coupled to the PIV (not shown). In some embodiments, the ports 15451, 15452, and 15453 can be and/or can include a Luer Lok™ or the like that can fluidically seal the ports 15451, 15452, 15453 when the adapter 15450 is not coupled to a device (e.g., the fluid transfer device 15000, a PIV, etc.). In some embodiments, the adapter 15450 can be substantially similar to any of the adapters described in detail above (e.g., the adapters 6400, 7400, and/or 13400). As such, the adapter 15450 is not described in further detail herein.

Figure 48:
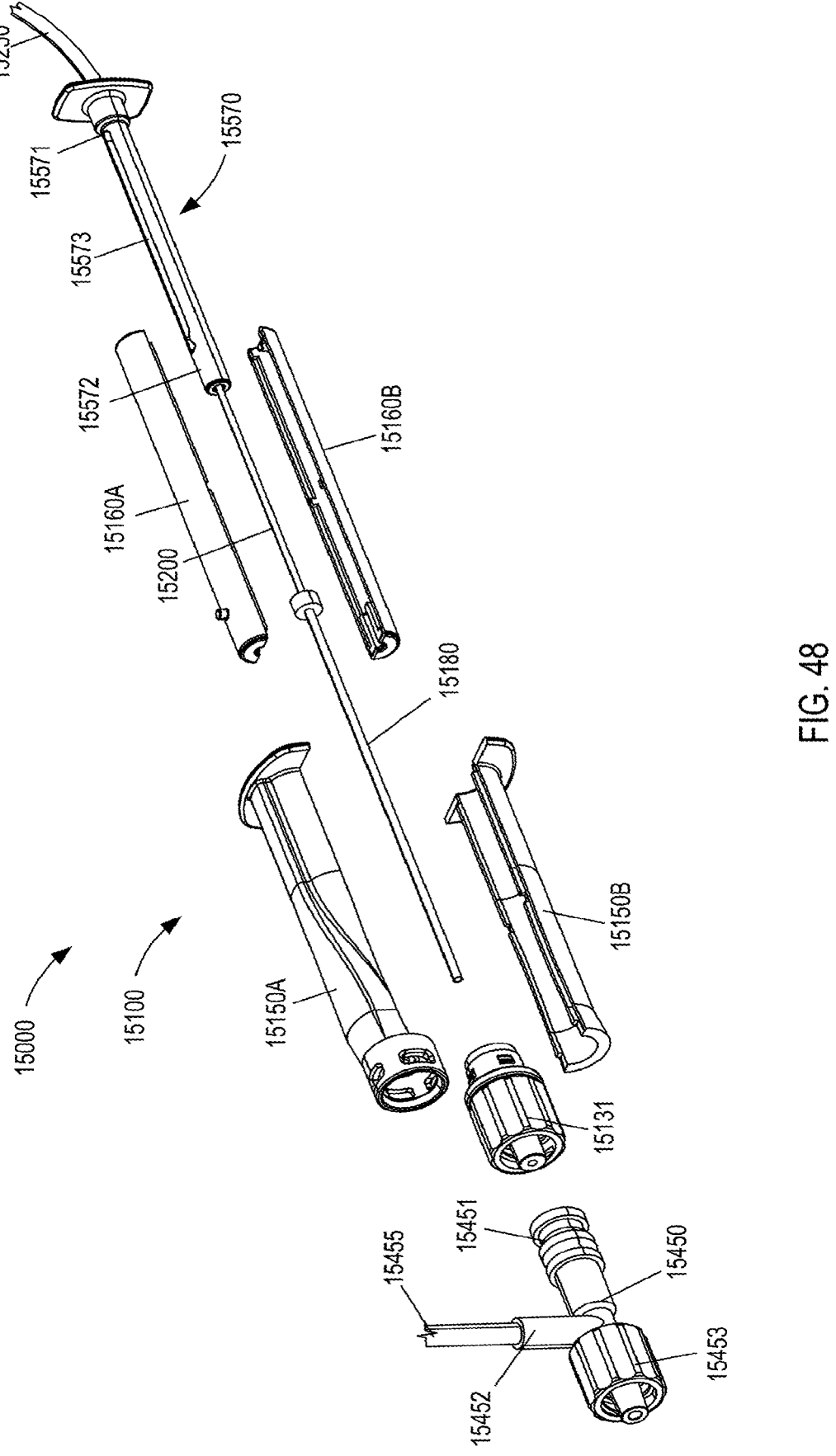
FIG. 48 is an exploded view of the fluid transfer device of FIG. 47.

The introducer 15100 of the fluid transfer device 15000 includes a first member 15150 and a second member 15160. The introducer 15100 can be any suitable shape, size, or configuration. For example, in some embodiments, the introducer 15100 can be disposed in and/or can have a substantially telescopic arrangement such as those described above with reference to the apparatus 7000 and/or 8000. In some embodiments, the introducer 15100 can have a shape that is, for example, similar to a syringe or the like. As shown in FIGS. 47-52, the first member 15150 includes a proximal end portion 15151, a distal end portion 15152, and an inner surface 15153. The inner surface 15153 defines an inner volume 15155 and a channel 15157. As shown in FIG. 48, the first member 15150 includes a first half 15150A and a second half 15150B, which can be coupled together (e.g., via ultrasonic welding, an adhesive, a mechanical fastener, one or more tabs, snaps, pins, and/or the like) to form the first member 15150. In some embodiments, coupling the first half 15150A to the second half 15150B (e.g., during a manufacturing process) to form the first member 15150 can facilitate a process of manufacturing the first member 15150. For example, in some embodiments, forming the first member 15150 from the first half 15150A and the second half 15150B can reduce undesirable variations in the shape and/or size of the inner surface 15153 (e.g., due to draft angles and/or manufacturing tolerances) during manufacturing, which can in some instances, reduce a likelihood of kinks, bends, and/or deformations of the catheter 15200 during use of the fluid transfer device 15000.

In other embodiments, a first member 15150 can be monolithically formed (e.g., via injection molding and/or any other suitable manufacturing process). That is to say, the first member 15150 can be formed from a single work piece or the like rather than two work pieces namely, the first half 15150A and the second half 15150B. Thus, when referring to features of the first member 15150, such features can be formed and/or defined by the first half 15150A, formed and/or defined by the second half 15150B, collectively formed and/or defined by the first half 15150A and the second half 15150B, or, when the first member 15150 is formed from a single work piece, formed and/or defined by a corresponding portion of the first member 15150. For example, in this embodiment, the first half 15150A and the second half 15150B collectively form the proximal end portion 15151, the distal end portion 15152, and the inner surface 15153 of the first member 15150.

Figures 49, 50:
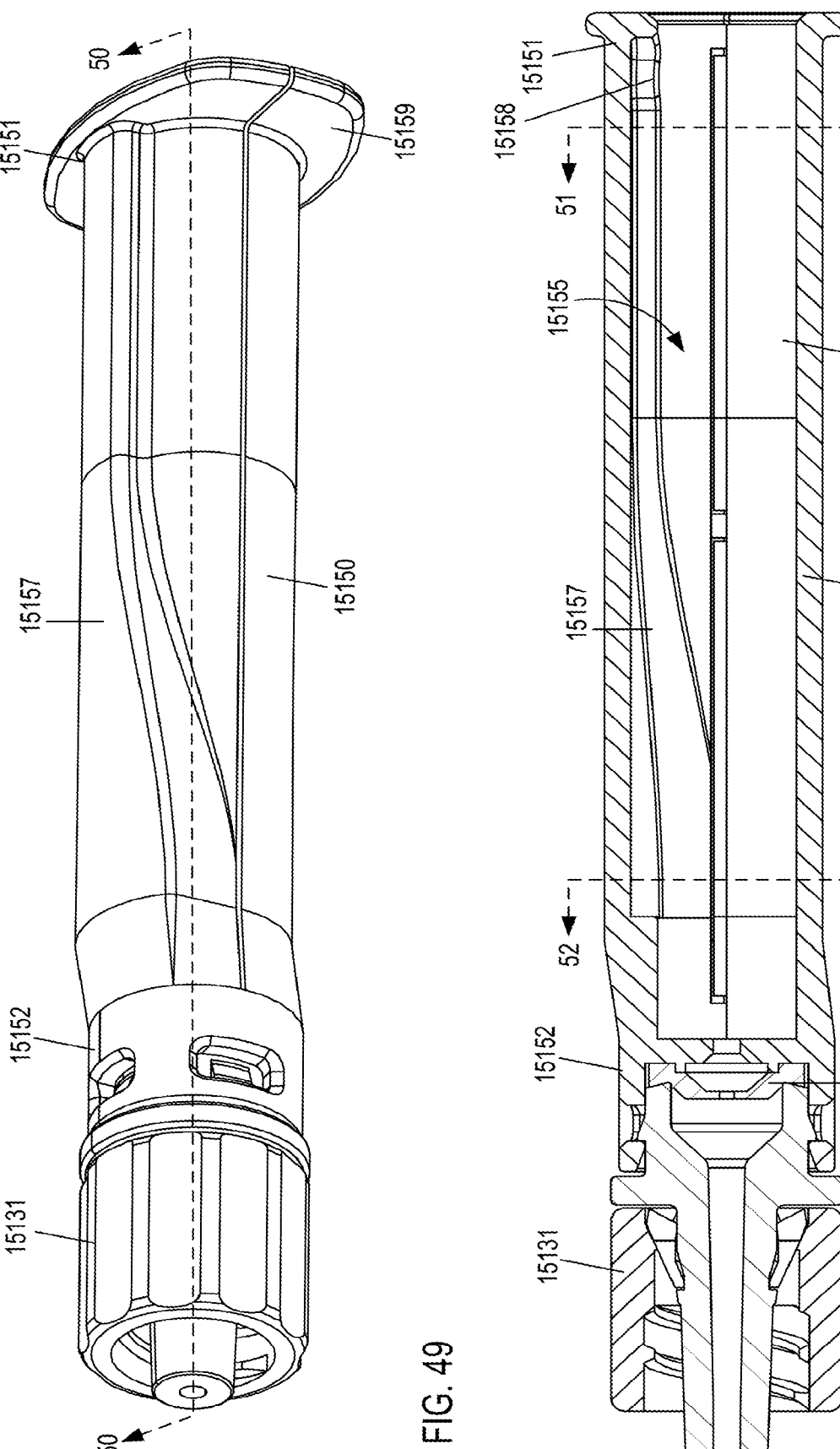
FIG. 49 is a perspective view of a first introducer member included in the fluid transfer device of FIG. 47.
FIG. 50 is a cross-sectional view of the first introducer member taken along the line 50-50 in FIG. 49.

As shown in FIGS. 49 and 50, the proximal end portion 15151 of the first member 15150 includes an engagement flange 15159 extending in a radial direction from an outer surface of the first member 15150. The arrangement of the engagement flange 15159 can allow a user to engage the engagement flange 15159 to manipulate a portion of the fluid transfer device 15000, as described in further detail herein. The distal end portion 15152 of the first member 15150 includes and/or is otherwise coupled to a locking mechanism 15131. The locking mechanism 15131 can be substantially similar to any of those described herein. In some embodiments, the locking mechanism 15131 can be a Luer Lok™ or the like. As such, a first end of the locking mechanism 15131 is coupled to the distal end portion 15152 of the first member 15150 and a second end, opposite the first end, is coupled to the adapter 15450 (e.g., the first port 15451). Alternatively, in some instances, the second end of the locking mechanism 15131 can be coupled directly to the PIV (not shown in FIGS. 47-68).

As shown in FIG. 50, the lock mechanism 15131 includes a seal member 15190 that is in contact with, for example, a distal surface of the first member 15150 to define a substantially fluid tight seal. In use, the seal member 15190 can receive a portion of the second member 15160 to allow the portion of the second member 15160 and/or the cannula 15200 to be advanced beyond the seal member 15190 in the distal direction while maintaining a substantially fluid tight seal around the portion of the second member 15160, thereby substantially preventing a backflow of fluid into the introducer 15100. The seal member 15190 can be any suitable configuration such as, for example, an O-ring, a one-way valve, a diaphragm, a self-healing diaphragm, a check valve, or any other suitable seal member such as those described herein. While shown and described as being included in the locking mechanism 15131, in some embodiments, a seal can be included in the locking mechanism 15131, the adapter 15450, and/or the first member 15150, as described above. Moreover, the seal member 15190 can contact the portion of the second member 15160 in such a manner that a friction force is defined therebetween. In some instances, the friction force is sufficient to selectively limit movement of the second member 15160 relative to the first member 15150, as described in further detail herein.

Figure 51:
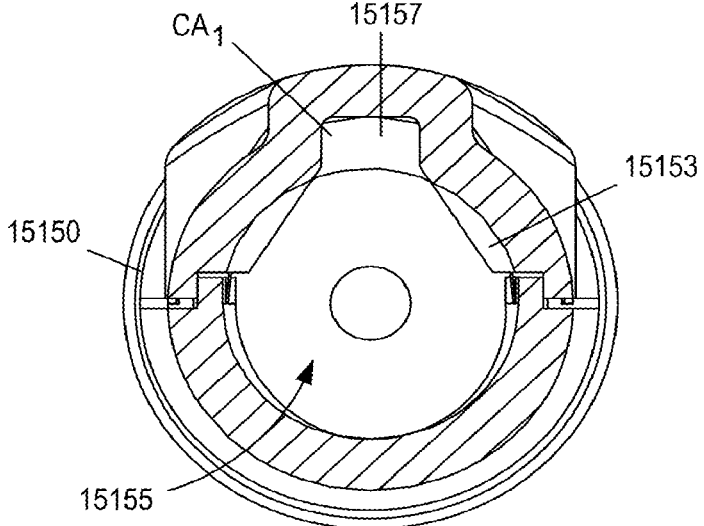
FIG. 51 is a cross-sectional view of the first introducer member taken along the line 51-51 in FIG. 50.
Figure 52:
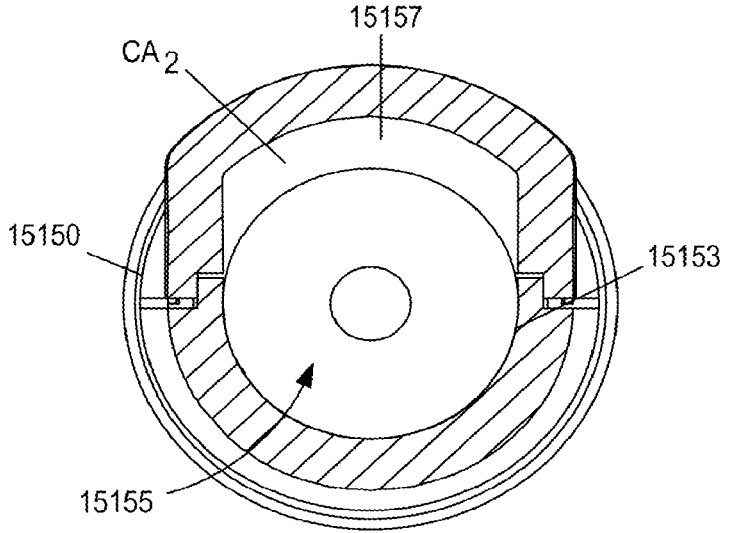
FIG. 52 is a cross-sectional view of the first introducer member taken along the line 52-52 in FIG. 50.

As shown in FIGS. 50-52, the first member 15150 includes a set of annular walls or the like, which form the inner surface 15153. The inner surface 15153 can define a cross-sectional area with any suitable shape and/or size. For example, a cross-sectional area defined by the inner surface 15153 (i.e., the cross-sectional area of the inner volume 15155) can be substantially circular with a size that is sufficient to receive at least a portion of the second member 15160, the catheter 15200, and/or the actuator 15570. Thus, the inner volume 15155 defined by the inner surface 15153 can be substantially cylindrical with a size that is sufficient to receive at least a portion of the second member 15160. That is to say, the inner surface 15153 can have a diameter and/or a perimeter that is larger than a diameter and/or perimeter of an outer surface of the second member 15160, as described in further detail herein. While shown and described as being substantially cylindrical, in other embodiments, the inner volume 15155 can have any suitable shape and/or size. For example, in some embodiments, the inner surface 15153 can define a substantially D-shaped cross-sectional area (e.g., semi-circular). In other embodiments, the inner surface 15153 can have a cross-sectional shape that is varied along a length of the first member 15150.

As described above, the inner surface 15153 defines the channel 15157. The channel 15157 extends along a length of the first member 15150 between the proximal end portion 15151 and the distal end portion 15152, as shown in FIG. 50. More particularly, the arrangement of the channel 15157 as defined by the inner surface 15153 is such that the channel 15157 does not extend through the proximal end portion 15151 or the distal end portion 15152. In other words, the channel 15157 does not extend the entire length of the first member 15150. Thus, at least a distal end portion the channel 15157 is bounded by the inner surface 15153. In addition, the channel 15157 is in fluid communication with the inner volume 15155. Said another way, the channel 15157 can be included in and/or otherwise encompassed by the inner volume 15155. Said yet another way, the inner surface 15153 can define a volume that includes a first portion (e.g., the inner volume 15155) and a second portion (e.g., the channel 15157).

As shown in FIGS. 51 and 52, the arrangement of the inner surface 15153 can be such that the channel 15157 has a first cross-sectional area $CA_1$ at or near the proximal end portion 15151 of the first member 15150 (FIG. 51) and a second cross-sectional area $CA_2$ at or near a distal end portion 15152 of the first member 15150 (FIG. 52). For example, in some embodiments, the channel 15157 can be configured to fan-out, flare, and/or otherwise widen along a length of the first member 15150 in the distal direction. As described in further detail herein, a portion of the second member 15160 can be disposed in the channel 15157 and a portion of inner surface 15153 defining the channel 15157 can define, for example, a range of motion associated with the second member 15160 relative to the first member 15150.

Figures 53, 54, 55:
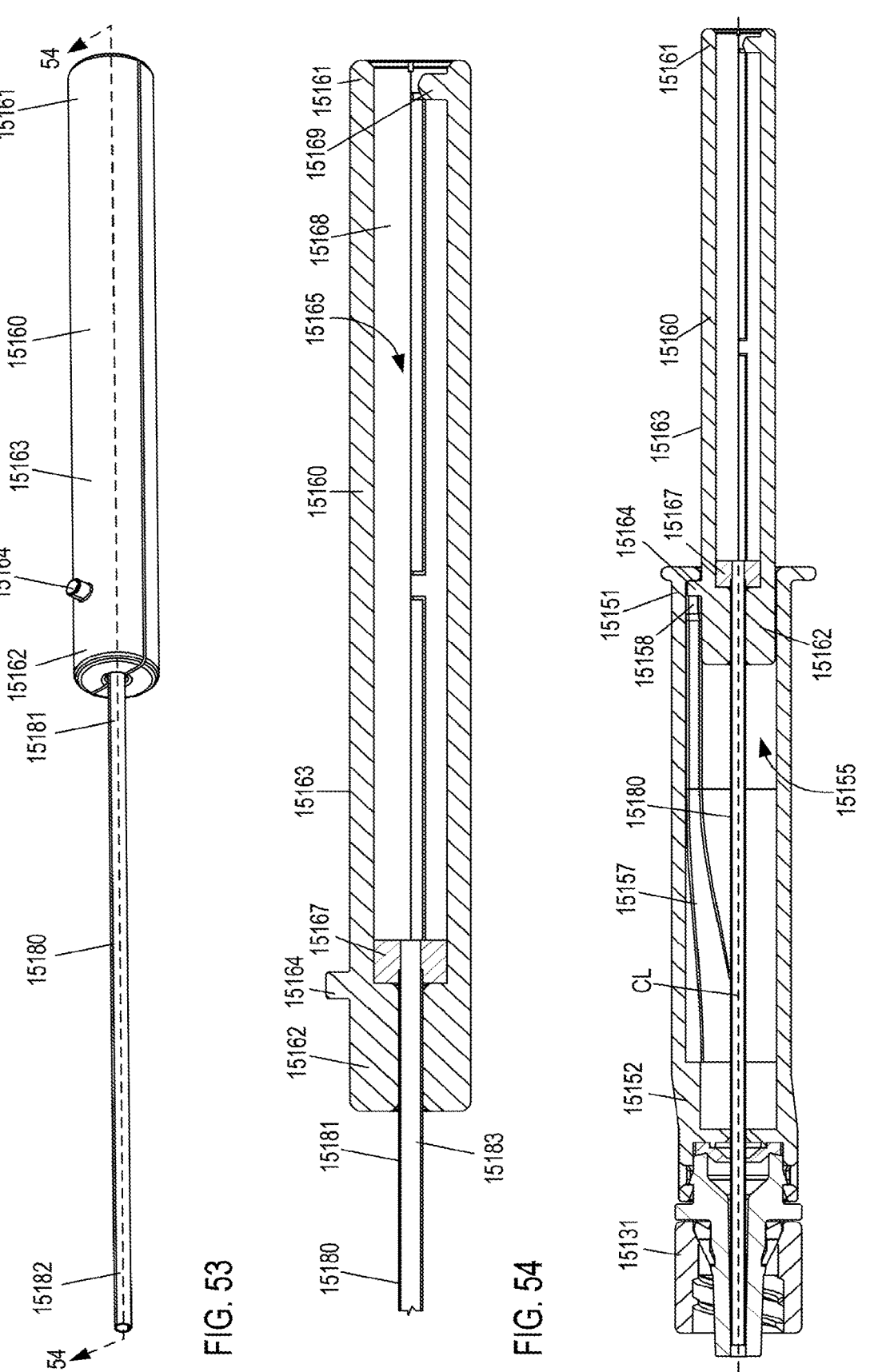
FIG. 53 is a perspective view of a second introducer member included in the fluid transfer device of FIG. 47.
FIG. 54 is a cross-sectional view of the second introducer member taken along the line 54-54 in FIG. 53.
FIG. 55 is a cross-sectional view of the first introducer member taken along the line 50-50 in FIG. 49 and the second introducer member taken along the line 54-54 in FIG. 53.

As shown in FIGS. 53 and 54, the second member 15160 of the introducer 15100 includes a proximal end portion 15161, a distal end portion 15162, an outer surface 15163 having a first protrusion 15164, and an inner surface 15168 having a second protrusion 15169. The second member 15160 also includes and/or is otherwise coupled to a guide member 15180. The second member 15160 can have any suitable shape, size, or configuration. For example, as shown in FIG. 53, the second member 15160 can have a substantially cylindrical shape. That is to say, the outer surface 15163 of the second member 15160 defines and/or has a substantially circular cross-sectional shape. In some embodiments, the size and/or shape of the second member 15160 can be associated with and/or can substantially correspond to the size and/or shape of the inner surface 15153 of the first member 15150. Thus, at least a portion of the second member 15160 can be inserted into the first member 15150 and can be movable therein between, for example, a proximal position and a distal position (e.g., a telescopic motion).

As described above with reference to the first member 15150, the second member 15160 includes a first half 15160A and a second half 15160B, which can be coupled together (e.g., via ultrasonic welding, an adhesive, a mechanical fastener, one or more tabs, snaps, pins, and/or the like) to form the second member 15160. In other embodiments, the second member 15160 can be monolithically formed (e.g., via injection molding and/or any other suitable manufacturing process). Thus, when referring to features of the second member 15160 it should be understood that such features can be formed and/or defined by the first half 15160A, formed and/or defined by the second half 15160B, collectively formed and/or defined by the first half 15160A and the second half 15160B, or, when the second member 15160 is formed from a single work piece, formed and/or defined by a corresponding portion of the second member 15160. For example, in this embodiment, the first half 15160A and the second half 15160B collectively form the proximal end portion 15161 and the distal end portion 15162 of the second member 15160.

The inner surface 15168 of the second member 15160 defines an inner volume 15165. The inner surface 15168 can define a cross-sectional area with any suitable shape and/or size. For example, a cross-sectional area defined by the inner surface 15168 (i.e., the cross-sectional area of the inner volume 15165) can have a substantially circular cross-sectional shape with a size that is sufficient to receive at least a portion of the actuator 15570 (e.g., the size is larger than a cross-sectional size of at least a portion of the actuator 15570). As shown in FIG. 54, the second member 15160 can include a seal member 15167 disposed in a distal most position within the inner volume 15165 and about a portion of the guide member 15180. As such, the seal member 15167 forms a substantially fluid tight and/or substantially hermetic seal about the guide member 15180. The seal member 15167 can be any suitable shape, size, and/or configuration. For example, in some embodiments, the seal member 15167 can be formed from a flexible material such as silicone, rubber, and/or any other suitable elastomeric material. In some embodiments, the seal member 15167 can be configured to absorb a bodily fluid that might otherwise flow in the proximal direction into the inner volume 15165 (e.g., a flow of bodily fluid substantially outside of the catheter 15200). For example, in some embodiments, the seal member 15167 can be formed from an absorbent material such as POREX® or the like. Moreover, the second protrusion 15169 extends from the inner surface 15168, for example, at or near the proximal end portion 15161 of the second member 15160. As described in further detail herein, the second protrusion 15169 can engage a portion of the actuator 15570 when the actuator 15570 is disposed within the inner volume 15165.

The first protrusion 15164 of the second member 15160 extends from the outer surface 15163 at or near the distal end portion 15162 of the second member 15160. Said another way, the first protrusion 15164 extends in a radial direction from the outer surface 15163. As such, when the second member 15160 is disposed within the inner volume 15155 of the first member 15150, the first protrusion 15164 is disposed in the channel 15157, as shown in FIG. 55.

The arrangement of the introducer 15100 is such that when the second member 15160 is moved relative to the first member 15150, the first protrusion 15164 is moved within the channel 15157. As such, the channel 15157 (and/or the portion of the inner surface 15153 defining the channel 15157) defines a range of motion for the second member 15160 relative to the first member 15150. For example, with the channel 15157 extending along the length of the first member 15150 from the proximal end portion 15151 to the distal end portion 15152, the range of motion associated with the second member 15160 as defined by the channel 15157 includes an axial motion (e.g., a distal and/or proximal direction) of the second member 15160 within the first member 15150 between its proximal position and its distal position. Similarly, the increased width associated with the second cross-sectional area $CA_2$ can define, for example, a rotational range of motion about a longitudinal centerline CL of the first member 15150 (see e.g., FIG. 55), as described in further detail herein.

In some embodiments, the range of motion associated with a rotation of the second member 15160 (also referred to herein as "rotational range of motion") is dependent on an axial position of the second member 15160 along the longitudinal centerline CL of the first member. For example, in some embodiments, the inner surface 15153 defining a portion of the channel 15157 can be, for example, relatively tapered or the like such that the rotational range of motion continuously increases until the second member 15160 is disposed in a distal position relative to the first member 15150. In other embodiments, the inner surface 15153 can include any number of steps or rings with each step or ring being associated with a portion of the channel 15157 corresponding to a discrete rotational range of motion. By way of example, the inner surface 15153 can include a first ring associated with a rotational range of motion of about 30 degrees, a second ring distally adjacent to the first ring and associated with a rotational range of motion of about 90 degrees, and a third ring distally adjacent to the second ring and associated with a rotational range of motion of about 180 degrees.

With the channel 15157 not extending through the proximal end portion 15151 or the distal end portion 15152 of the first member 15150 (as described above), the axial movement of the second member 15160 relative to the first member 15150 is limited to a length of the channel 15157. Thus, at least a portion of the second member 15160 is maintained in the inner volume 15155 and substantially prevented from being retracted therethrough. Furthermore, a portion of the inner surface 15153 defining a proximal end portion of the channel 15157 can include, for example, a rib 15158 (e.g., a ridge, a protrusion, a bump, etc.) that can be configured to at least temporarily maintain the first protrusion 15164 and thus, the second member 15160 in the proximal position relative to the first member 15150, as described in further detail herein.

Referring back to FIGS. 53 and 54, the guide member 15180 includes a proximal end portion 15181 and a distal end portion 15182. The proximal end portion 15181 is coupled to and/or otherwise extends from the distal end portion 15162 of the second member 15160. More specifically, the proximal end portion 15181 of the guide member 15180 is disposed within the seal member 15167, which in turn, is disposed in the inner volume 15165 of the second member 15160. As shown in FIG. 54, at least a portion of the seal member 15167 is disposed in a proximal position relative to the guide member 15180. In other words, the proximal end portion 15181 of the guide member 15180 does not extend through the seal member 15167 disposed within and/or coupled to the distal end portion 15162 of the second member 15160, as described in further detail herein.

In this embodiment, the guide member 15180 can be, for example, a cannula, a catheter, and/or the like. As such, the guide member 15180 defines a lumen 15183 that movably receives a portion of the catheter 15200. As described in further detail herein, the arrangement of the second member 15160 and the guide member 15180 is such that when the second member 15160 is disposed in the proximal position relative to the first member 15150, the guide member 15180 is disposed in the first member 15150 and when the second member 15160 is moved to the distal position relative to the first member 15150, the distal end portion 15182 of the guide member 15180 at least partially extends beyond, for example, a distal end of a PIV (not shown). Moreover, the second member 15160 is disposed in the inner volume

15155 of the first member 15150 in such a manner that the guide member 15180 extends through the seal member 15190. Thus, the seal member 15190 is in contact with an outer surface of the guide member 15180 to define the substantially fluid tight seal, as described above.

The guide member 15180 can be formed from any suitable material with a stiffness sufficient to allow the guide member 15180 to be passed through a hub of a PIV substantially without kinking, breaking, and/or otherwise plastically deforming. For example, in some embodiments, the guide member 15180 can be a metal hypotube or the like with a hardness (e.g., intrinsic to the material used to form the guide member 15180) and/or a stiffness (e.g., dependent on both material, size, and shape of the guide member 15180) sufficient to allow the guide member 15180 to pass through any suitable hub configuration included in a PIV as the second member 15160 is moved from the proximal position to the distal position. As described in further detail herein, the guide member 15180 can be advanced through at least a portion of an PIV so that the distal end portion 15182 is in a distal position relative to at least the hub or basket of the PIV and once placed in a desired position, the catheter 15200 can be advanced within the lumen 15183 defined by the guide member 15180 in the distal direction so that at least a portion of the catheter 15200 is disposed distal to the guide member 15180. Thus, the arrangement of the guide member 15180 and the catheter 15200 limits and/or substantially prevents a kinking, bending, breaking, pinching, and/or other form of deformation of the catheter 15200 as the catheter 15200 is moved in the distal direction.

Although the guide member 15180 is shown and described as being a cannula, catheter, and/or hypotube, in other embodiments, a guide member can be any suitable configuration. For example, in some embodiments, a guide member can be an elongate structure with a substantially V-shaped or U-shaped cross-section. Such a guide member can, for example, define a channel or the like configured to receive and/or guide a portion of a catheter. In other embodiments, the guide member 15180 can be a braided wire, a conduit, a coil, a spiral, a rail, and/or any other suitable member configured to receive and/or guide a portion of a catheter. Thus, the arrangement and/or configuration of the guide member 15180 can be associated with an amount of stiffness sufficient to allow the guide member 15180 to be passed through a PIV and/or sufficient to guide the catheter 15200 to reduce, for example, a likelihood of the catheter 15200 being kinked when being moved within the introducer 15100.

As shown in FIGS. 56-60, the actuator 15570 of the fluid transfer device 15000 includes a proximal end portion 15571 and a distal end portion 15572 and defines a slot 15573. The proximal end portion 15571 includes an engagement portion 15579 that can be substantially similar to the engagement portion 15159 of the first member 15150. For example, a user can engage the engagement portion 15579 to manipulate at least the actuator 15570 of the fluid transfer device 15000, as described in further detail herein. The proximal end 15540 is coupled to a secondary cannula 15250 that includes a coupler 15254, which in turn, is configured to be coupled to a fluid reservoir (e.g., a Vacutainer® or the like (not shown in FIGS. 47-68)). As described in further detail herein, the actuator 15570 is coupled to the catheter 15200 such that when the coupler 15254 is coupled to the fluid reservoir, the catheter 15200 is placed in fluid communication with the fluid reservoir.

Figures 56, 57, 58:
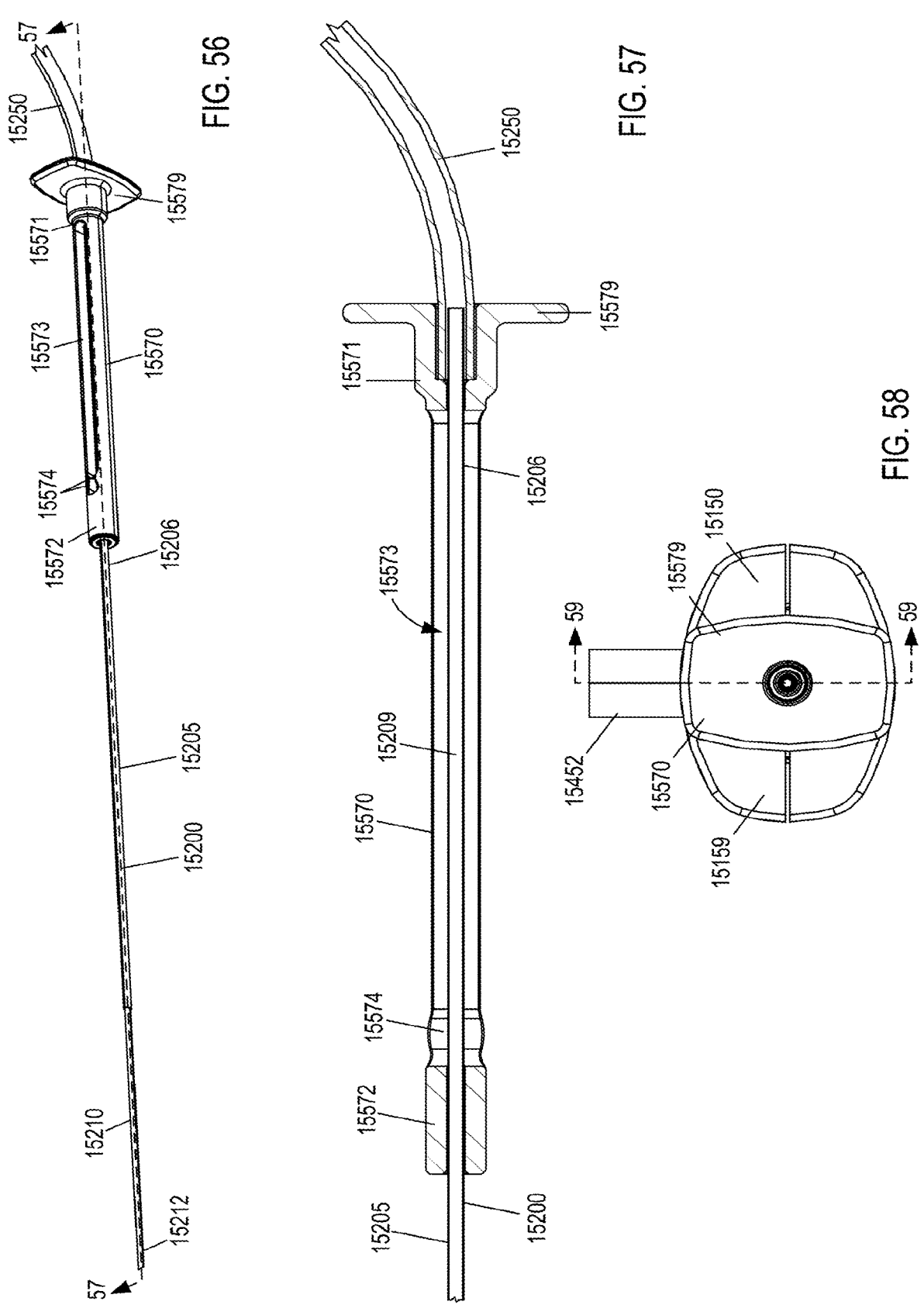
FIG. 56 is a perspective view of an actuator included in the fluid transfer device of FIG. 47.
FIG. 57 is a cross-sectional view of the actuator taken along the line 57-57 in FIG. 56.
FIG. 58 is a rear view of the fluid transfer device of FIG. 47.
Figures 59, 60:
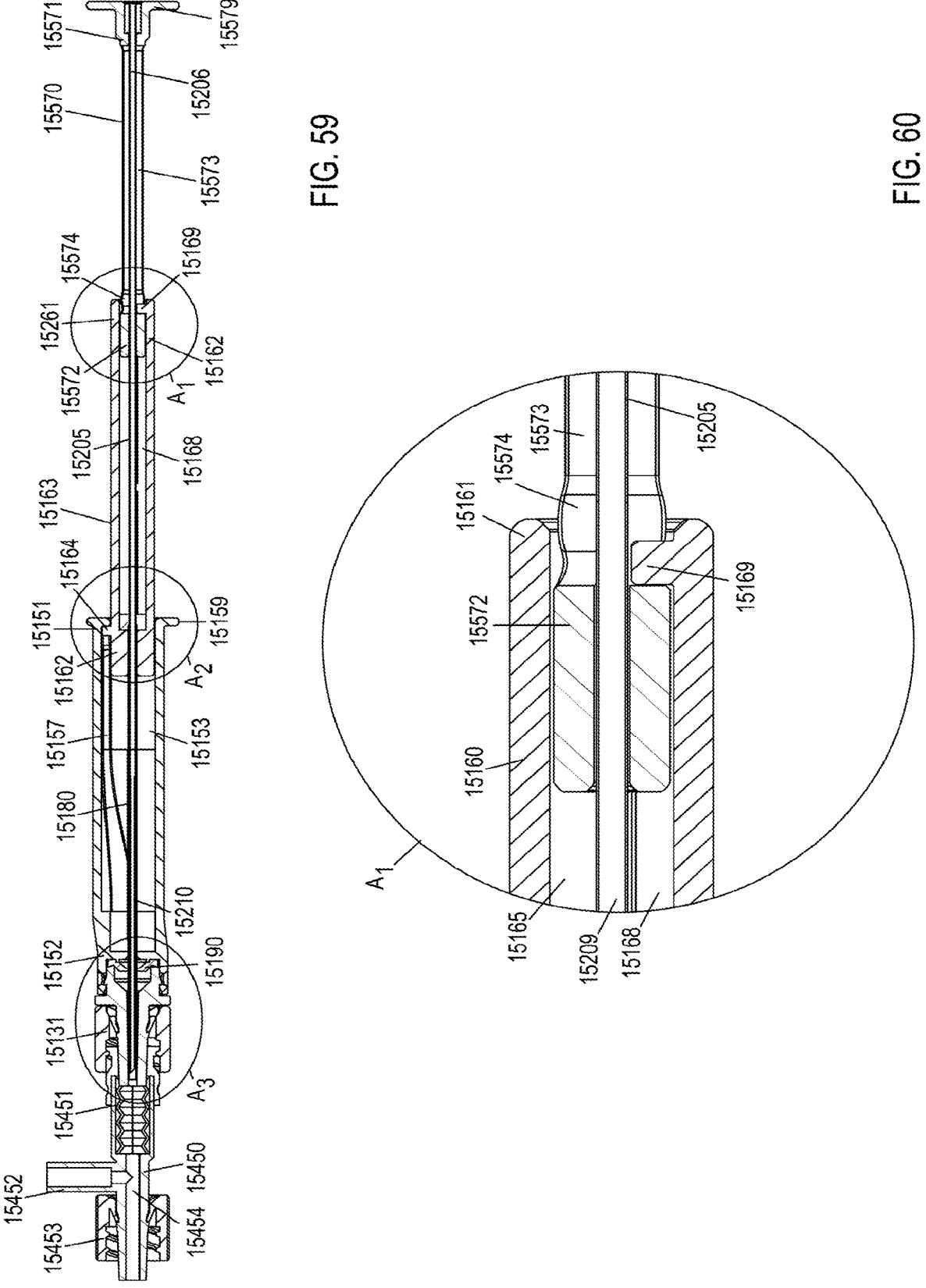
FIG. 59 is a cross-sectional view of the fluid transfer device taken along the line 59-59 in FIG. 58, in a first configuration.
FIG. 60 is an enlarged view of a portion of the fluid transfer device of FIG. 59 indicated by the region $A_1$.

The actuator 15570 can have any suitable shape, size, or configuration. For example, as shown in FIG. 56, the second member 15160 can have a substantially cylindrical shape. In some embodiments, the size and/or shape of the second member 15160 can be associated with and/or can substantially correspond to the size and/or shape of the inner surface 15168 of the second member 15160. In this manner, at least a portion of the actuator 15570 can be inserted into the inner volume 15165 defined by the second member 15160 and can be moved there in between, for example, a proximal position and a distal position (e.g., a telescopic motion). More specifically, as shown in FIGS. 59 and 60, the actuator 15570 can be disposed within the inner volume 15165 of the second member 15160 in such a manner that the second protrusion 15169 extending from the inner surface 15168 is disposed within the slot 15573 defined by the actuator 15570. Thus, as the actuator 15570 is moved in an axial motion (e.g., in the distal direction or the proximal direction) relative to the second member 15160, the second protrusion 15169 is moved within the slot 15573. As described above, in some embodiments, the actuator 15570 can be disposed between the first half 15160A and the second half 15160B of the second member 15160 prior to being coupled. Thus, the second protrusion 15169 can be inserted into the slot 15573 defined by the actuator 15570. In other embodiments, the second protrusion 15169 can be movable so as to allow the actuator 15570 to be inserted into the inner volume 15165, as described above with reference to the first member 15150.

In some embodiments, a length of the slot 15573 can define a range of motion of the actuator 15570 relative to the second member 15160. Moreover, with the slot 15573 not extending through the proximal end portion 15571 or the distal end portion 15572 of the actuator 15570 (see e.g., FIGS. 56 and 57), at least a portion of the actuator 15570 is maintained in the inner volume 15165 and substantially prevented from being retracted therethrough, as described with reference to the second member 15160). Furthermore, a surface of the actuator 15570 defining a distal end portion of the slot 15573 can include, for example, a protrusion, a ridge, a rib, a bump, etc. that can be configured to at least temporarily maintain the first protrusion 15164 in a distal position relative to the actuator 15570, as shown in FIG. 60. Thus, the actuator 15570 can be maintained in the proximal position relative to the second member 15160 prior to use, as described in further detail herein.

The actuator 15500 is coupled to the catheter 15200 and is configured to move the catheter 15200, relative to the introducer 15100, between a first configuration and a second configuration, as described in further detail herein. The catheter 15200 of the fluid transfer device 15000 has a proximal end 15206 and a distal end 15212 and defines a lumen 15209 therethrough (see e.g., FIGS. 56-62). As described above with reference to FIG. 5, the catheter 15200 includes a first portion 15205 (e.g., a proximal portion) having a first diameter and a second portion 15210 (e.g., a distal portion) having a second diameter, smaller than the first (see e.g., FIG. 56). In some embodiments, the diameter of the catheter 15200 at the second portion 15210 can, for example, facilitate the insertion of the catheter 15200 into the peripheral intravenous line, as described in further detail herein. In some embodiments, the catheter 15200 can be between a 16-gauge and 26-gauge and have a Shore durometer of about 20 Shore A to about 95 Shore D. In other embodiments, the catheter 15200 has a Shore durometer of about 20 Shore A to 50 Shore D. In still other embodiments, the catheter 15200 has a Shore durometer of about 70 Shore D to 85 Shore D.

In some embodiments, the first portion 15205 of the catheter 15200 can have a Shore durometer that is greater than a Shore durometer of the second portion 15210. For example, in some embodiments, the first portion 15205 can be formed from a first material or first blend of materials and the second portion can be formed from a second material or second blend of materials having a durometer less than a durometer of the first material or first blend of materials. In some embodiments, the first portion 15205 and the second portion 15210 can be, for example, co-extruded. In other embodiments, the first portion 15205 can be, for example, over-molded about a portion of the second portion 15210. In still other embodiments, the second portion 15210 can be formed by drawing an end of the first portion 15205. As such, the first portion 15205 can have a stiffness and/or durometer that is sufficient to inhibit a kinking, a pinching, a breaking, and/or an undesirable plastic deformation of the first portion 15205 while being advanced, for example, through the introducer 15100, as described in further detail herein. The second portion 15210 can have a stiffness and/or durometer that is less than the stiffness and/or durometer of the first portion 15210 and as such, can be configured to bend, flex, elastically deform, and/or otherwise reconfigure, which, in some instances, can reduce a likelihood of the second portion 15210 puncturing a vascular tissue when disposed therein and/or allow the second portion 15210 to be advanced through a kink, bend, turn, valve, and/or obstruction in, for example, a lumen defined by a PIV, as described in further detail herein.

The first portion 15205 of the catheter 15200 is coupled to the actuator 15570. More specifically, as shown in FIG. 57, the first portion 15205 of the catheter 15200 extends a length of the actuator 15570 such that the proximal end 15206 of the catheter 15200 is disposed at or near the proximal end portion 15571 of the actuator 15570. In this manner, the lumen 15209 defined by the catheter 15200 is placed in fluid communication with the secondary catheter 15250, as described in further detail herein. The second portion 15210 of the catheter 15200 can be arranged in any suitable manner. For example, in some embodiments, the distal end 15212 of the catheter 15200 (i.e., disposed at an end of the second portion 15210) can include a substantially open end-surface configured to place the lumen 15209 in fluid communication with, for example, a vein. In some embodiments, the distal end 15212 can include the open end-surface and any number of openings disposed on the side (e.g., circumference) of the catheter 15200, as described above.

Figure 62:
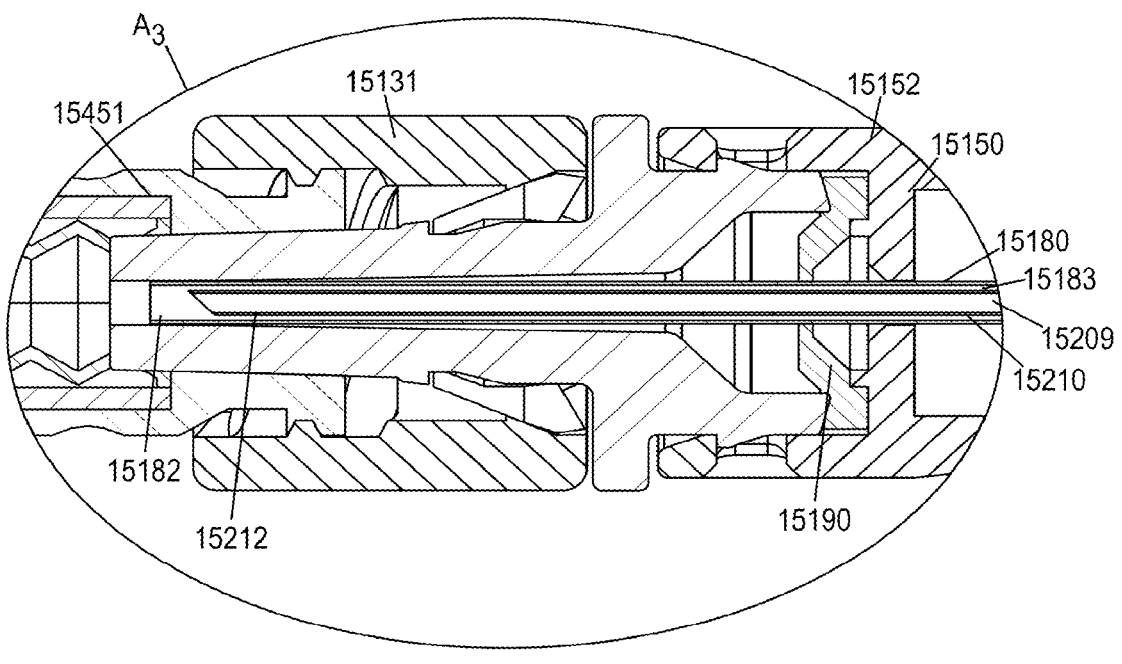
FIG. 62 is an enlarged view of a portion of the fluid transfer device of FIG. 59 indicated by the region $A_3$.

As shown in FIG. 62, in this embodiment, the distal end 15212 of the catheter 15200 is angled or beveled. In some instances, a beveled distal end 15212 can facilitate the advancement of the catheter 15200 through a kink or bend, for example, by rotating the catheter 15200 to align a bevel angle with a kink angle or the like. In other embodiments, the distal end 15212 can be any suitable configuration such as, for example, substantially flat, bullet-shaped, conical, bulbous, or the like. In still other embodiments, the distal end 15212 can be substantially open (as shown in FIG. 62) and can include one or more slits, cuts, grooves, channels, and/or the like that substantially traverse a distal surface of the distal end 15212. In such embodiments, the slits can introduce a discontinuity in and/or along a portion of the distal end 15212, which in some embodiments can decrease a stiffness of the distal end 15212 by allowing, for example, an elastic deformation of the distal end 15212. In some instances, an elastic deformation (i.e., non-permanent) of the distal end 15212 can facilitate the advancement of the catheter 15200 past and/or through kinks, bends, corners, etc. within a vascular structure, a portion of the PIV, and/or the like.

Figure 61:
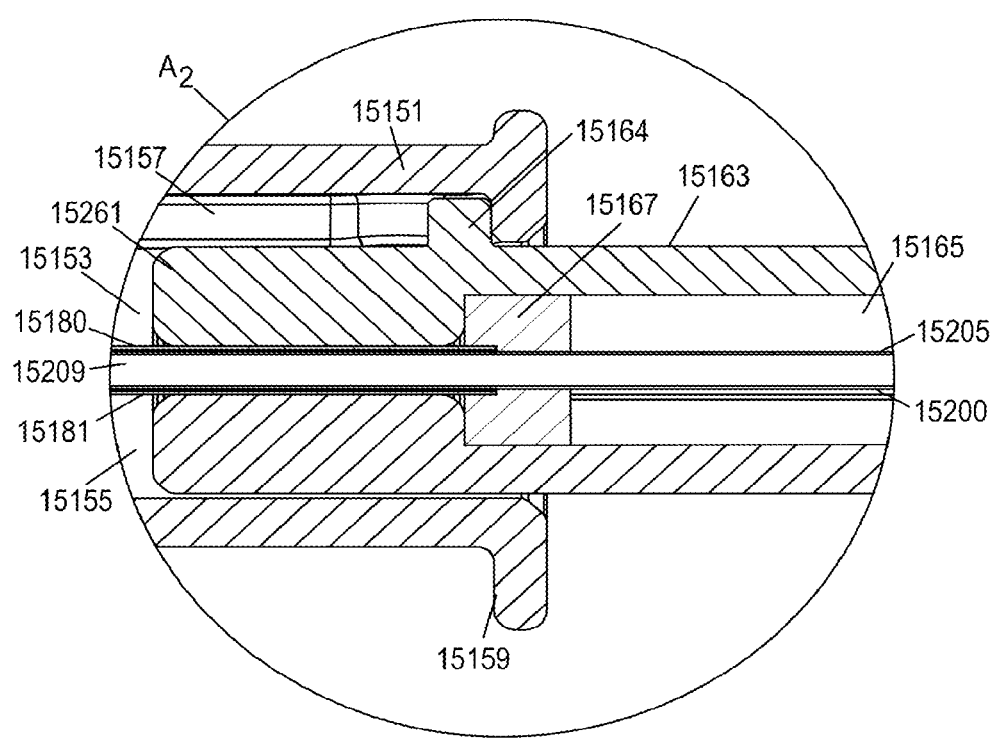
FIG. 61 is an enlarged view of a portion of the fluid transfer device of FIG. 59 indicated by the region $A_2$.

As shown in FIGS. 60-62, the arrangement of the actuator 15570 and the catheter 15200 is such that when the actuator 15570 is disposed within the second member 15160 of the introducer 15100 at least a portion of the catheter 15200 is disposed in the guide member 15180. More specifically, when the actuator 15570 is disposed in the proximal position relative to the second member 15160, the second portion 15210 of the catheter 15200 is disposed in the guide member 15180. When the actuator 15570 is moved to the distal position relative to the second member 15160, the second portion 15210 of the catheter 15200 at least partially extends beyond the distal end portion 15182 of the guide member 15180, as described in further detail herein.

Expanding further, a portion of the catheter 15200 is disposed in and extends through the seal member 15167 of the second member 15160. As such, an outer surface of a portion of the catheter 15200 that is disposed in the seal member 15167 and that is proximal to the guide member 15180 is in contact with the seal member 15167 and as such, the seal member 15167 forms a substantially fluid tight seal with the outer surface of that portion of the catheter 15200. Thus, with the catheter 15200 disposed in the guide member 15180 and the seal member 15167 forming a substantially fluid tight seal with the distal end portion 15181 of the guide member 15180 and the portion of the catheter 15200, the seal member 15167 inhibits and/or substantially prevents a bodily fluid inside of the guide member 15180 but outside of the catheter 15200 from flowing into a volume proximal to the seal member 15167. Simply stated, the seal member 15167 can engage the guide member 15180 and the catheter 15200 to inhibit bodily fluid from leaking into a volume proximal to the seal member 15167.

As shown in FIGS. 59-60, prior to use, the fluid transfer device 15000 can be disposed in a first configuration (e.g., an expanded configuration), in which the second member 15160 is disposed in its proximal position relative to the first member 15150 and the actuator 15570 is disposed in its proximal position relative to the second member 15160. In this manner, the guide member 15180 is disposed within the first member 15150 of the introducer 15100 and at least the second portion 15210 of the catheter 15200 is disposed within the guide member 15180. Expanding further, as shown in FIG. 59, the catheter 15200 is at least partially disposed in the introducer 15100 when the fluid transfer device 15000 is in the first configuration. In some embodiments, the inner volume 15165 of the second member 15160 and the inner volume 15155 of the first member can be substantially fluidically sealed such that the inner volumes 15165 and 155 are each substantially sterile. As a result, at least a portion of the catheter 15200 is maintained in a substantially sterile environment prior to use.

While the first portion 15205 of the catheter 15200 is shown, for example, in FIG. 58 as extending through the slot 15573 of the actuator 15570 and thus, being exposed to an ambient environment, in other embodiments, the actuator 15570 and/or catheter 15200 can include a bag, a cover, a wrapper, a sleeve, and/or the like that can be disposed about the portion of the catheter 15200 that extends through the slot 15573 of the actuator 15570 to maintain the portion of the catheter 15200 in a substantially sterile environment. Thus, the first portion 15205 and the second portion 15210 can be substantially sterile prior to use. In other embodiments, the second member 15160 of the introducer 15100 can include, for example, a sterilization member (e.g., a sponge, a wipe, a seal, etc.) disposed within the inner volume 15160 that can be configured to contact an outer surface of the catheter 15200, thereby sterilizing a portion of the catheter 15200 when the catheter 15200 is moved relative to the second member.

While in the first configuration, a user (e.g., a phlebotomist) can manipulate the fluid transfer device 15000 to couple the first member 15150 of the introducer 15100 to the adapter 15450 (see e.g., FIG. 59). In other embodiments, the fluid transfer device 15000 can be, for example, pre-assembled with the adapter 15450. In still other embodiments, the fluid transfer device 15000 can be used without the adapter 15450. In this embodiment, the locking mechanism 15131 disposed at the distal end portion 15152 of the first member 15150 is coupled to the first port 15451 of the adapter 15450. Although not shown in FIGS. 59-68, the third port 15453 of the adapter 15450 can be coupled to a PIV. As a result, the introducer 15100 is coupled (e.g., indirectly via the adapter 15450 or directly when used without the adapter 15450) to the PIV. Although not shown in FIGS. 59-68, the coupler 15254 disposed at the end of the secondary cannula 15250 can be coupled to a fluid reservoir or the like to place the lumen 15209 of the catheter 15200 in fluid communication with the fluid reservoir.

Once coupled to the PIV and the fluid reservoir, the user can engage the engagement portion 15159 of the first member 15150 and the engagement portion 15579 of the actuator 15570 to exert a force on the actuator 15579. More particularly, by engaging the engagement portion 15159 of the first member 15150, a portion of the force exerted on the actuator 15579 that would otherwise be exerted on the PIV (e.g., via the introducer 15100 and the adapter 15450) can be reduced. Said another way, the user can exert a reaction force on the engagement portion 15159 of the first member 15150 in response to the force applied to the actuator 15570 which is sufficient to reduce and/or substantially eliminate a force that would otherwise be transmitted to and exerted on the PIV.

Figures 63, 64:
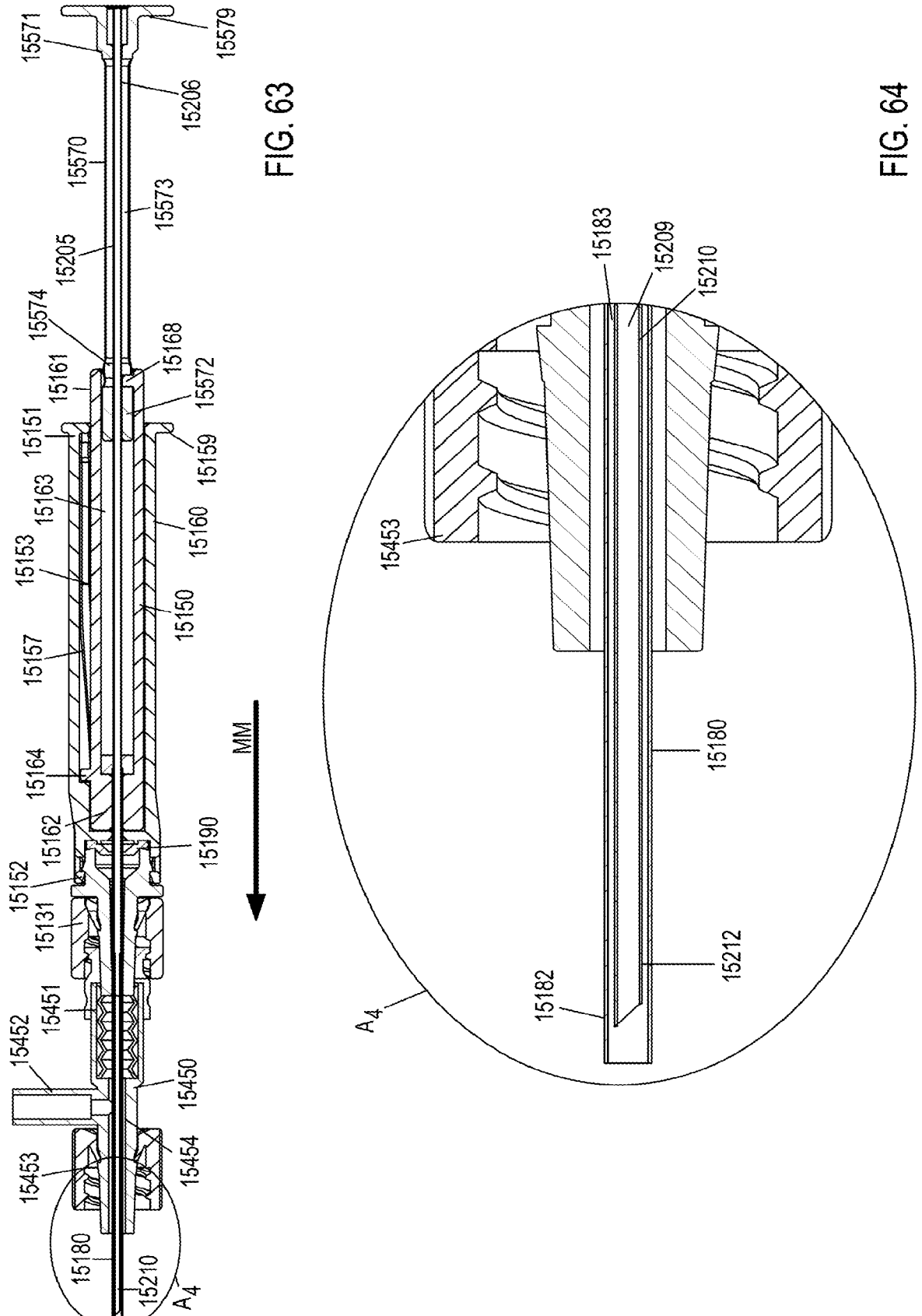
FIG. 63 is a cross-sectional view of the fluid transfer device taken along the line 59-59 in FIG. 58, in a second configuration.
FIG. 64 is an enlarged view of a portion of the fluid transfer device of FIG. 63 indicated by the region $A_4$.

The force exerted on the engagement portion 15579 of the actuator 15570 moves the actuator 15570 and the second member 15160 in the distal direction relative to the first member 15150, thereby placing the fluid transfer device 15000 in a second configuration, as indicated by the arrow MM in FIG. 63. More specifically, the actuator 15570 moves the second member 15160 from its proximal position to its distal position relative to the first member 15150, while the actuator 15570 remains in a relatively fixed position (e.g., its proximal position) relative to the second member 15160. For example, as described above, a portion of the inner surface 15153 defining a proximal end portion of the channel 15157 can include, for example, a protrusion, a ridge, a rib, a bump, etc. that can be configured to at least temporarily maintain the first protrusion 15164 and thus, the second member 15160 in the proximal position relative to the first member 15150. Similarly, the rib 15574 of extending from a surface of the actuator 15570 that defines the slot 15573 at least temporarily maintains the second protrusion 15169 in a distal position relative to the actuator 15570 and thus, the actuator 15570 is at least temporarily maintained its proximal position relative to the second member 15160.

As such, the ribs 15158 and 15574 narrow a portion of the channel 15157 and the slot 15573, respectively, to a width smaller than a width of the first protrusion 15164 and the second protrusion 15169, respectively. Thus, the second member 15160 can be maintained substantially in the proximal position until a force is applied (e.g., either directly or indirectly) to the second member 15160 that is sufficient to move the first protrusion 15164 through the narrowed portion of the channel 15157 (e.g., associated with the ribs 15158). Thus, in response to a force the first protrusion 15164 can exert a portion of the force on the ribs 15158 of the inner surface 15153, which in turn, can deform, bend, flex, and/or reconfigure the inner surface 15153 a sufficient amount to allow the first protrusion 15164 to pass therethrough (and/or to otherwise overcome a friction force therebetween). In a similar manner, the actuator 15570 can be maintained substantially in the proximal position until a force is applied on the actuator 15570 that is sufficient to move the second protrusion 15169 through the narrowed portion of the slot 15573 (e.g., associated with the ribs 15574). Thus, in response to a force the second protrusion 15169 can exert a portion of the force on the ribs 15574 of the actuator 15570, which in turn, can deform, bend, flex, and/or otherwise reconfigure a surface of the actuator 15570 a sufficient amount to allow the second protrusion 15169 to pass therethrough (and/or to otherwise overcome a friction force therebetween).

As shown in FIG. 63, the actuator 15570 and the second member 15160 are collectively moved relative to the first member 15150 in response to the applied force on the engagement portion 15579 of the actuator 15570. As such, a portion of the force moves the first protrusion 15164 past and/or through the ribs 15158 extending from the inner surface 15153 of the first member 15150, while the ribs 15574 of the actuator 15570 retain the second protrusion 15169 in a substantially fixed position. Thus, a force sufficient to move the second member 15160 relative to the first member 15150 is less than a force sufficient to move the actuator 15570 relative to the second member 15160. Such an arrangement can, for example, ensure that the second member 15160 is relative to the first member 15150 prior to the actuator 15570 being moved relative to the second member 15160. In some embodiments, the movement of the first protrusion 15164 past the ribs 15158 can be, for example, associated with and/or otherwise result in an indicator such as a haptic, tactile, visual, and/or auditory output. For example, in some embodiments, an indicator can be an auditory output such as a "click." In other embodiments, an indicator can be a visual output such as indicia, markings, a status window, a change in color of a status member, a digital output to be presented on a display, and/or the like.

As shown in FIG. 64, the movement of the second member 15160 to the distal position relative to the first member 15150 advances the guide member 15180 (coupled thereto) in the MM direction to a position in which at least the distal end portion 15182 of the guide member 15180 is disposed in and extends past an end of the PIV. More specifically, as the second member 15160 is moved to its distal position, the guide member 15180 is concurrently advanced through a port or "basket" of the PIV (not shown). As described above, the guide member 15180 is configured to have a stiffness and/or is formed from a material(s) with a hardness or durometer that is sufficient to pass through the port of the PIV substantially without kinking, breaking, bending, plastically deforming (e.g., permanently deforming), etc. Moreover, the guide member 15180 can have a length and hardness that is sufficient to pass through any suitable PIV to dispose at least the distal end portion 15182 in a distal position relative to the end of the PIV. In other words, the guide member 15180 can be arranged such that when the second member 15160 is in its distal position relative to the first member 15150, the distal end portion 15182 of the guide member 15180 is disposed in a vascular structure and at least partially outside of the PIV. Furthermore, with the actuator 15570 maintained in a relatively fixed position relative to the second member 15160, the second portion 15210 of the catheter 15200 is maintained within the lumen 15183 defined by the guide member 15180, as shown in FIG. 64.

With the second member 15160 in its distal position, the applied force exerted on the engagement portion 15579 moves the actuator 15570 from its proximal position to its distal position relative to the second member 15160. For example, the second member 15160 can be moved through its range of motion (e.g., defined at least in part by the channel 15157) to be disposed in its distal most position and as such, a portion of the applied force that was exerted to move the second member 15160 relative to the first member 15150 is instead substantially exerted on the actuator 15570. As such, the force exerted on the actuator 15570 can be sufficient to move the second protrusion 15169 past the ribs 15574 disposed in the slot 15573 and as a result, the actuator 15570 is moved from its proximal position to its distal position relative to the second member 15160, as indicated by the arrow NN in FIG. 65. In some embodiments, the movement of the actuator 15570 from its proximal position to its distal position can be associated with and/or otherwise result in an indicator such as a haptic, tactile, visual, and/or auditory output, as described above.

Figures 65, 66:
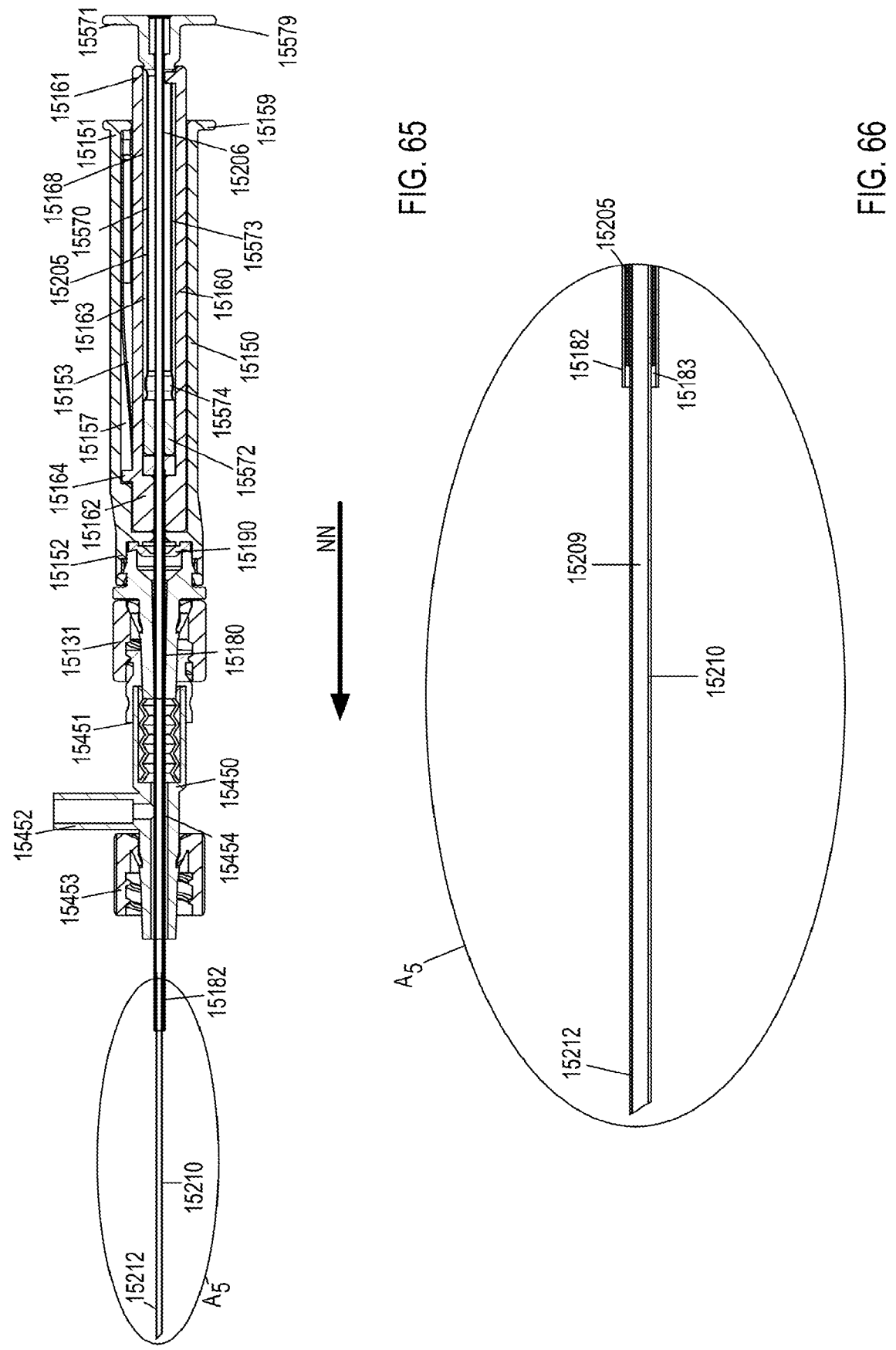
FIG. 65 is a cross-sectional view of the fluid transfer device taken along the line 59-59 in FIG. 58, in a third configuration.
FIG. 66 is an enlarged view of a portion of the fluid transfer device of FIG. 65 indicated by the region $A_5$.

As shown in FIG. 66, the movement of the actuator 15570 to its distal position relative to the second member 15160 advances the catheter 15200 in the NN direction to a position in which at least the distal end portion 15212 of the catheter 15200 is disposed in and extends past the PIV. Moreover, the catheter 15200 can be advanced such that the distal end portion 15212 of the catheter 15200 extends beyond the distal end portion 15182 of the guide member 15180. Thus, the catheter 15200 can be arranged such that when the actuator 15570 is in its distal position relative to the second member 15160 and the second member 15160 is in its distal position relative to the first member 15150, the distal end portion 15212 of the catheter 15200 is disposed in a vascular structure and at least partially outside of the PIV and the guide member 15180. Thus, the lumen 15209 of the catheter 15200 can receive a flow of bodily fluid, which in turn, can flow through the lumen 15209 to be disposed in the fluid reservoir. For example, in some embodiments, the fluid reservoir can be an evacuated reservoir such as a Vacutainer®, which can exert a suction force through the lumen 15209 of the catheter 15200. Thus, the bodily fluid (e.g., blood) is drawn through the lumen 15209 of the cannula 15200 and the lumen 15253 of the secondary cannula 15250 and into the fluid container. In this manner, a phlebotomist can collect (e.g., draw) a given amount of blood through an existing peripheral intravenous line without the need for additional needle sticks.

Figure 67:
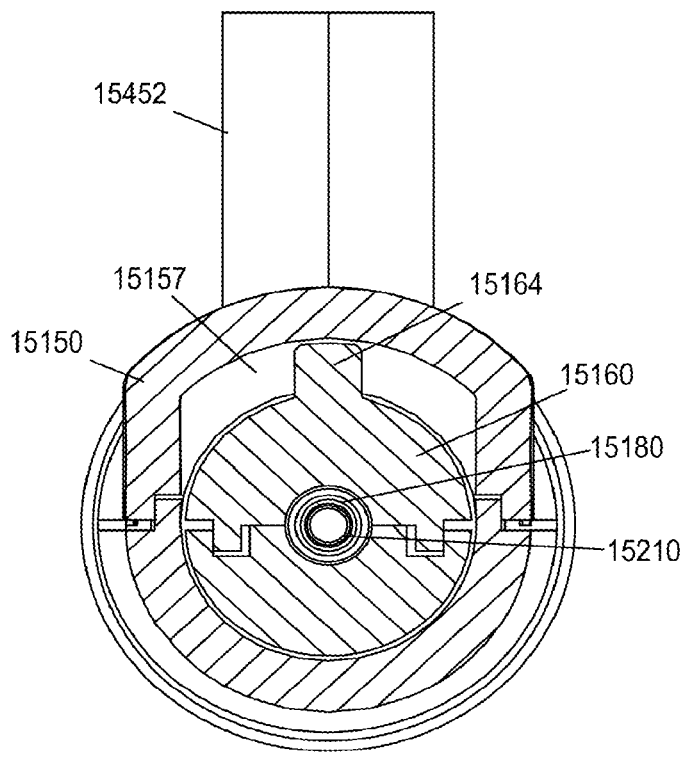
FIGS. 67 and 68 are cross-sectional views of the fluid transfer device of FIG. 47 taken along the line 67-67, in the third configuration and a fourth configuration, respectively.
Figure 68:
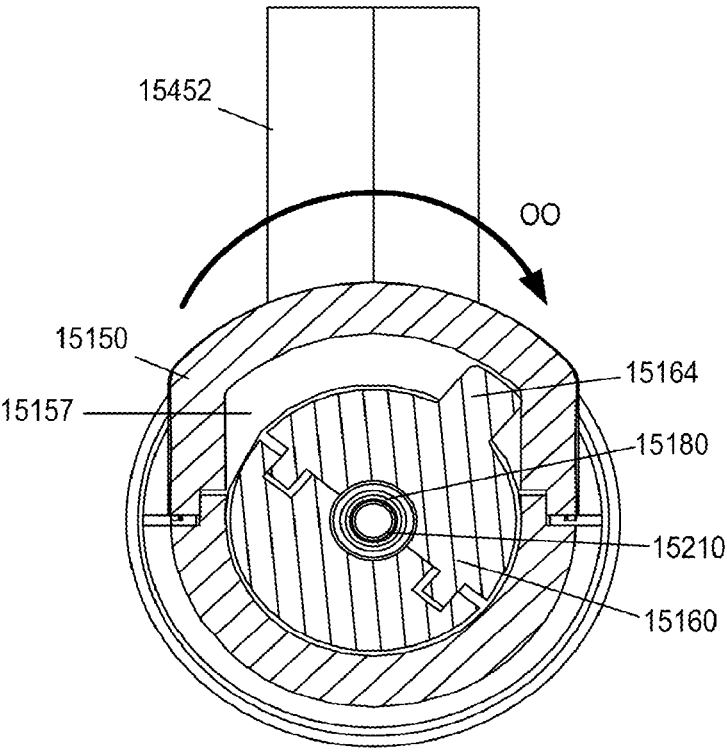

As shown in FIGS. 67 and 68, in some embodiments, it may be desirable to rotate the catheter 15200 relative to the first member 15150, thereby rotating the distal end 15212 within the vascular structure (e.g., to prevent a suctioning of the distal end 15212 to a wall of the vascular structure). Thus, in such instances, the user can manipulate, for example, the actuator 15570 to rotate the actuator 15570 and the second member 15160 relative to the first member 15150. More specifically, the arrangement of the second protrusion 15169 within the slot 15573 defined by the actuator 15570 can be such that the actuator 15570 is maintained in a substantially fixed angular position relative to the second member 15160. Thus, manipulation of the actuator 15570 by the user can result in a rotation of both the actuator 15570 and the second member 15160 relative to the first member 15150.

As described above, the channel 15157 can have a cross-sectional shape and/or area at or near the proximal end portion 15151 of the first member 15150 that is associated with and/or slightly larger than a size of the first protrusion 15164, thereby limiting the rotational range of motion of the second member 15160 when disposed in the proximal position. With the second member 15160 in the distal position, however, the cross-sectional shape and/or area of the channel 15157 at or near the distal end portion 15152 of the first member 15150 (i.e., the second cross-sectional area CA₂) can allow the second member 15160 to rotate about 30 degrees, about 60 degrees, about 90 degrees, about 120 degrees, about 180 degrees, about 210 degrees, or more relative to the longitudinal centerline CL. That is to say, in some embodiments, the second member 15160 can rotate in a clockwise motion or a counterclockwise motion about the longitudinal centerline CL and relative to a center position of the first protrusion 15164 (see e.g., FIG. 67) in a range between about 0 degrees to about 105 degrees, as indicated by the arrow OO in FIG. 68.

In some instances, such rotation of the actuator 15570 and the second member 15160 can, for example, reduce a likelihood of the distal end 15212 of the catheter 15200 forming suction against a wall of the vascular structure (e.g., a vein). For example, by rotating the catheter 15200 the one or more openings defined by the distal end 15212 are also rotated, which in turn, can reduce the likelihood of the distal end 15212 adhering to a wall of the vascular structure due to a suction force within the catheter 15200 (e.g., via an evacuated fluid reservoir or the like). In some instances, it may be desirable to rotate the second member 15160 as the actuator 15570 is being moved toward its distal position. Such rotation can, in some such instances, facilitate the advancement of the catheter 15200 by rotating the catheter 15200 such that a beveled surface or the like (as described above) is aligned with a kinked surface of the guide member 15180 and/or vascular structure. In some instances, the alignment of the beveled surface of the catheter 15200 and the kinked surface can facilitate the passage of the catheter 15200 though the kinked region.

In some instances, it may be desirable to move the catheter 15200 in an axial direction relative to the first member 15150 and/or the second member 15160. More specifically, the arrangement of the second member 15160 and the actuator 15570 is such that the second protrusion 15169 is disposed within the slot 15573 defined by the actuator 15570 in a position that is proximal to the protrusions 15574. Thus, the second protrusion 15169 can move relatively free within the slot 15563. In some embodiments, however, the catheter 15200 can be disposed within the guide member 15180 such that a friction force is defined therebetween. As such, a movement of the actuator 15570 in the axial direction (i.e., the proximal direction and/or the distal direction) can similarly, result in an axial movement of the second member 15160 relative to the first member 15150.

In other embodiments, it may be undesirable for the second member 15160 to move concurrently in the axial direction with the actuator 15570. For example, in some instances, such movement of the second member 15160 can place the distal end portion 15182 of the guide member 15180 in an undesired position relative to, for example, the PIV. In such embodiments, the arrangement of the guide member 15180 of the second member 15160 and the seal member 15190 of the first member 15150 can, for example, limit and/or substantially prevent axial movement of the second member 15160 relative to the first member 15150. More specifically, as described above, the seal member 15190 is disposed about the guide member 15180 and can be in contact therewith to define both a substantially fluid tight seal as well as an amount of friction. In some embodiments, the amount of friction (i.e., a friction force) and/or an amount of drag can be sufficient to limit and/or substantially prevent an axial movement of the second member 15160 relative to the first member 15150. Thus, the actuator 15570 can be moved in the axial direction relative to the second member 15160 until a force is exerted on the second member 15160 that is sufficient to overcome the friction force between the seal member 15190 and the guide member 15180. With the actuator 15570 being a substantially fixed angular or rotational position relative to second member 15160, however, at least a portion of a force exerted to rotate the actuator 15570 is transferred to and/or otherwise exerted on the second member 15160 and thus, when the force is sufficient to overcome the friction force between the seal member 15190 and the guide member 15180, the actuator 15570 and the second member 15180 are rotated relative to the first member substantially concurrently.

With the desired amount of bodily fluid collected, the user (e.g., phlebotomist) can move the actuator 15570 in the proximal direction to retract the catheter 15200. For example, in some instances, the user can exert a force on the engagement portion 15579 of the actuator 15570 in the proximal direction, which is sufficient to move at least the actuator 15570 from its distal position toward its proximal position relative to the second member 15160. In some embodiments, the second member 15160 can be configured to be moved at least in part with the actuator 15570 from its distal position toward its proximal position relative to the first member 15150. In some instances, the force can be sufficient to place the actuator 15570 and the second member 15160 in their respectively proximal positions. Moreover, the arrangement of the actuator 15570 and the introducer 15100 is such that the actuator 15570 is prevented from being removed from the second member 15160 and the second member 15160 is prevented from being removed from the first member 15150, as described above. Thus, the guide member 15180 and the catheter 15200 can be disposed in a proximal position relative to a distal end of the first member 15150.

Although the actuator 15570 and the second member 15160 are described above as being moved in response to a force exerted in the proximal direction applied by the user, in other embodiments, the actuator 15570 and/or the second member 15160 can be configured to move in the proximal direction in an at least semi-automatic manner. For example, in some embodiments, the introducer 15100 can include one or more bias members configured to exert a force to move the second member 15160 and/or the actuator 15570 in the proximal direction. Expanding further, the bias member can exert a reaction force in response to the force exerted on actuator 15579. Thus, once a desire volume of bodily fluid is disposed in the fluid reservoir, the user can remove the force applied on the actuator 15570 and as a result, the bias member can exert a force to move the second member 15160 and the actuator 15570 in the distal direction. In other embodiments, the introducer 15100 can include a bias member connected to a retraction mechanism. In such embodiments, the user can place the second member 15160 and the actuator 15570 in the respective distal positions and can further exert a force in the distal direction that can engage the retraction mechanism (e.g., engages a switch, a lock, a latch, a tab, a retention member, etc.), which in turn, can actuate the bias member to exert a force on the second member 15160 and the actuator 15570 in the proximal direction. In some embodiments, the engagement of the retraction mechanism can be associated with an indicator such as a haptic, tactile, auditory, and/or visual output, which can be transitioned from a first state to a second state during a retraction process, as described above.

Although the rotational range of motion of the second member 15160 relative to the first member 15150 is shown and described above as being defined at least in part by the channel 15157, in other embodiments, the first member 15150 and the second member 15160 of the introducer 15100 can be arranged in any suitable manner. For example, in some embodiments, the inner surface 15153 of the first member 15150 can have a proximal portion having a first cross-sectional shape (e.g., substantially D-shaped) and a distal portion having a second cross-sectional shape different from the first shape (e.g., substantially circular), while the outer surface 15163 of the second member 15160 can have a proximal portion having the second cross-sectional shape and a distal portion having the second cross-sectional shape. As such, when the second member 15160 is disposed in a proximal position within the inner volume 15155 of the first member 15150, the cross-sectional shapes are substantially aligned, which in turn, can limit a rotational motion of the second member 15160 relative to the first member 15150. Conversely, when the second member 15160 is advanced to a distal position within the inner volume 15155 of the first member 15150, the cross-sectional shapes are not substantially aligned, which in turn, can allow for a rotational motion of the second member 15160 relative to the first member 15150.

While the introducer 15100 and the actuator 15570 are particularly shown and described above with reference to FIGS. 47-68, in other embodiments, a device can include an introducer and/or an actuator of any suitable configuration while maintaining a substantially similar functionality. For example, FIGS. 69-72 illustrate a first member 16150 included in an introducer (not shown in FIGS. 69-72) according to another embodiment. As described above, the first member 16150 includes a proximal end portion 16151, a distal end portion 16152, and an inner surface 16153. The inner surface 16153 defines an inner volume 16155 and a channel 16157. The distal end portion 16152 of the first member 16150 includes and/or is otherwise coupled to a locking mechanism 16131. The locking mechanism 16131 can be substantially similar to any of those described herein. In some embodiments, the locking mechanism 16131 can be a Luer Lok™ or the like. As such, a first end of the locking mechanism 16131 is coupled to the distal end portion 16152 of the first member 16150 and a second end, opposite the first end, can be coupled to an adapter (e.g., the adapter 15450 in FIG. 47). Alternatively, in some instances, the second end of the locking mechanism 16131 can be coupled directly to a PIV (not shown in FIGS. 69-72).

As shown in FIG. 50, the lock mechanism 16131 includes a seal member 16190 that is in contact with, for example, a distal surface of the first member 16150 to define a substantially fluid tight seal. In use, the seal member 16190 can receive, for example, a portion of a second member included in the introducer and/or a cannula or catheter (e.g., coupled to an actuator) to be advanced beyond the seal member 16190 in the distal direction while maintaining a substantially fluid tight seal around the portion of the second member and/or cannula or catheter, thereby substantially preventing a backflow of fluid into a volume proximal to the seal member 16190 (and outside of the second member and/or cannula or catheter). The seal member 16190 can be any suitable configuration such as, for example, an O-ring, a one-way valve, a diaphragm, a self-healing diaphragm, a check valve, or any other suitable seal member such as those described herein (e.g., the seal member 15190). Moreover, the arrangement of the seal member 16190 can be such that when in contact with a guide member and/or a catheter, a desired friction force is defined therebetween. In such embodiments, the friction force can be configured to resist and/or otherwise produce drag in response to an applied force that would otherwise move the guide member (e.g., coupled to a second member of the introducer, as described above with reference to the introducer 15100) in a axial direction. As such, the drag produced by the friction force defined between the seal member 16190 and the guide member can, for example, maintain the guide member and thus, a second member of the introducer to which it is coupled, in a substantially fixed position relative to the first member while allowing, for example, the catheter and/or an actuator coupled thereto to move in an axial direction relative to the introducer.

Figures 69, 70:
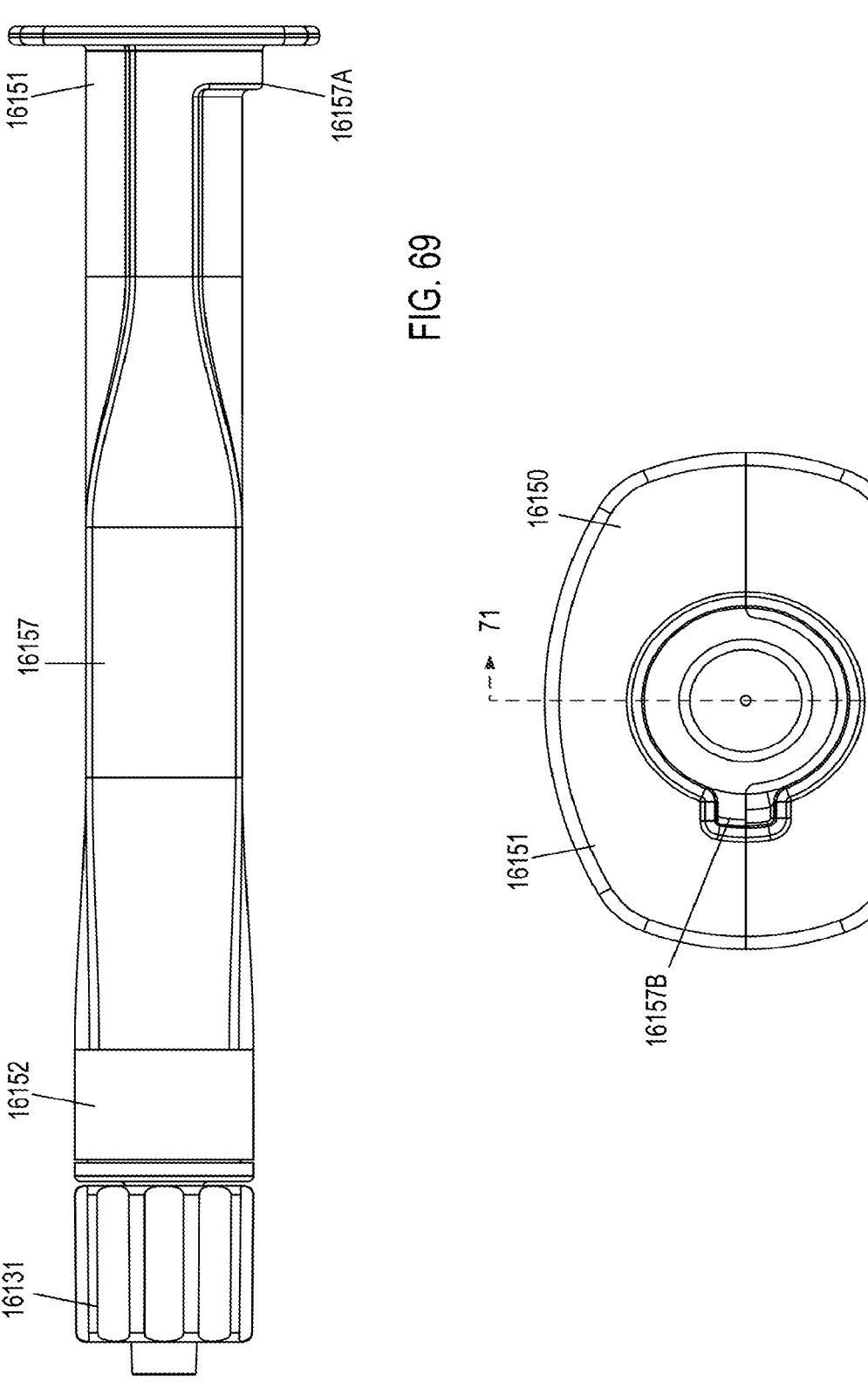
FIG. 69 is a top view of a first member of an introducer according to another embodiment.
FIG. 70 is a rear view of the first member of FIG. 69.
Figures 71, 72:
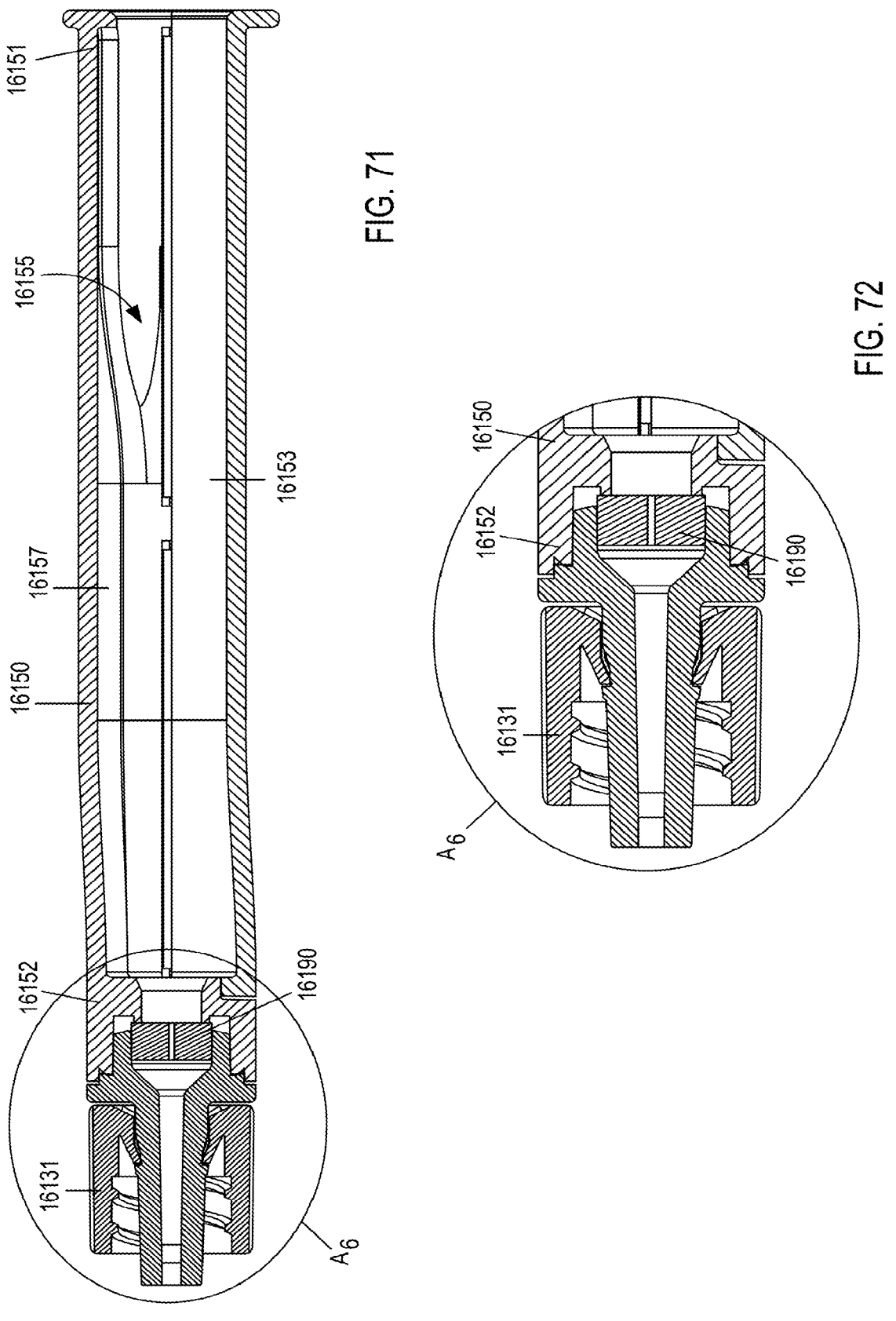
FIG. 71 is a cross-sectional view of the first member taken along the line 71-71 in FIG. 70.
FIG. 72 is an enlarged view of a portion of the first member identified in FIG. 71 by the region $A_6$.
Figures 73, 74:
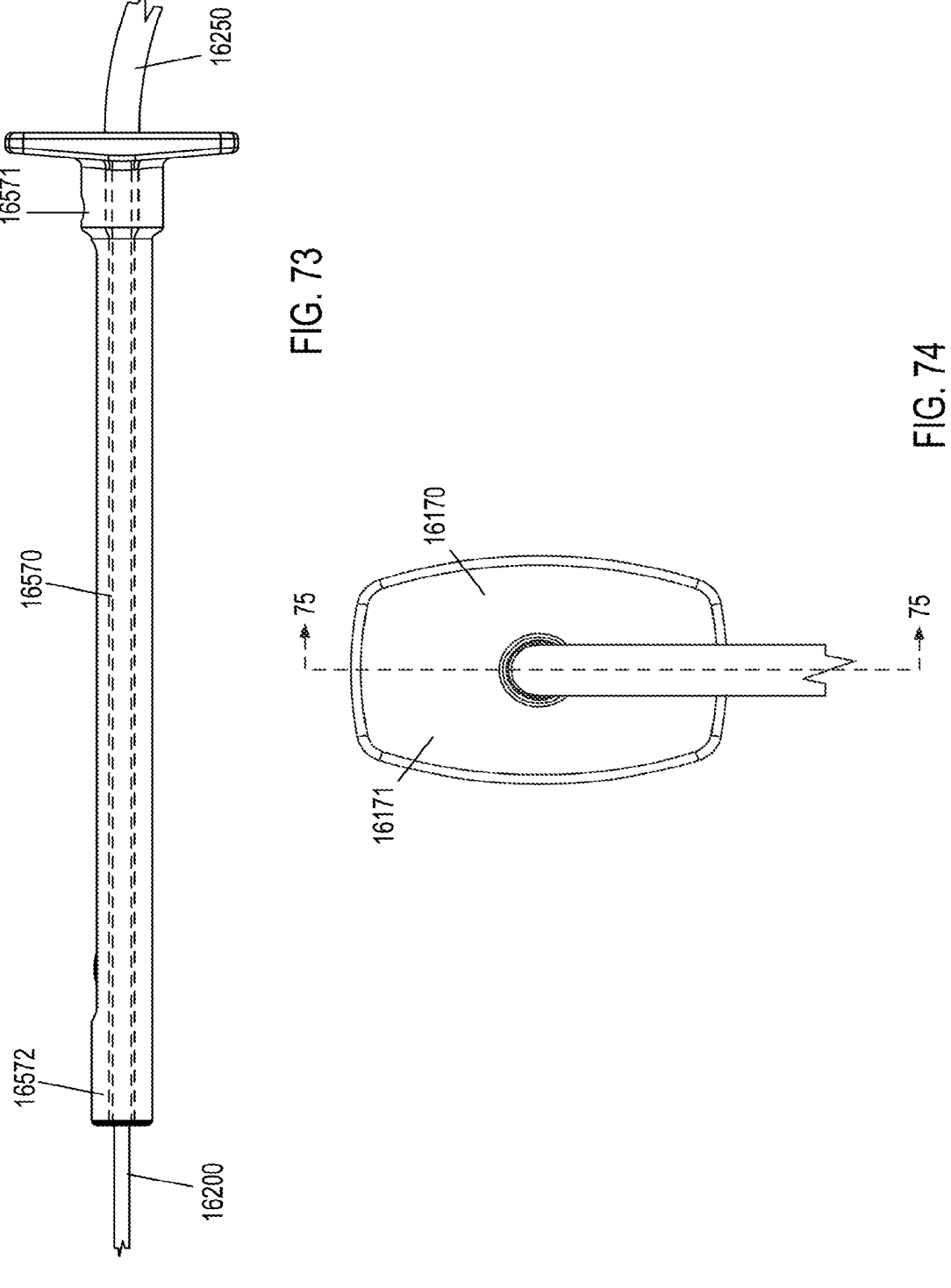
FIG. 73 is a top view of an actuator according to another embodiment.
FIG. 74 is a rear view of the actuator of FIG. 73.

As described above, the inner surface 16153 defines the channel 16157. The channel 16157 extends along a length of the first member 16150 between the proximal end portion 16151 and the distal end portion 16152, as shown in FIG. 69. More particularly, the arrangement of the channel 16157 as defined by the inner surface 16153 is such that the channel 16157 does not extend through the distal end portion 16152. In other words, at least a distal end portion the channel 16157 is bounded by the inner surface 16153. Thus, the channel can function in a similar manner as described above with reference to the first member 15150.

As shown in FIGS. 69 and 70, a proximal end portion of the channel 16157 can extend in a circumferential direction. More particularly, in some embodiments, the proximal end portion of the channel 16157 can form a dogleg 16157A and/or can be substantially L-shaped. In this manner, a portion of the channel 16157 disposed at and/or near the end of the doglegged portion 16157 can extend through the proximal end portion 16151 of the first member 16150. That is to say, the proximal end portion 16151 of the first member 16150 can define a substantially circular opening (i.e., associated with the inner volume 16155), which can include a notched portion 16157B or key-holed portion corresponding with an end portion of the dogleg 16157A of the channel 16157. Thus, a limited portion of the channel 16157 can extend through the proximal end portion 16151 of the first member 16150. Similarly stated, the channel 16157 can be substantially enclosed and/or bounded by the inner surface except for the notched portion 16157B.

In some embodiments, such an arrangement can allow, for example, a second member of the introducer (e.g., substantially similar to the second member 15160 of the introducer 15100) to be inserted into the first member 16150. In some embodiments, the second member can include a protrusion (e.g., similar to or the same as the first protrusion 15164 of the second member 15160) that is inserted through, for example, the notched portion 16157B and/or key-holed opening corresponding to the doglegged portion 16157A of the channel 16157 (as described above). Once the protrusion s inserted therethrough, the second member can be rotated or clocked to an orientation relative to the first member in which the protrusion is substantially aligned with a portion of the channel 16157 that extends from the proximal end portion 16151 of the first member 16150 to the distal end portion 16152 of the first member 16150. Thus, with the second member in such an orientation, a proximal movement of the second member relative to the first member 16150 is thereby limited. Accordingly, the first member 16150 can function in a substantially similar manner as the first member 15150 described in detail above.

In a similar manner, FIGS. 73-76 illustrate an actuator 16570 according to another embodiment. The actuator 16570 includes a proximal end portion 16571 and a distal end portion 16572 and defines a slot 16573. The proximal end 16540 is coupled to a secondary cannula 16250, which in turn, is configured to be coupled to a fluid reservoir (e.g., a Vacutainer® or the like (not shown in FIGS. 73-76)). As described in detail above with reference to the actuator 15570 and the catheter 15200, the actuator 16570 is coupled to the catheter 16200 such that when the secondary cannula 16250 is coupled to the fluid reservoir, the catheter 16200 is placed in fluid communication with the fluid reservoir.

Figures 75, 76:
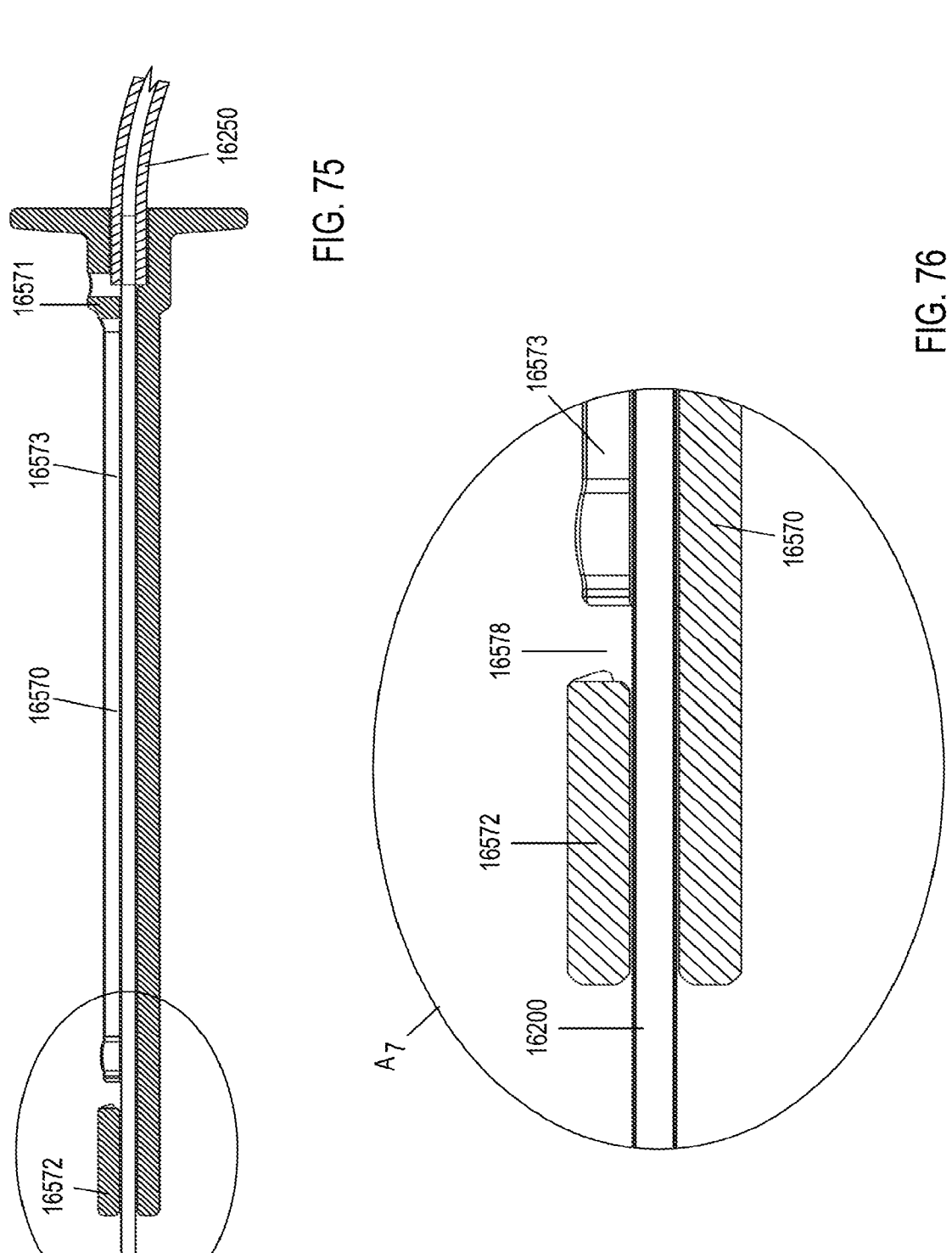
FIG. 75 is a cross-sectional view of the actuator taken along the line 75-75 in FIG. 74.
FIG. 76 is an enlarged view of a portion of the actuator identified in FIG. 75 by the region $A_7$.

As described above, the actuator 16570 is configured to be inserted into a second member of an introducer (not shown in FIGS. 73-76). For example, in some embodiments, the actuator 16570 can be inserted into a second member that is substantially similar to or the same as the second member 15160 described above. As such, the second member can include an inner protrusion (e.g., the second protrusion 15169), which can be disposed within the slot 16573. More particularly, as shown in FIGS. 75 and 76, the actuator 16570 can include an opening 16578 that can be configured to provide access to the slot 16573. In some embodiments, a distal end portion of the slot 16573 can include a dog-legged portion (e.g., as described above with reference to the first member 16150) such that the slot 16573 extends through a side and/or portion of the circumference of the actuator 16570. Thus, the actuator 16570 can be partially disposed in the second member and oriented such that the opening 16578 is aligned with the inner protrusion. Once the inner protrusion is inserted therethrough, the actuator 16570 can be rotated or clocked to an orientation relative to the second member in which the inner protrusion is substantially aligned with a portion of the slot 16573 channel that extends from the proximal end portion 16571 of the actuator 16570 to the distal end portion 16572 of the actuator 16570. Thus, with the actuator 16570 in such an orientation, a proximal movement of the actuator relative to the second member is thereby limited. Accordingly, the actuator 16570 can function in a substantially similar manner as the actuator 15570 described in detail above.

Referring to FIG. 69, a flowchart is shown illustrating a method 200 of phlebotomy through a peripheral intravenous line, according to another embodiment. The method includes coupling a fluid transfer device to a peripheral intravenous line (PIV), 201. The fluid transfer device can be any suitable device configured for phlebotomy through a PIV. For example, in this embodiment, the fluid transfer device can be substantially similar to the fluid transfer device 15000 described above with reference to FIGS. 47-68. As such, the fluid transfer device includes an introducer, an actuator, and a catheter. The introducer includes a first member and a second member movably disposed within the first member, as described above with reference to FIGS. 48-55. The second member is coupled to a guide member. The actuator is movably disposed in the second member and is coupled to the catheter.

A first force is exerted on the actuator that is sufficient to move the second member relative to the first member from a first position, in which a guide member coupled to the second member is disposed within the first member, to a second position, in which a distal end portion of the guide member is inserted through a port of the PIV, at 202. More particularly, the force exerted on the actuator moves the actuator and the second member in the distal direction relative to the first member, while the actuator remains in a relatively fixed position (e.g., a proximal position) relative to the second member. For example, in some embodiment, the second member can be configured to move relative to the first member in response to a first amount of force and the actuator can be configured to move relative to the second member in response to a second amount of force, greater than the first amount of force. For example, in some embodiment, the first member can selectively engage a portion of the second member to temporarily retain the second member in the first position relative to the first member. Similarly, the second member can selectively engage a portion of the actuator to temporarily retain the actuator in a first position relative to the second member, as described in detail above. Furthermore, the guide member can have a length and a hardness that are each sufficient to allow the guide member to pass through the port of the PIV substantially without kinking, breaking, and/or otherwise plastically deforming.

With the second member in the second position (e.g., a distal position), a second force is exerted on the actuator that is sufficient to move the actuator relative to the second member such that a distal end portion of the catheter extends past an end of the peripheral intravenous line, at 203. More specifically, the catheter can be at least partially disposed in the introducer prior to the actuator being moved relative to the second member such that at least a distal end portion of the catheter is disposed in the guide member. Therefore, with the actuator coupled to the catheter, the movement of the actuator relative to the second member moves the catheter relative to the guide member. In this manner, when the actuator is in a distal position relative to the second member, the catheter can extend through the PIV and the guide member to dispose the distal end portion of the catheter in a distal position relative to the guide member and the PIV, as described above with reference to FIGS. 65 and 66.

In some instances, it may be desirable to rotate the second member and/or the actuator relative to the first member as the actuator and/or the second member are being moved relative to the first member. For example, as described above in some embodiments, the first member can define a channel configured to receive a portion of the second member. In this manner, a surface defining the channel can define, for example, a range of motion associated with the second member relative to the first member. As described above with reference to FIGS. 51, 52, 67, and 68, the channel can define the range of motion of the second member relative to the first member that can include, for example, a translational movement (e.g., in a proximal or distal direction) and a rotational movement. In some instances, a portion of the first force and/or a portion of the second force can rotate the second member and the actuator relative to the first member. Such rotation can, for example, facilitate the advancement of the guide member and/or the catheter through a portion of the PIV and/or the like. In other instances, a force can be exerted on the actuator when the distal end portion of the catheter extends past the end of the PIV to limit a suctioning of the distal end portion of the catheter to a vascular structure in which it is disposed. Thus, the catheter can be rotated to reduce the likelihood of the distal end portion of the catheter suctioning to a wall of the vascular structure within which it is disposed and/or to facilitate the advancement of the catheter past an obstruction included within the guide member, the PIV, and/or the vascular structure.

A fluid reservoir is coupled to the fluid transfer device, at 204. The fluid reservoir can be any suitable reservoir. For example, in some embodiments, the fluid reservoir can be an evacuated reservoir such as a Vacutainer® or the like. Moreover, when the fluid reservoir is coupled to the fluid transfer device, the catheter is placed in fluid communication with the fluid reservoir. Thus, a bodily fluid can flow (e.g., in response to a negative pressure and/or suction force) from the body, through the catheter, and into the fluid reservoir. In some instances, while withdrawing a volume of bodily fluid, it can be desirable to move at least the distal end portion of the catheter in an axial direction to, for example, limit and/or substantially prevent a suctioning of the distal end portion of the catheter to, for example, the vascular structure in which it is disposed. In this manner, the user can exert a force in the distal direction to correspondingly advance the catheter in the distal direction or can exert a force in the proximal direction to correspondingly retract the catheter in the proximal direction (e.g., while still being disposed distal to the PIV). Moreover, in some embodiments, the first member of the introducer can include a seal member and/or the like that can engage, for example, the guide member coupled to the second member of the introducer. In such embodiments, the seal member can contact the guide member such that a friction force sufficient to maintain the second member in a substantially fixed position as the catheter is moved in the distal or proximal direction is defined therebetween. Thus, the catheter and thus, the actuator can be moved relative to the introducer.

After a volume of bodily fluid is transferred to the fluid reservoir, the catheter is withdrawn from the PIV and disposed within the introducer, at 205. For example, in some instances, a third force is exerted on the actuator. The third force can be, for example, exerted in the proximal direction and can be which is sufficient to move at least the actuator from a distal position toward a proximal position relative to the second member. In some embodiment, the third force can be exerted by a user. In other embodiments, the third force can be exerted, for example, by a bias member or the like in response to an actuation, as described above. In some embodiments, the second member can be configured to be moved at least in part with the actuator from a distal position toward a proximal position relative to the first member. Moreover, the arrangement of the actuator and the introducer is such that the actuator is prevented from being removed from the second member and the second member is prevented from being removed from the first member, as described above. Thus, the guide member and the catheter can be disposed in a proximal position relative to a distal end of the first member. In some instances, on the catheter and the guide member are disposed in the proximal position relative to the distal end of the first member, the fluid transfer device can be discarded.

The components of the blood draw apparatus and the Y-adapter can be packaged together or separately. The Y-adapter can also be sold in a package with other IV dressing materials. In some embodiments, the Y-adapter can remain on the IV as long as the IV is in the patient.

The blood draw apparatus can be used with a variety of peripheral IVs. The apparatus allows efficient blood draw while still maintaining the integrity of the sample. In some embodiments, for example, the apparatus will facilitate 20 ml of blood to be drawn in approximately 1-2 minutes. While extracting blood, the blood flow can be laminar to avoid turbulence in the catheter, thereby minimizing hemolysis.

While the blood draw apparatus can be used in a variety of settings (ER, in-patient, etc.), two examples of scenarios are described herein. In the first scenario, the patient has a single peripheral IV. In the second scenario, which is typically less common, the patient has a dedicated second peripheral IV just for phlebotomy purposes. Only one y-adapter is required per patient, and can be attached for the life of the IV, for example, which is typically 3-4 days. A new blood draw apparatus (e.g., any of those described above) can be used for each blood draw.

The assembly of the blood draw apparatus can be the same in either scenario. First, the apparatus is coupled to the y-adapter. Second, the catheter is advanced through the y-adapter and pushed through the peripheral IV catheter into the patient's vein. Once in the vein, a syringe or a negative pressure collection container/tube (e.g., a Vacutainer® tube) is connected to the rear port and fluidically coupled to the catheter to draw and store blood.

The following scenario is provided by way of example. The nurse or phlebotomist inserts a peripheral IV into a patient's arm. The peripheral IV is inserted following standard guidelines and the y-adapter is attached. When it is time to draw blood, the provider can turn off the IV, if it is on, for approximately 1-5 minutes to allow medicine or IV fluids to disperse from the blood-drawing site. To draw the blood sample, the provider attaches the blood draw apparatus to the blood draw port on the y-adapter, advances the internal catheter through the peripheral IV and into the vein. Next, the provider can attach the negative pressure collection container(s)/tube(s) to the apparatus (i.e., place the tube in fluid communication with the blood draw apparatus) to extract the blood sample. In use, a user can discard, for example, the first 3-6 ml of the fluid or blood sample as "waste" then using the next tube(s) as the intended sample. This "wasting" procedure ensures all of the dead space fluid, like saline or medications, is cleared from the vein, peripheral IV and y-adapter as to not contaminate the testing sample being drawn.

In the scenario in which there is a dedicated peripheral IV line for blood draw purposes, the provider inserts a peripheral IV into one arm to administer medicine and another peripheral IV into the opposite arm specifically for blood drawing purposes. When it is time to draw blood, the provider simply follows the steps mentioned above and there is no need to wait the 1-5 minutes to allow fluid or medicine dispersal as in the first scenario.

Each of the components discussed herein can be monolithically constructed or can be a combination of parts. For example, in reference to FIG. 7, the y-adapter 5400 and the introducer 5100 are coupled using locking mechanisms 5431 and 5131, respectively. The y-adapter 5400 and the introducer 5100 can be the same component, wherein the y-adapter 5400 is an integral part of the introducer 5100 and vice-versa. By way of another example, while the first member 15150 of the introducer 15100 is shown and described above with reference to FIGS. 48-52 as including the first half 15150A and the second half 15150B which are, for example, coupled together during a manufacturing process to form the first member 15150, in other embodiments, the first member 15150 can be monolithically formed.

Similarly, the components described herein can be assembled in any suitable manner during, for example, a manufacturing process and/or at a point of use. For example, in some embodiments a manufacturing process associated with the fluid transfer device 15000 (and/or a device substantially similar to thereto) can include placing the second member 15160 in a desired position relative to the first half 15150A or the second half 15150B of the first member 15150 prior to the first half 15150A and the second half 15150B being coupled together to form the first member 15150. Thus, the second member 15160 can be disposed between the first half 15150A and the second half 15150 when the first half 15150A and the second half 15150B are coupled together and as a result, the first protrusion 15164 can be disposed in the channel 15157 prior to the first member 15150 being formed, which in some instances, can facilitate the assembly of the fluid transfer device 15000 based at least in part on the channel 15157 being bounded by the inner surface 15153.

In other embodiments, the protrusion 15164 can be, for example, spring loaded and/or otherwise configured to be moved in the radial direction relative to the second member 15160. As such, the first member 15150 can be formed by a manufacturing process (e.g., by coupling the first half 15150A to the second half 15150B) and the second member 15160 can be subsequently disposed in the inner volume 15155. For example, with the first half 15150A being coupled to the second half 15150B to form the first member 15150, the second member 15160 can be placed in a desired position relative to the first member 15150 and the first protrusion 15164 can be moved in a radial direction toward a center of the second member 15160 such that an end surface of the first protrusion 15164 is disposed substantially adjacent to the outer surface 15163 of the second member 15160. In this manner, the distal end portion 15162 of the second member 15160 can be inserted into the inner volume 15155. Moreover, once the second member 15160 is placed in a position within the inner volume 15155 associated with an alignment of the first protrusion 15164 and the channel 15157, the first protrusion 15164 can move in the radial direction away from the center of the second member 15160 (e.g., in response to a force exerted by a spring or the like). Thus, the second member 15160 need not be disposed between the first half 15150A and the second half 15150B prior to the first half 15150A and the second half 15150B being coupled together to form the first member 15150.

Other aspects of the apparatus shown and described can be modified to affect the performance of the apparatus. For example, the openings in the set of openings described herein at the distal end of the catheter can be in any arrangement, size shape, and/or number, to create preferable flow conditions through the catheter. By way of another example, any portion of the catheters described herein can be disposed within a substantially sterile sleeve, bag, tube, cover, and/or the like that can maintain the sterility of the catheter prior to use of the device. In addition, while components of the embodiments have been described herein as having a given hardness, durometer, and/or stiffness, in other embodiments, some components can be substantially rigid. For example, in some embodiments, the introducer 6100 can be formed from a substantially rigid material. Similarly, any of the guide tubes and/or members described herein can be formed from a rigid material such as, for example, a metal or hard plastic. For example, in some embodiments, a guide member can be a metal hypotube or the like. In some embodiments, the arrangement of a catheter (e.g., the catheter 15200) disposed within a lumen defined by a guide member (e.g., the guide member 15180) can be such that the catheter and the guide member collectively define a stiffness that is, for example, a sum of a stiffness of the catheter and a stiffness of the guide member. Thus, in some embodiments, the guide member can have a stiffness that is substantially similar to a stiffness of the catheter, wherein a collective stiffness defined thereby is sufficient to allow the guide member to pass through at least a portion of a PIV (e.g., a hub, a basket, or the like).

By way of another example, any of the catheters, cannulas, flow tubes, and/or the like described herein can include and/or can otherwise receive, for example, a guide wire, stiffening wire, lattice and/or matrix structure, stent, balloon, and/or the like that can increase a stiffness associated with the catheter and/or otherwise limit and/or substantially prevent a kinking, pinching, and/or plastic deformation of at least a portion of the catheter. For example, in some embodiments, the catheter 15200 can include, for example, a guide wire or the like that can be disposed in the lumen 15209 while the catheter 15200 is placed in its distal position, thereby increasing a stiffness associated with the catheter 15200. When the distal end 15212 of the catheter 15200 is in a desired position relative to the PIV (i.e., distal to a distal end of the PIV), the guide wire can be retracted through the lumen 15209 to be removed from the catheter 15200.

While the second portion 15210 (e.g., a distal end portion) of the catheter 15200 is particularly shown and described above, in other embodiments, a catheter can have a distal end portion with any suitable configuration. For example, FIG. 78 is a schematic illustration of a distal end portion 17212 of a catheter, according to another embodiment. As shown, the distal end portion 17212 of the catheter can define a channel or the like. Expanding further, a first portion of the catheter (not shown in FIG. 78) can have, for example, an annular cross-sectional shape, while a second portion of the catheter (i.e., the distal end portion 17212) can have, for example, a semi-annular cross-sectional shape. In other words, the distal end portion 17212 can be, for example, cut, skived, shaved, bisected, and/or the like such that the distal end 15212 of the catheter has a semi-circular or semi-annular cross-sectional shape that defines a channel therebetween. Such an arrangement of the distal end portion 17212 can, in some embodiments, allow for a reduced size and/or gauge associated with the distal end 17212 of the catheter, which might otherwise be prone to kinks, obstructions, and/or occlusions. Moreover, the semi-annular arrangement of the distal end portion 17212 can increase flow rate through the catheter, which might otherwise be limited due to a relatively small inner diameter of the catheter and/or a relatively small distal opening of the catheter.

In still other embodiments, a distal end portion of a catheter such as those described herein can include and/or can be coupled to a wound wire, a braided wire, a coiled and/or spiraled wire, a helical wire, a mesh, and/or the like. By way of example, in some embodiments, a distal end portion of a catheter can include and/or can be formed from a relatively small wound or coiled wire. In some embodiments, such a wire can be, for example, tightly wound into a substantially solid cylindrical shape, thereby defining a portion of a lumen. In some instances, such an arrangement can allow at least the distal end portion of the catheter to bend and/or flex substantially without plastically deforming as the catheter is advanced in the distal direction. In some embodiments, the wound wire arrangement of the distal end portion can act, for example, as an auger or the like which can be rotated while being advanced in the distal direction to remove, clear, and/or break apart an obstruction such as, for example, a clot. Moreover, while the catheter 15200 is particularly shown and described above, in some embodiments, the distal end portion 15212 of the catheter 15200 can have any suitable configuration such as those described herein.

While various embodiments have been described above, it should be understood that they have been presented by way of example only, and not limitation. Where schematics and/or embodiments described above indicate certain components arranged in certain orientations or positions, the arrangement of components may be modified. While the embodiments have been particularly shown and described, it will be understood that various changes in form and details may be made. For example, while the device or apparatus 6000 is shown and described above as including the introducer 6100 with a relatively small actuator track 6111 (e.g., a slit), in other embodiments, an introducer can be, for example, a substantially U-shaped channel or the like. In such embodiments, an actuator and a catheter can be at least partially disposed in the introducer and moved relative thereto, as described herein. Moreover, in such embodiments, the catheter can be disposed, for example, within a sterile bag or sleeve. In other embodiments, the introducer can be, for example, a guide rail or the like along which an actuator and catheter can be moved. In such embodiments, the catheter can be disposed, within a sterile bag or sleeve.

Although various embodiments have been described as having particular features and/or combinations of components, other embodiments are possible having a combination of any features and/or components from any of embodiments as discussed above. For example, any of the devices described herein can include an actuator that can be coupled to a catheter and operable in rotating a catheter relative to, for example, a PIV or the like. By way of another example, while the cannula 6200 is shown in FIG. 13A as including the first portion 6205 having the first diameter and the second portion 6210 having the second diameter, in some embodiments, a cannula can include a first portion and a second portion of similar diameter. Furthermore, while the first member 15150 of the introducer 15100 is particularly shown and described as including the seal member 15190, in other embodiments, the first member 15150 can include a seal member substantially similar in form and function to the seal member 16190 included in the first member 16150 described above with reference to FIGS. 69-72, or vice versa. Similarly, the first member 16150 and/or the actuator 16570 (or features included therein) can be included in, for example, the flow transfer device 15000.

By way of another example, any of the catheters and/or cannulas described herein can have a distal end portion with any suitable arrangement. For example, while the distal end portion 15212 of the catheter 15200 is shown as being substantially cylindrical with an angled or beveled tip, in other embodiments, the distal end portion 15212 and/or the second portion 15210 of the catheter 15200 can have any suitable arrangement. For example, FIG. 79 is a schematic illustration of a distal end portion 18212 of a catheter according to another embodiment. As shown, the distal end portion 18212 defines a set of openings 18216 arranged, for example, in a staggered orientation. More specifically, the second portion 18210 of the catheter 18200 can define a set of openings disposed along its circumference similar to the set of openings 1231, 2231, and/or 4231 described above with reference to the catheters 1200, 2200, and 4200, respectively. In such embodiments, the set of openings can be substantially circular, oblong, polygonal, elliptical, and/or any other suitable shape, size, or arrangement. In this manner, the set of openings 18216 can, for example, increase flow rate into the distal end portion 18212 of the catheter, while the staggered and/or offset arrangement of the set of openings 18212 can allow the distal end portion 18212 to remain sufficiently stiff as to limit and/or substantially prevent a collapse of the distal end portion 18212.

Where methods and/or schematics described above indicate certain events and/or flow patterns occurring in certain order, the ordering of certain events and/or flow patterns may be modified. Additionally certain events may be performed concurrently in parallel processes when possible, as well as performed sequentially.

What is claimed is:

1. An apparatus, comprising:
a catheter having a proximal end portion and a distal end portion, the catheter defining a lumen extending through the proximal end portion and the distal end portion of the catheter;
an introducer defining an inner volume, the introducer having a distal end portion configured to be coupled to an indwelling peripheral intravenous line, the introducer configured to transition between a first configuration, in which a guide member is disposed within the introducer, and a second configuration, in which at least a distal end portion of the guide member is distal to the introducer and within the indwelling peripheral intravenous line; and
an actuator coupled to the catheter and configured to transition the introducer between the first configuration and the second configuration, at least the distal end portion of the catheter being isolated within the guide member and moving with the guide member as the introducer is transitioned from the first configuration to the second configuration, the actuator configured to move the catheter relative to guide member when the introducer is in the second configuration such that the distal end portion of the catheter is distal to the guide member.

2. The apparatus of claim 1, wherein the guide member at least partially encloses at least the distal end portion of the catheter when the introducer is transitioned from the first configuration to the second configuration.

3. The apparatus of claim 1, wherein the guide member is disposed in a portion of the indwelling peripheral intravenous line when the introducer is in the second configuration, and
the guide member is disposed between an outer surface of at least the distal end portion of the catheter and an inner surface of the portion of the indwelling peripheral intravenous line prior to the catheter being moved relative to the guide member.

4. The apparatus of claim 1, wherein the actuator is maintained in a fixed position relative to a portion of the introducer when the actuator transitions the introducer from the first configuration to the second configuration.

5. The apparatus of claim 1, wherein the actuator is maintained in a fixed position relative to a portion of the introducer when the actuator transitions the introducer from the first configuration to the second configuration and the actuator is configured to move relative to the portion of the introducer to move the catheter relative to the guide member.

6. The apparatus of claim 1, wherein the guide member has a first stiffness and the catheter has a second stiffness less than the first stiffness.

7. The apparatus of claim 1, wherein a distal end surface of the guide member is configured to be disposed within the peripheral intravenous line when the introducer is in the second configuration, the actuator is configured to move the catheter relative to the guide member to place a distal end surface of the catheter outside of and distal to the peripheral intravenous line.

* * * * *